US009732065B2

(12) United States Patent
Yoshinaga et al.

(10) Patent No.: US 9,732,065 B2
(45) Date of Patent: Aug. 15, 2017

(54) CYCLIC AMINOMETHYL PYRIMIDINE DERIVATIVE

(71) Applicant: Sumitomo Dainippon Pharma Co., Ltd., Osaka (JP)

(72) Inventors: Hidefumi Yoshinaga, Osaka (JP); Yoshiharu Uruno, Takarazuka (JP); Hidetaka Nagata, Suita (JP); Masakazu Hashimoto, Suita (JP); Taro Kato, Osaka (JP)

(73) Assignee: SUMITOMO DAINIPPON PHARMA CO., LTD., Osaka (JP)

( * ) Notice: Subject to any disclaimer, the term of this patent is extended or adjusted under 35 U.S.C. 154(b) by 0 days.

(21) Appl. No.: 14/894,402

(22) PCT Filed: May 29, 2014

(86) PCT No.: PCT/JP2014/064258

§ 371 (c)(1),
(2) Date: Nov. 27, 2015

(87) PCT Pub. No.: WO2014/192868

PCT Pub. Date: Dec. 4, 2014

(65) Prior Publication Data

US 2016/0122319 A1 May 5, 2016

(30) Foreign Application Priority Data

May 30, 2013 (JP) ................................ 2013-113922

(51) Int. Cl.
*C07D 401/14* (2006.01)
*C07D 417/14* (2006.01)

(52) U.S. Cl.
CPC ......... *C07D 401/14* (2013.01); *C07D 417/14* (2013.01)

(58) Field of Classification Search
CPC ............................ C07D 401/14; C07D 417/14
See application file for complete search history.

(56) References Cited

FOREIGN PATENT DOCUMENTS

| | | | |
|---|---|---|---|
| JP | 10-95781 | | 4/1998 |
| KR | 2011111880 | * | 9/2011 |
| WO | 97/13759 | | 4/1997 |
| WO | 2011/051858 | | 5/2011 |
| WO | 2011/111880 | | 9/2011 |
| WO | 2012/054535 | | 4/2012 |
| WO | 2012/063513 | | 5/2012 |
| WO | 2012/082947 | | 6/2012 |

OTHER PUBLICATIONS

International Search Report issued Aug. 5, 2014 in corresponding International (PCT) Application No. PCT/JP2014/064258.

International Preliminary Report on Patentability issued Dec. 1, 2015 in corresponding International (PCT) Application No. PCT/JP2014/064258.

STN International, file REGISTRY [online], [Retrieval date Jul. 18, 2014 (Jul. 18, 2014)], CAS Registry No. 1567296-09-6 (Mar. 12, 2014), 1434966-06-9 (Jun. 5, 2013), 1434897-35-4 (Jun. 5, 2013), 1434511-59-7 (Jun. 5, 2013).

STN International, file REGISTRY [online], [Retrieval date Jul. 18, 2014 (Jul. 18, 2014)], CAS Registry No. 1413500-97-6 (Dec. 11, 2012), 1413495-19-8 (Dec. 11, 2012), 1413160-31-2 (Dec. 10, 2012), 1394571-00-6 (Sep. 18, 2012), 1394554-53-0 (Sep. 18, 2012), 1394529-16-8 (Sep. 18, 2012), 1381725-37-6 (Jul. 5, 2012), 1381661-09-1 (Jul. 5, 2012), 1381658-20-3 (Jul. 5, 2012), 1381635-69-3 (Jul. 5, 2012), 1381615-17-3 (Jul. 5, 2012), 1381554-61-5 (Jul. 5, 2012), 1381552-77-7 (Jul. 5, 2012), 1381551-68-3 (Jul. 5, 2012), 1381539-73-6 (Jul. 5, 2012), 1381518-88-2 (Jul. 5, 2012), 1381513-43-4 (Jul. 5, 2012), 1381512-77-1 (Jul. 5, 2012), 1381503-35-0 (Jul. 5, 2012), 1381502-77-7 (Jul. 5, 2012), 1381464-22-7 (Jul. 4, 2012), 1381457-98-2 (Jul. 4, 2012), 1381454-25-6 (Jul. 4, 2012), 1381412-52-7 (Jul. 4, 2012), 1381412-35-6 (Jul. 4, 2012), 1381370-38-2 (Jul. 4, 2012), 1381369-92-1 (Jul. 4, 2012), 1381349-61-6 (Jul. 4, 2012), 1381338-93-7 (Jul. 4, 2012), 1381320-15-5 (Jul. 4, 2012), 1381317-35-6 (Jul. 4, 2012), 1381310-47-9 (Jul. 4, 2012), 1381308-15-1 (Jul. 4, 2012), 1381298-46-9 (Jul. 4, 2012), 1381296-32-7 (Jul. 4, 2012), 1381291-18-4 (Jul. 4, 2012), 1381289-91-3 (Jul. 4, 2012), 1381267-05-5 (Jul. 4, 2012), 1381266-92-7 (Jul. 4, 2012), 1381262-18-5 (Jul. 4, 2012), 1381226-26-1 (Jul. 4, 2012), 1381223-91-1 (Jul. 4, 2012), 1381222-50-9 (Jul. 4, 2012), 1381218-78-5 (Jul. 4, 2012), 1381043-88-4 (Jul. 4, 2012), 1380993-97-4 (Jul. 4, 2012), 1380904-25-5 (Jul. 3, 2012), 1380884-70-7 (Jul. 3, 2012), 1380870-74-5 (Jul. 3, 2012), 1380869-39-5 (Jul. 3, 2012), 1380807-09-9 (Jul. 3, 2012), 1309218-73-2 (Jun. 13, 2011), 1309119-91-2 (Jun. 13, 2011), 1287458-82-5 (Apr. 29, 2011), 1240092-61-8 (Sep. 7, 2010), 1214614-73-9 (Mar. 25, 2010), 1214584-35-6 (Mar. 25, 2010), 1214503-82-8 (Mar. 25, 2010), 1214474-65-3 (Mar. 25, 2010), 1214451-97-4 (Mar. 25, 2010), 1070272-24-0 (Nov. 3, 2008), 1069783-92-1 (Nov. 2, 2008), 1069635-75-1 (Nov. 2, 2008), 1060381-74-9 (Oct. 13, 2008).

(Continued)

*Primary Examiner* — Alexander R Pagano
*Assistant Examiner* — Ebenezer O Sackey
(74) *Attorney, Agent, or Firm* — Wenderoth, Lind & Ponack, L.L.P.

(57) ABSTRACT

The present invention provides a cyclic aminomethyl pyrimidine derivative and a pharmaceutically acceptable salt thereof with high selectivity for dopamine $D_4$ receptors, which are useful for treating a disease such as attention deficit hyperactivity disorder. Specifically, a compound of formula (1) or a pharmaceutically acceptable salt thereof is provided, wherein n and m are independently 1 or 2; $R^a$ is $C_{1-6}$ alkyl group, $C_{3-6}$ cycloalkyl group, or amino group; $R^b$ is hydrogen atom, $C_{1-6}$ alkyl group or the like, provided that when $R^a$ is amino group, then $R^b$ is hydrogen atom; $R^{c1}$ and $R^{c2}$ are independently hydrogen atom, or $C_{1-6}$ alkyl group; $R^{d1}$ and $R^{d2}$ are independently hydrogen atom, fluorine atom or the like; ring Q is an optionally-substituted pyridyl group or an optionally-substituted isoquinolyl group; and the bond having a dashed line is a single or double bond.

(1)

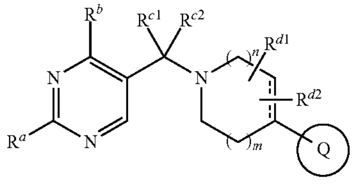

20 Claims, 2 Drawing Sheets

(56) References Cited

OTHER PUBLICATIONS

STN International, file REGISTRY [online], Jul. 5, 2012 (Jul. 5, 2012), [Retrieval date Jul. 18, 2014 (Jul. 18, 2014)], CAS Registry No. 1381719-82-9.

STN International, file REGISTRY [online], [Retrieval date Jul. 18, 2014 (Jul. 18, 2014)], CAS Registry No. 1381645-73-3 (Jul. 5, 2012), 1381537-85-4 (Jul. 5, 2012), 1381451-34-8 (Jul. 4, 2012), 1381288-00-1 (Jul. 4, 2012), 1380801-06-8 (Jul. 3, 2012), 1380790-91-9 (Jul. 3, 2012).

STN International, file REGISTRY [online], [Retrieval date Jul. 18, 2014 (Jul. 18, 2014)], CAS Registry No. 1381313-16-1 (Jul. 4, 2012), 1381218-43-4 (Jul. 4, 2012), 1309213-32-8 (Jun. 13, 2011).

STN International, file REGISTRY [online], Jun. 14, 2012 (Jun. 14, 2012), [Retrieval date Jul. 18, 2014 (Jul. 18, 2014)], CAS Registry No. 1378094-92-8.

STN International, file REGISTRY [online], Oct. 27, 2008 (Oct. 27, 2008), [Retrieval date Jul. 18, 2014 (Jul. 18, 2014)], CAS Registry No. 1066982-12-4.

Haworth et al., "4-Heterocyclyl tetrahydropyridines as selective ligands for the human dopamine D4 receptor", Bioorganic & Medicinal Chemistry Letters, vol. 7, No. 17, 1997, pp. 2211-2216.

Faraone et al., "Molecular Genetics of Attention-Deficit/HyperactivityDisorder", Advancing The Neuroscience of ADHD, Biol Psychiatry, vol. 57, 2005, pp. 1313-1323.

Shaw et al., "Polymorphisms of the Dopamine D4 Receptor, Clinical Outcome, and Cortical Structure in Attention-Deficit/Hyperactivity Disorder", Arch Gen Psychiatry, vol. 64, No. 8, Aug. 2007, pp. 921-931.

Gong et al., "A gene expression atlas of the central nervous system based on bacterial artificial chromosomes", Nature, vol. 425, Oct. 30, 2003, pp. 917-925.

Primus et al., "II. Localization and Characterization of Dopamine D4 Binding Sites in Rat and Human Brain by Use of the Novel, D4 Receptor-Selective Ligand [$^3$H]NGD 94-1", The Journal of Pharmacology and Experimental Therapeutics, vol. 282, No. 2, 1997, pp. 1020-1027.

* cited by examiner

CYCLIC AMINOMETHYL PYRIMIDINE DERIVATIVE

TECHNICAL FIELD

The present invention mainly relates to a cyclic aminomethyl pyrimidine derivative including a salt thereof which has a selective dopamine $D_4$ receptor agonistic effect as well as a medicament for treating a central nervous system disease comprising the derivative as an active ingredient. Particularly, the present invention relates to a cyclic aminomethyl pyrimidine derivative having pyridyl group or isoquinolyl group on the ring moiety of the cyclic aminomethyl group including a salt thereof as well as a medicament for treating a disease such as attention deficit hyperactivity disorder comprising the derivative as an active ingredient.

BACKGROUND ART

Dopamine $D_4$ receptor is one of G protein-coupled receptors (GPCRs), and is highly expressed in frontal association area associated with attention behavior and cognitive function. Hence, a dopamine $D_4$ receptor agonist is expected to be used for treating a central nervous system disease related to higher brain function such as attention deficit hyperactivity disorder (ADHD). ADHD is one of developmental disorders accompanying inattention, hyperactivity, and impulsivity as predominant symptoms, which appear in childhood. Also, it is known that the predominant symptoms of ADHD persist into adulthood. As a first-choice drug for treating ADHD, methylphenidate which is one of central nervous system stimulants has been used. Methylphenidate exhibits a fast-acting therapeutic effect, which is thought to be produced by the regulation of dopamine transporter function associated with the release of dopamine that is a neurotransmitter. However, methylphenidate is at risk for drug dependence or drug abuse, and also at risk for cardiovascular side effects such as palpitation, tachycardia, and blood-pressure variation. Thus, as a medicament for treating ADHD which is at low risk for drug dependence, a selective noradrenaline reuptake inhibitor, atomoxetine which is one of non-central nervous system stimulants has been used. However, atomoxetine requires an adequate period after the administration to exert its therapeutic effect. Accordingly, it has been desired to develop a medicament for treating ADHD, which has a reduced risk for drug dependence and also a reduced risk for cardiovascular side effects, and exhibits a fast-acting therapeutic effect.

Recently, it has been reported that ADHD patients have mutations in dopamine transporter genes or dopamine $D_4$ receptor genes (e.g. Non-Patent Reference 1). Also, it has been reported that children with gene polymorphism in a seven times repeating sequence of 48 bp within the third exon of dopamine $D_4$ receptor genes have the delayed development of cerebral cortex (e.g. Non-Patent Reference 3). In addition, it has been reported that dopamine $D_4$ receptors are highly expressed in frontal association area associated with attention behavior and cognitive function (e.g. Non-Patent Reference 2). Hence, it has been thought that dopamine $D_4$ receptors are associated with attention and cognitive functions. In addition, it is well known that dopamine $D_4$ receptors are not expressed in nucleus accumbens associated with drug dependence.

Accordingly, a drug which exhibits a selective dopamine $D_4$ receptor agonistic effect has been expected as a medicament for treating a central nervous system disease related to dopaminergic nerves, especially a medicament for treating ADHD which exhibits a fast-acting therapeutic effect with reduced side effects such as drug dependence.

Patent Reference 1 discloses a dopamine $D_4$ receptor ligand of formula I:

I

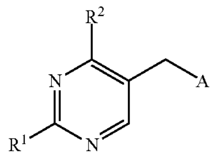

wherein $R^1$ and $R^2$ each individually signify lower-alkyl or amino;

A is $A^1$

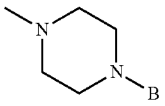

$A^2$

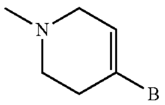

$A^3$

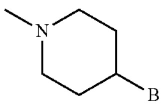

$A^4$

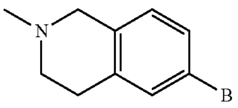

$A^5$

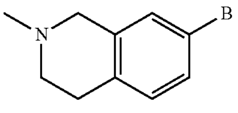

$A^6$

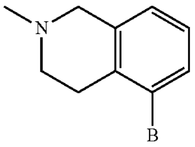

or $A^7$

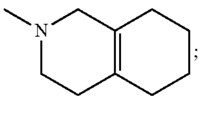

B signifies hydrogen in $A^4$, $A^5$ and $A^6$;

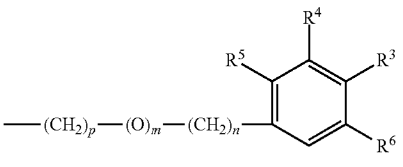

in $A^1$-$A^6$;

lower-alkoxy in $A^4$-$A^6$; and lower-alkyl, styryl, phenylethynyl, or benzoyloxy-lower-alkyl in $A^1$ and $A^2$;

n signifies 0-2;

m, p signify 0, 1; and $R^3$, $R^4$, $R^5$ and $R^6$ each independently signify hydrogen, halogen, lower-alkyl, trifluoromethyl, lower-alkoxy or nitro. Patent Reference 1 also discloses that such compound is useful for the regulation or prophylaxis of a disease caused by disturbance in the dopamine system (e.g. psychosis such as schizophrenia).

Said compound does not encompass compounds wherein B is a heteroaryl ring-containing substituent. Thus, the present compound is different from the compound of Patent Reference 1 in each chemical structure.

PRIOR ART DOCUMENTS

Patent Documents

Patent Reference 1: JP H11-500745

Non-Patent Documents

Non-Patent Reference 1: Biological Psychiatry 2005, 57, 1313.

Non-Patent Reference 2: Archives of General Psychiatry, 2007, 64, 921.

Non-Patent Reference 3: The Journal of Pharmacology Experimental Therapeutics, 1997, 282, 1020.

SUMMARY OF INVENTION

Problem to be Solved by the Invention

An object of the present invention is to provide a novel selective dopamine $D_4$ receptor agonist useful as a medicament for treating a central nervous system disease.

Means for Solving the Problems

The present inventors have extensively studied to reach the above object, and then have found that a compound of the following formula (1) or a pharmaceutically acceptable salt thereof (hereinafter referred to as "the present compound", if necessary) exhibits a remarkable selective dopamine $D_4$ receptor agonistic effect. Based upon the new findings, the present invention has been completed.

The present invention provides inventions of various embodiments described below.

[1] A compound of formula (1):

(1)

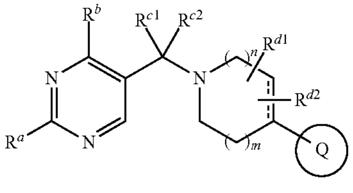

or a pharmaceutically acceptable salt thereof, wherein n and m are independently 1 or 2;

$R^a$ is $C_{1-6}$ alkyl group, $C_{3-6}$ cycloalkyl group, or amino group;

$R^b$ is hydrogen atom, $C_{1-6}$ alkyl group, or amino group which may be optionally substituted with the same or different one or two $C_{1-6}$ alkyl groups, provided that when $R^a$ is amino group, then $R^b$ is hydrogen atom;

$R^{c1}$ and $R^{c2}$ are independently hydrogen atom or $C_{1-6}$ alkyl group;

$R^{d1}$ and $R^{d2}$ are independently hydrogen atom, fluorine atom, or $C_{1-6}$ alkyl group, or $R^{d1}$ and $R^{d2}$ may be combined with the carbon atom(s) to which they are attached to form a 3- to 8-membered cycloalkane ring or a 3- to 8-membered cycloalkene ring, wherein said cycloalkane ring or cycloalkene ring may be optionally substituted with one or two substituents selected independently from the group consisting of halogen atom, $C_{1-6}$ alkyl, and $C_{1-6}$ alkoxy;

ring Q is an optionally-substituted 5- to 10-membered nitrogen-containing heteroaryl group; and the bond having a dashed line is a single or double bond.

[2] A compound of formula (1):

(1)

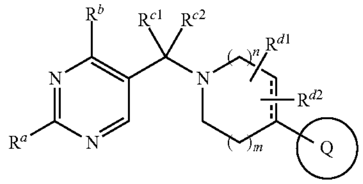

or a pharmaceutically acceptable salt thereof, wherein n and m are independently 1 or 2;

$R^a$ is $C_{1-6}$ alkyl group, $C_{3-6}$ cycloalkyl group, or amino group;

$R^b$ is hydrogen atom, $C_{1-6}$ alkyl group, or amino group which may be optionally substituted with one or two $C_{1-6}$ alkyl groups, provided that when $R^a$ is amino group, then $R^b$ is hydrogen atom;

$R^{c1}$ and $R^{c2}$ are independently hydrogen atom or $C_{1-6}$ alkyl group;

$R^{d1}$ and $R^{d2}$ are independently hydrogen atom, fluorine atom, or $C_{1-6}$ alkyl group, or $R^{d1}$ and $R^{d2}$ may be combined with the carbon atom(s) to which they are attached to form a 3- to 8-membered cycloalkane ring or a 3- to 8-membered cycloalkene ring, wherein said cycloalkane ring or cycloalkene ring may be optionally substituted with one or two substituents selected from the group consisting of halogen atom, $C_{1-6}$ alkyl, and $C_{1-6}$ alkoxy;

ring Q is an optionally-substituted pyridyl group or an optionally-substituted isoquinolyl group; and the bond having a dashed line is a single or double bond.

[3] The compound according to [1] or [2] or a pharmaceutically acceptable salt thereof, wherein the ring Q is a group of the following formula (2a), (2b), (2c), (2d) or (2e):

(2a)

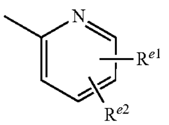

(2b)

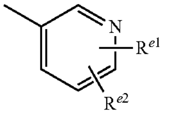

-continued (2c)

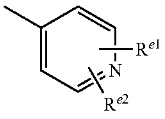

(2d)

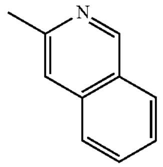

(2e)

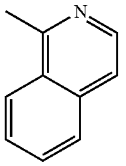

wherein $R^{e1}$ and $R^{e2}$ are independently hydrogen atom, halogen atom, or $C_{1-6}$ alkyl group which may be optionally substituted with the same or different one to three halogen atoms.

[4] The compound according to any one of [1] to [3] or a pharmaceutically acceptable salt thereof, wherein $R^a$ is $C_{1-4}$ alkyl group.

[5] The compound according to any one of [1] to [3] or a pharmaceutically acceptable salt thereof, wherein $R^a$ is amino group, and $R^b$ is hydrogen atom.

[6] The compound according to any one of [1] to [4] or a pharmaceutically acceptable salt thereof, wherein $R^b$ is $C_{1-6}$ alkyl group or amino group.

[7] The compound according to any one of [1] to [4] and [6] or a pharmaceutically acceptable salt thereof, wherein $R^b$ is amino group.

[8] The compound according to any one of [1] to [7] or a pharmaceutically acceptable salt thereof, wherein both $R^{c1}$ and $R^{c2}$ are hydrogen atom.

[9] The compound according to any one of [1] to [8] or a pharmaceutically acceptable salt thereof, wherein $R^{d1}$ and $R^{d2}$ are independently hydrogen atom or $C_{1-6}$ alkyl group.

[10] The compound according to any one of [1] to [9] or a pharmaceutically acceptable salt thereof, wherein both $R^{d1}$ and $R^{d2}$ are hydrogen atom.

[11] The compound according to any one of [3] to [10] or a pharmaceutically acceptable salt thereof, wherein the ring Q is a group of formula (2a) or (2b).

[12] The compound according to [11] or a pharmaceutically acceptable salt thereof, wherein the ring Q is a group of formula (2a).

[13] The compound according to [11] or a pharmaceutically acceptable salt thereof, wherein the ring Q is a group of formula (2b).

[14] The compound according to any one of [3] to [13] or a pharmaceutically acceptable salt thereof, wherein $R^{e1}$ and $R^{e2}$ are independently hydrogen atom or fluorine atom.

[15] The compound according to any one of [1] to [14] or a pharmaceutically acceptable salt thereof, wherein the bond having a dashed line is a single bond.

[16] A compound selected from the group consisting of the following formulae:

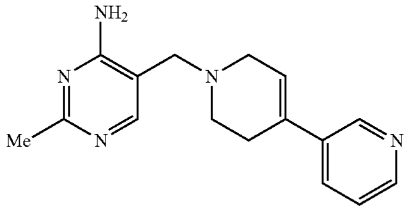

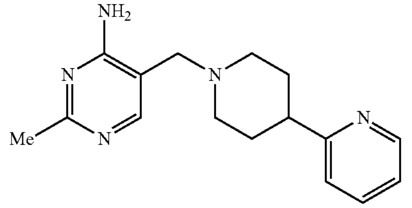

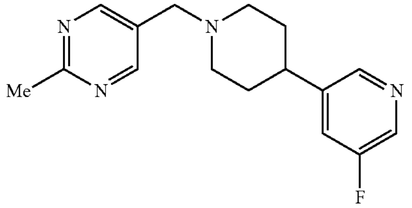

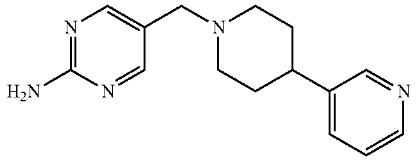

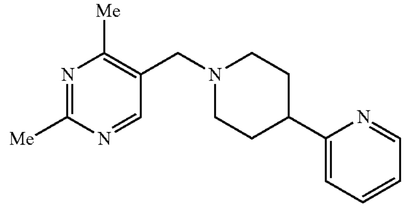

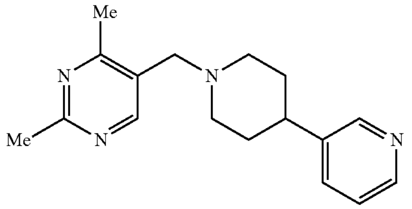

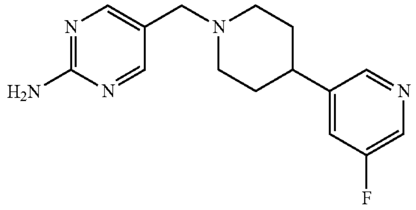

or a pharmaceutically acceptable salt thereof.

[17] A medicine comprising the compound according to any one of [1] to [16] or a pharmaceutically acceptable salt thereof as an active ingredient.

[18] A medicament for treating a central nervous system disease selected from the group consisting of attention deficit hyperactivity disorder, autistic spectrum disorder, schizophrenia, mood disorder, and cognitive dysfunction, comprising the compound according to any one of [1] to [16] or a pharmaceutically acceptable salt thereof as an active ingredient.

[19] A medicament for treating attention deficit hyperactivity disorder, comprising the compound according to any one of [1] to [16] or a pharmaceutically acceptable salt thereof as an active ingredient.

[20] The medicament according to [19], wherein the attention deficit hyperactivity disorder is a disorder with inattention as a predominant symptom.

[21] The medicament according to [19], wherein the attention deficit hyperactivity disorder is a disorder with hyperactivity as a predominant symptom.

[22] The medicament according to [19], wherein the attention deficit hyperactivity disorder is a disorder with impulsivity as a predominant symptom.

[23] A medicament for treating autistic spectrum disorder, comprising the compound according to any one of [1] to [16] or a pharmaceutically acceptable salt thereof as an active ingredient.

[24] The medicament according to [23], wherein the autistic spectrum disorder is a disorder with persistent deficits in social communication and social interaction as a predominant symptom.

[25] The medicament according to [23], wherein the autistic spectrum disorder is a disorder with restricted repetitive behaviors, interests or activities.

[26] A method for treating a central nervous system disease selected from the group consisting of attention deficit hyperactivity disorder, autistic spectrum disorder, schizophrenia, mood disorder, and cognitive dysfunction, which comprises administering a therapeutically effective amount of the compound according to any one of [1] to [16] or a pharmaceutically acceptable salt thereof to a patient in need thereof.

[27] Use of the compound according to any one of [1] to [16] or a pharmaceutically acceptable salt thereof in the manufacture of a medicament for treating a central nervous system disease selected from the group consisting of attention deficit hyperactivity disorder, autistic spectrum disorder, schizophrenia, mood disorder, and cognitive dysfunction.

[28] The compound according to any one of [1] to [16] or a pharmaceutically acceptable salt thereof for use in treating a central nervous system disease selected from the group consisting of attention deficit hyperactivity disorder, autistic spectrum disorder, schizophrenia, mood disorder, and cognitive dysfunction.

Effects of the Invention

The present compound exhibits selective and potent effects on dopamine $D_4$ receptors while exhibiting weak effects on the other GPCRs such as adrenergic $\alpha_{1A}$ and $\alpha_{2A}$ receptors. In addition, the present compound has high bioavailability after oral administration and good brain penetration, and is also at low risk for hepatotoxicity. Hence, the present compound is useful as a highly-safe and potent medicament for treating a central nervous system disease, which has no drug dependence and a reduced risk for cardiovascular side effects, and exhibits a fast-acting pharmaceutical effect in small amounts (e.g. a medicament for treating attention deficit hyperactivity disorder).

DESCRIPTION OF EMBODIMENTS

Figure 1:
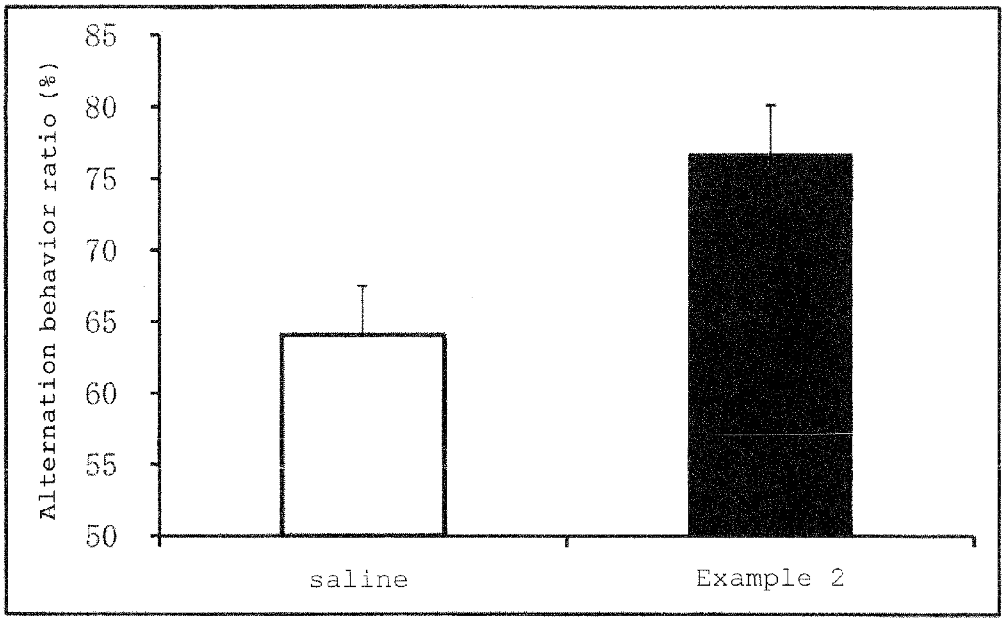
FIG. 1 is a bar graph showing the improvement alternation behavior ratio (%) with the administration of the compound of Example 2 in Test Example 7.

Hereinafter, the present invention is explained in detail. The number of carbon atoms in the definition of the "substituent" used herein may be expressed as, for example, the term "$C_{1-6}$". Specifically, the term "$C_{1-6}$ alkyl" is used for the same meaning as an alkyl group having 1 to 6 carbon atoms.

Specific examples of "halogen atom" used herein include fluorine atom, chlorine atom, bromine atom, and iodine atom.

The term "$C_{1-6}$ alkyl group" used herein means straight or branched, saturated hydrocarbon group having 1 to 6 carbon atoms. Preferred examples thereof include "$C_{1-4}$ alkyl group". Specific examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, and 2-ethylbutyl.

The term "$C_{3-6}$ cycloalkyl group" used herein means a 3- to 6-membered monocyclic saturated hydrocarbon group. Preferred examples thereof include "$C_{3-5}$ cycloalkyl group". Specific examples of the "$C_{3-6}$ cycloalkyl group" include cyclopropyl, cyclobutyl, cyclopentyl, and cyclohexyl.

The "$C_{1-6}$ alkyl" moiety of "$C_{1-6}$ alkoxy group" used herein has the same meaning as defined in the above "$C_{1-6}$ alkyl". Preferred examples thereof include "$C_{1-4}$ alkoxy group". Specific examples of the "$C_{1-6}$ alkoxy group" include methoxy, ethoxy, propoxy, isopropoxy, butoxy, isobutoxy, sec-butoxy, and tert-butoxy.

Examples of "5- to 10-membered nitrogen-containing heteroaryl group" used herein include 5- to 10-membered monocyclic or bicyclic, aromatic groups containing one to three nitrogen atoms. The group may further contain the same or different one or more heteroatoms selected from the group consisting of sulfur atom and oxygen atom. The group is preferably pyridyl group or isoquinolyl group, and more preferably, pyridyl group.

Specific examples of "5- to 10-membered nitrogen-containing heteroaryl group" used herein include groups of the following formulae:

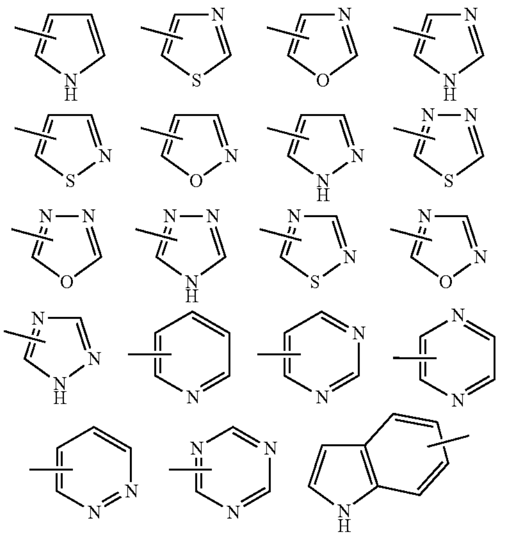

-continued

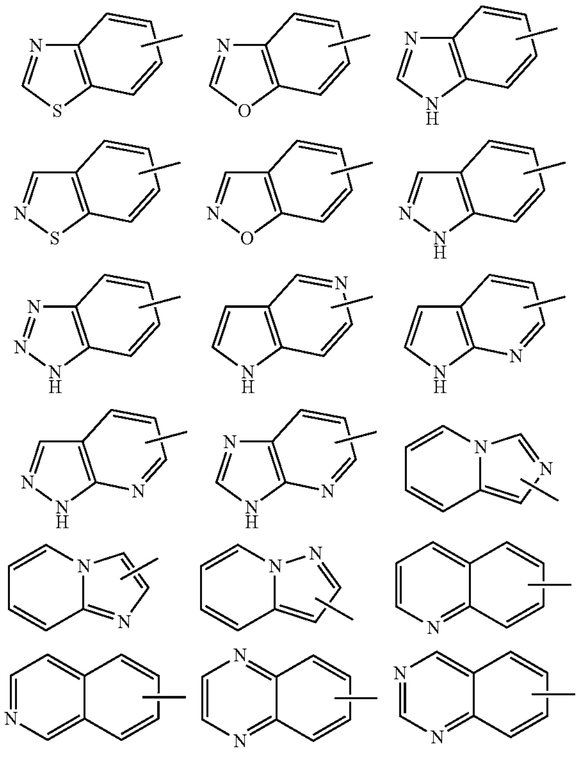

The bond(s) across a ring mean that "group(s)" are linked at any replaceable position(s) in the ring. For example, when a group is a heteroaryl group of the following formula:

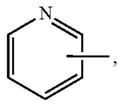, the group means 2-pyridyl group, 3-pyridyl group, or 4-pyridyl group.

Furthermore, when a "heteroaryl group" is a polycyclic group, for example, the following formula:

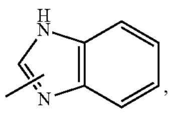, the group may be 1-benzimidazolyl, 2-benzimidazolyl, or 4-, 5-, 6- or 7-benzimidazolyl.

The definition "$R^{d1}$ and $R^{d2}$ may be combined with the carbon atom(s) to which they are attached to form a 3- to 8-membered cycloalkane ring or a 3- to 8-membered cycloalkene ring" used herein means that (1) $R^{d1}$ and $R^{d2}$ are combined with the same carbon atom in cyclic amino group to form a Spiro ring with the cyclic amino group; and (2) $R^{d1}$ and $R^{d2}$ are combined with the different carbon atoms in cyclic amino group to form a fused ring or a bicyclo ring with the cyclic amino group. Specific examples thereof include the following groups:

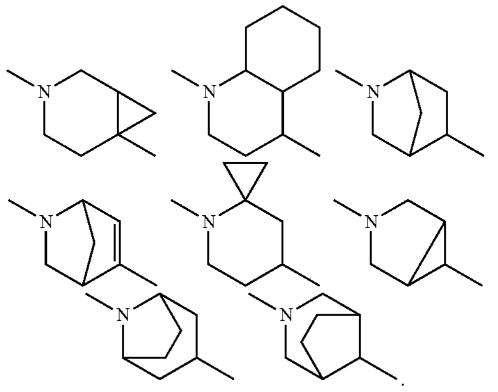

Examples of the substituent(s) in "optionally-substituted 5- to 10-membered nitrogen-containing heteroaryl group", "optionally-substituted pyridyl group", and "optionally-substituted isoquinolyl group" used herein include:

(1) halogen atom,
(2) $C_{1-6}$ alkyl group which may be optionally substituted with the same or different one to three halogen atoms,
(3) $C_{1-6}$ alkoxy group which may be optionally substituted with the same or different one to three halogen atoms,
(4) cyano group,
(5) amino group which may be optionally substituted with the same or different one or two groups selected independently from the group consisting of $C_{1-6}$ alkyl and $C_{3-7}$ cycloalkyl,
(6) hydroxy group,
(7) $C_{1-6}$ alkylcarbonyl group which may be optionally substituted with the same or different one to three halogen atoms,
(8) $C_{1-6}$ alkoxycarbonyl group which may be optionally substituted with the same or different one to three halogen atoms,
(9) aminocarbonyl group, wherein the amino moiety thereof may be optionally substituted with the same or different one or two groups selected independently from the group consisting of $C_{1-6}$ alkyl and $C_{3-7}$ cycloalkyl,
(10) $C_{1-6}$ alkylsulfonyl group which may be optionally substituted with the same or different one to three halogen atoms, and
(11) aminosulfonyl group, wherein the amino moiety thereof may be optionally substituted with the same or different one or two group selected independently from the group consisting of $C_{1-6}$ alkyl and $C_{3-7}$ cycloalkyl.

The substituent (s) are preferably halogen atom or $C_{1-6}$ alkyl group which may be optionally substituted with the same or different one to three halogen atoms, and more preferably fluorine atom.

"n and m" are independently 1 or 2; preferably, n is 1, and m is 1.

The term "bond having a dashed line" used herein is a single or double bond, and preferably a single bond.

The present compound may be in the forms of a hydrate and/or a solvate. Thus, the present compound also encompasses the hydrates and/or solvates such as ethanol solvate. Furthermore, the present compound also encompasses all types of crystal forms of the present compound.

Specific examples of the pharmaceutically acceptable salt of the compound of formula (1) include inorganic acid salts such as hydrochloride, hydrobromate, sulfate, phosphate, and nitrate; and organic acid salts such as formate, acetate, trifluoroacetate, propionate, oxalate, succinate, lactate, malate, tartrate, citrate, maleate, malonate, fumarate, methanesulfonate, p-toluenesulfonate, benzenesulfonate, and ascorbate.

The compound of formula (1) may be in the form of a tautomer. Thus, the present compound also encompasses tautomers of the compound of formula (1).

The compound of formula (1) may contain one or more asymmetric carbon atoms. Thus, the present compound encompasses not only racemic forms of the compound of formula (1) but also optically-active forms thereof. Also, the compound of formula (1) can result in various stereoisomerisms. Thus, the present compound also encompasses the stereoisomers of the compounds and mixtures thereof.

Also, the present compound encompasses the compound of formula (1) wherein one or more of $^{1}H$ are substituted with $^{2}H(D)$ (i.e. deuterated form).

Hereinafter, the process of preparing the present compound is illustrated with some examples, but the present invention should not be limited thereto. Also, some terms herein may be defined by the following abbreviations for the sake of simplicity.

Boc group: tert-butoxycarbonyl group

Cbz group: benzyloxycarbonyl group

Alloc group: allyloxycarbonyl group

Smoc group: 9-fluorenylmethyloxycarbonyl group

THF: tetrahydrofuran

DMF: N, N-dimethylformamide

In the following processes, besides the case where the use of protective groups is specified, any functional groups other than reaction sites may be optionally protected and then deprotected after the reaction or reactions are completed to give the desired compound when the functional groups can be changed under the reaction condition or can be inappropriate for carrying cut the reaction. The protective group includes any conventional groups described in various literatures, for example, T. W. Greene and P. G. M. Wuts, "Protective Groups in Organic Synthesis", 3rd Ed., John Wiley and Sons, inc., New York (1999). More specifically, specific examples of the protective groups for amino group include benzyloxycarbonyl, tert-butoxycarbonyl, acetyl and benzyl, and specific examples of the protective groups for hydroxy group include trialkylsilyl, acetyl, and benzyl.

The protecting groups can be introduced and deprotected according to commonly-used methods in synthetic organic chemistry (e.g. the method described in T. W. Greene and P. G. M. Nuts, "Protective Groups in Organic Synthesis", 3rd Ed., John Wiley and Sons, inc., New York (1999)) and similar methods thereto.

Preparation 1

The compound of formula (1) is prepared according to, for example, the following process.

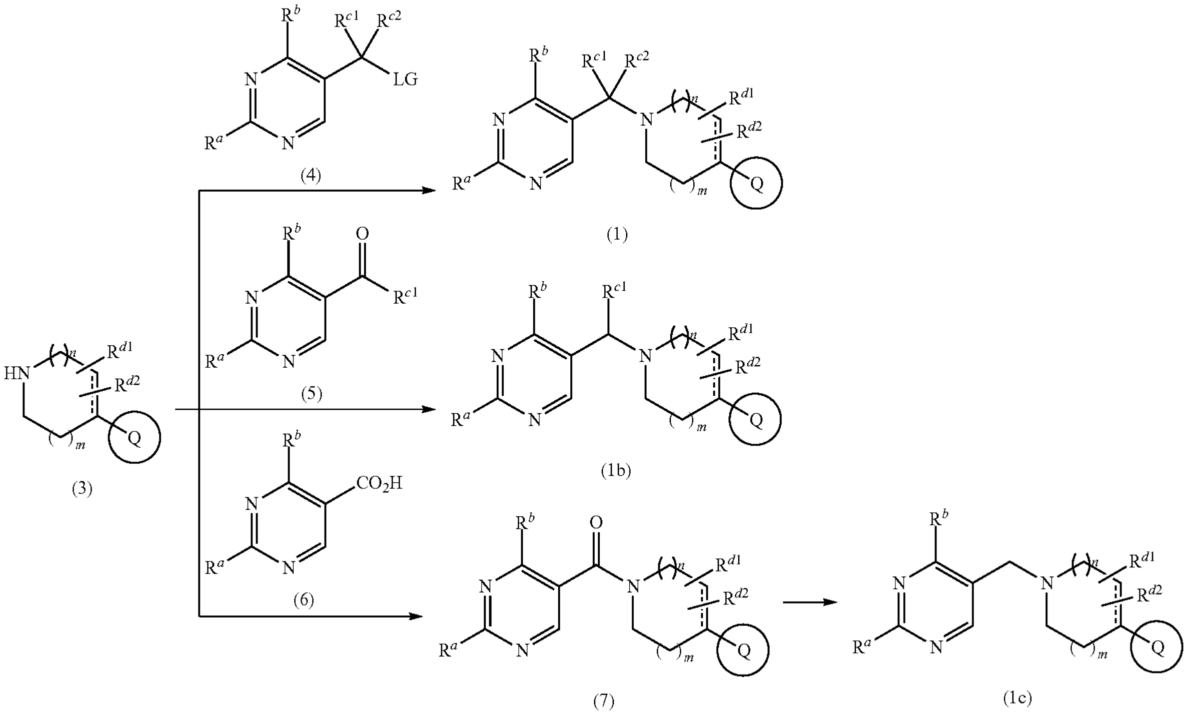

(4) (1) (5) (3) (1b) (6) (7) (1c)

PREPARATIONS

The present compound can be prepared according to, for example, the following processes of Preparations 1-3. The processes may be optionally modified by those skilled in the organic synthesis field. As appropriate, each compound used as a starting material may be used in the salt form.

wherein m, n, $R^a$, $R^b$, $R^{c1}$, $R^{c2}$, $R^{d1}$, $R^{d2}$, ring Q, and the bond having a dashed line are as defined in the above [1], and LG is a leaving group such as iodine atom, bromine atom, chlorine atom, and a substituted sulfonyl group (e.g. methanesulfonyl group and p-toluenesulfony group).

Compound (1) can be prepared by reacting compound (3) with compound (4) in an appropriate inert solvent. The reaction may be carried out in the presence of a base and/or a phase-transfer catalyst, as appropriate. The reaction temperature is typically a temperature of about −20° C. to the boiling point of the used solvent. The reaction time is typically in the range from 10 minutes to 48 hours, which may vary according to various conditions such as a reaction temperature, a base, a starting material, and a solvent to be used.

Specific examples of the base include organic bases such as triethylamine, diisopropylethylamine, and pyridine; inorganic bases such as potassium carbonate, sodium carbonate, cesium carbonate, potassium hydrogen carbonate, sodium hydrogen carbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydride; and metal alkoxides such as sodium methoxide and potassium tert-butoxide.

Specific examples of the phase-transfer catalyst include tetrabutylammonium hydrogen sulfate.

Specific examples of the inert solvent include halogenated hydrocarbons such as chloroform and dichloromethane; aromatic hydrocarbons such as benzene and toluene; ether-type solvents such as diethyl ether, tetrahydrofuran (THF), and 1,4-dioxane; lower alcohols such as methanol, ethanol, and 2-propanol; aprotic polar solvents such as acetonitrile, acetone, methyl ethyl ketone, dimethylformamide, N-methyl-2-pyrrolidinone, and dimethylsulfoxide; and mixtures thereof.

Among the compound of formula (1), the compound of formula (1b) can be prepared by the reductive amination of compound (3) and an aldehyde or ketone compound of formula (5) with a reducing agent in an appropriate inert solvent. The reaction may be carried out in the presence of a base or an acid, as appropriate. The reaction temperature is typically a temperature of about −20° C. to the boiling point of the used solvent. The reaction time is typically in the range from 10 minutes to 48 hours, which may vary according to various conditions such as a reaction temperature, a reducing agent, a starting material, and a solvent to be used.

Specific examples of the reducing agent include complex hydrides such as sodium triacetoxyborohydride, lithium aluminum hydride, sodium borohydride, and sodium cyanoborohydride; diborane; and borane complexes (e.g. borane-dimethylsulfide complex and borane-tetrahydrofuran complex).

Specific examples of the base include organic bases such as triethylamine, diisopropylethylamine, and pyridine; inorganic bases such as potassium carbonate, sodium carbonate, cesium carbonate, potassium hydrogen carbonate, sodium hydrogen carbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydrate; and metal alkoxides such as sodium methoxide and potassium tert-butoxide.

Specific examples of the acid include organic acids such as acetic acid, trifluoroacetic acid, and methanesulfonic acid, and inorganic acids such as hydrochloric acid and sulfuric acid.

Specific examples of the solvent include water; acetonitrile; halogenated hydrocarbons such as chloroform and dichloromethane; aromatic hydrocarbons such as benzene and toluene; ether-type solvents such as 1,2-dimethoxyethane, tetrahydrofuran, and 1,4-dioxane; alcohol-type solvents such as methanol, ethanol, and 2-propanol; aprotic polar solvents such as dimethylformamide and N-methyl-2-pyrrolidinone; and mixtures thereof.

Among the compound of formula (1), the compound of formula (1c) can be also prepared by reacting compound (7) with a reducing agent in an inert solvent. The reaction temperature is typically a temperature of about −20° C. to the boiling point of the used solvent. The reaction time is typically in the range from 10 minutes to 48 hours, which may vary according to various conditions such as a reaction temperature, a condensing agent, a starting material, and a solvent to be used. Specific examples of the reducing agent include lithium aluminum hydride and borane complexes (e.g. borane-dimethylsulfide complex and borane-tetrahydrofuran complex). Specific examples of the inert solvent include ether-type solvents such as tetrahydrofuran and 1,4-dioxane, and mixture thereof.

Compound (7) can be prepared by reacting compound (3) with the carboxylic acid of formula (6) in an inert solvent in the presence of a condensing agent. Furthermore, the reaction may be carried out in the presence of a base. The reaction temperature is typically a temperature of about −20° C. to the boiling point of the used solvent. The reaction time is typically in the range from 10 minutes to 48 hours, which may vary according to various conditions such as a reaction temperature, a condensing agent, a starting material, and a solvent to be used.

Compound (7) can be also prepared by reacting compound (3) with an acid halide or an acid anhydride derived from compound (6) in an inert solvent in the presence of a base. The reaction temperature is typically a temperature of about −20° C. to the boiling point of the used solvent. The reaction time is typically in the range from 10 minutes to 48 hours, which may vary according to various conditions such as a reaction temperature, a condensing agent, a starting material, and a solvent to be used.

Specific examples of the condensing agent include dicyclohexylcarbodiimide (DCC), diisopropylcarbodiimide (DIPC), 1-ethyl-3-(3-dimethylaminopropyl)-carbodiimide (WSC), benzotriazol-1-yl-tris(dimethylamino)phosphonium hexafluorophosphate (BOP), diphenylphosphonyldiamide (DPPA), N,N-carbonyldiimidazole (CDI), and benzotriazol-1-yl-N,N,N', N'-tetramethyluronium hexafluorophosphate (HBTU). As appropriate, the reaction may be carried out with the addition of an additive such as N-hydroxysuccinimide (HOSu), 1-hydroxybenzotriazole (HOBt), and 3-hydroxy-4-oxo-3,4-dihydro-1,2,3-benzotriazine (HOOBt).

Specific examples of the base include organic bases such as triethylamine, diisopropylethylamine, and pyridine; inorganic bases such as potassium carbonate, sodium carbonate, cesium carbonate, potassium hydrogen carbonate, sodium hydrogen carbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydride; and metal alkoxides such as sodium methoxide and potassium tert-butoxide.

Specific examples of the inert solvent include halogenated hydrocarbons such as chloroform and dichloromethane; aromatic hydrocarbons such as benzene and toluene; ether-type solvents such as diethyl ether, tetrahydrofuran (THF), and 1,4-dioxane; aprotic polar solvents such as acetonitrlle, acetone, methyl ethyl ketone, dimethylformamide, N-methyl-2-pyrrolidinone, and dimethylsulfoxide; basic solvents such as pyridine; or mixtures thereof.

Preparation 2

Among the compounds of formula (3), the compounds of formula (3a) and (3b) can be prepared according to, for example, the following process.

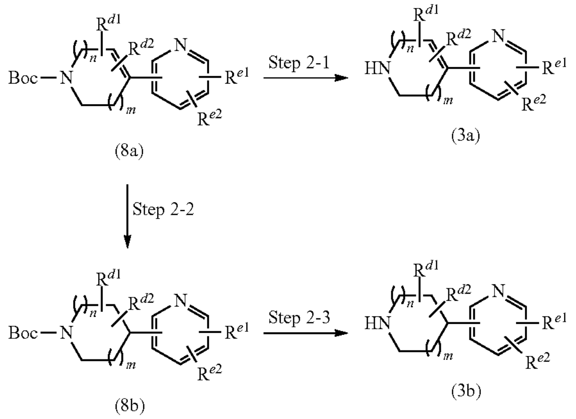

(8a) (3a) (8b) (3b)

wherein m, n, $R^{d1}$, $R^{d2}$, $R^{e1}$, and $R^{e2}$ are as defined in the above [1].

Compound (3a) can be prepared by treating compound (8a) with an acid (e.g. an inorganic acid such as hydrochloric acid and sulfuric acid, or an organic acid such as trifluoroacetic acid) in an appropriate inert solvent. The treatment temperature is typically a temperature of −20° C. to the boiling point of the used solvent. The reaction time is typically in the range from 10 minutes to 48 hours, which may vary according to various conditions such as a reaction temperature, an acid, a starting material, and a solvent to be used. Specific examples of the inert solvent include halogenated hydrocarbons such as chloroform and dichloromethane; aromatic hydrocarbons such as benzene and toluene; ether-type solvents such as diethyl ether, tetrahydrofuran, 1,4-dioxane, 1,2-dimethoxyethane; lower alcohols such as methanol, ethanol, and 2-propanol; aprotic polar solvents such as acetonitrile, dimethylformamide, N-methyl-2-pyrrolidinone, and dimethylsulfoxide; and mixtures thereof.

Compound (3b) can be prepared from compound (8b) according to a similar process to the above process of compound (3a).

Compound (8b) can be prepared by hydrogenating compound (8a) in an appropriate inert solvent under an ambient or high pressure hydrogen atmosphere. Specific examples of the catalyst used in the reductive reaction include palladium catalysts such as palladium carbon, rhodium catalysts such as rhodium carbon, platinum catalysts such as platinum carbon, and ruthenium catalysts such as ruthenium carbon. The reaction temperature is typically a temperature of 0° C. to 50° C. The reaction time is typically in the range from 10 minutes to 48 hours, which may vary according to various conditions such as a reaction temperature, a catalyst, a starting material, and a solvent to be used. Specific examples of the inert solvent include ester-type solvents such as ethyl acetate; aromatic hydrocarbons such as benzene and toluene; ether-type solvents such as diethyl ether, tetrahydrofuran, 1,4-dioxane, and 1,2-dimethoxyethane; alcohol-type solvents such as methanol, ethanol, and 2-propanol; aprotic polar solvents such as dimethylformamide, N-methyl-2-pyrrolidinone, and dimethylsulfoxide; and mixture thereof.

Other compounds of formula (3) are commercially available, or may be prepared according to well-known preparation processes or similar processes thereto.

Preparation 3

The compound of formula (8a) can be prepared according to, for example, the following process.

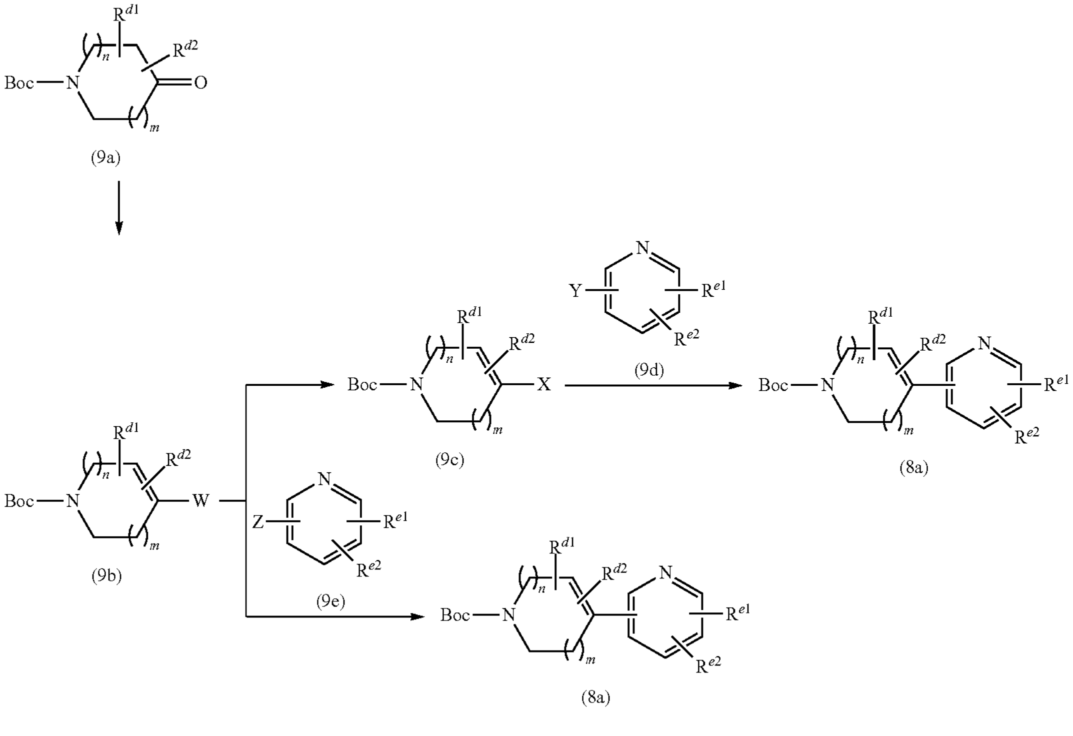

(9a) (9b) (9c) (9d) (9e) (8a) (8a)

wherein m, n, $R^{d1}$, $R^{d2}$, $R^{e1}$, and $R^{e2}$ are as defined in the above [1], W is a leaving group (e.g. a sulfonyloxy group such as trifluoromethanesulfonyloxy), X is a boronic acid group (—$B(OH)_2$) or a boronate group (e.g. pinacolboronate group), Y is a leaving group (e.g. a halogen atom such as chlorine atom, bromine atom and iodine atom, or a sulfonyloxy group such as trifluoromethanesulfonyloxy), Z is a boronic acid group (—$B(OH)_2$), a boronate group (e.g. pinacolboronate group), an organotin group (e.g. —Sn(n-$Bu)_4$), or an alkali earth metal for forming an organometallic pyridine compound (e.g. magnesium and zinc).

Compound (8a) can be prepared by the coupling reaction of compound (9c) with compound (9d) in an appropriate inert solvent in the presence of a transition metal catalyst. The reaction may be carried out in the presence of a ligand, a base, an additive, etc., as appropriate. The reaction temperature is typically a temperature of −10° C. to the boiling point of the used solvent. The reaction time is typically in the range from 10 minutes to 48 hours, which may vary according to various conditions such as a reaction temperature, a transition metal catalyst, a starting material, and a solvent to be used.

Specific examples of the transition metal catalyst include palladium (II) acetate, palladium (II) chloride, tris(dibenzylideneacetone)dipalladium (0), tetrakis(triphenylphosphine)palladium (0), bis(triphenylphosphine)palladium (II) chloride, dichlorobis(tri-O-tolylphosphine)palladium (II), bis(tri-tert-butylphosphine)palladium (0), and [1,1'-bis(diphenylphosphino)ferrocene]dichloropalladium (II).

Specific examples of the ligand include triphenylphosphine, tri-O-tolylphosphine, tri-tert-butylphosphine, tri-2-furylphosphine, tricyclohexylphosphine, triphenylarsine, 1,1'-bis(diphenylphosphino)ferrocene, 2-dicyclohexylphosphino-2',6'-dimethoxybiphenyl, and 2-dicyclohexylphosphino-2',4',6'-triisopropylbiphenyl.

Specific examples of the base include organic bases such as triethylamine and diisopropylethylamine; and inorganic bases such as sodium carbonate, sodium hydrogen carbonate, potassium carbonate, cesium carbonate, and potassium phosphate.

Specific examples of the additive include inorganic salts such as lithium chloride, cesium fluoride, copper (I) iodide, and copper (I) bromide.

Specific examples of the inert solvent include water, acetonitrile, as well as halogenated hydrocarbons such as chloroform and dichloromethane; aromatic hydrocarbons such as benzene and toluene; ether-type solvents such as 1,2-dimethoxyethane, tetrahydrofuran, and 1,4-dioxane; alcohol-type solvents such as methanol, ethanol, and 2-propanol; aprotic polar solvents such as dimethylformamide and N-methyl-2-pyrrolidinone; and mixtures thereof.

Compound (9c) can be prepared by the coupling reaction of compound (9b) with alkoxydiboron (e.g. bis(pinacolato) diboron) in an appropriate inert solvent in the presence of a transition metal catalyst. The reaction conditions are similar to those of the above coupling reaction of compound (9c) with compound (9d).

Compound (8a) can be also prepared by the coupling reaction of compound (9b) with compound (9e). The reaction conditions are similar to those of the above coupling reaction of compound (9c) with compound (9d).

Compound (9b) can be prepared by reacting compound (9a) with sulfonic acid anhydride (e.g. trifluoromethanesulfonic acid anhydride) or sulfonyl imide (e.g. N-phenylbis (trifluoromethanesulfonimide)) in an appropriate inert solvent in the presence of a base. The reaction temperature is typically a temperature of −20° C. to the boiling point of the used solvent. The reaction time is typically in the range from 10 minutes to 48 hours, which may vary according to various conditions such as a reaction temperature, a base, a starting material, and a solvent to be used.

Specific examples of the base include organic bases such as triethylamine, diisopropylethylamine, and pyridine; inorganic bases such as potassium carbonate, sodium carbonate, cesium carbonate, potassium hydrogen carbonate, sodium hydrogen carbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydroxide; and metal amides such as lithium diisopropylamide and lithium hexamethyldisilazide. Specific examples of the inert solvent include aromatic hydrocarbons such as benzene and toluene; ether-type solvents such as diethyl ether, tetrahydrofuran, 1,4-dioxane, and 1,2-dimethoxyethane; and mixtures thereof.

The compounds of formulae (4), (5), (6), (9a), (9d), and (9e) are commercially available, or may be prepared according to well-known processes or similar processes thereto.

The intermediates and desired compounds in the above preparation processes may be isolated and purified by conventional purification methods in organic synthetic chemistry such as neutralization, filtration, extraction, washing, drying, concentration, recrystallization, and each type of chromatography. The intermediates may be also used in the next reaction without any specific purification.

Optically-active products of the present invention can be prepared from an optically-active starting material or intermediate, or by the optical resolution of the racemate of a final product. The optical resolution method includes physical separation methods with optically-active column, and chemical separation methods such as a fractional crystallization method. A diastereomer of the present compound can be prepared by, for example, a fractional crystallization method.

The pharmaceutically acceptable salt of the compound of formula (1) can be prepared by, for example, mixing the compound of formula (1) with a pharmaceutical acceptable acid in a solvent such as water, methanol, ethanol, and acetone.

The present compound is a dopamine $D_4$ receptor agonist, and thus can be used for treating a disease such as a central nervous system disease with symptoms similar to ADHD, for example, autistic spectrum disorder (autistic spectrum disorder defined in Diagnostic and Statistical Manual of Mental Disorders, 5th Edition (DSM-V), which is classified as autism, Asperger's syndrome, atypical pervasive developmental disorder, and childhood disintegrative disorder in previous DSM-IV) as well as schizophrenia, mood disorder, and cognitive dysfunction with ADHD-like symptoms. The present compound may be used in combination with a central nervous system stimulant such as methylphenidate, a selective noradrenaline reuptake inhibitor such as atomoxetine, and each type of medicament for treating schizophrenia.

One of hypotheses implicated in the pathogenesis of autistic spectrum disorder is assumed to be a lack of the conformity in the network of nerves caused by the imbalance between excitatory and inhibitory neurotransmitters in the cerebral cortex. Then, it has been demonstrated that the imbalance can be improved by amplifying γ wave which is brain waves in high-frequency zone. Furthermore, it has been already reported that a dopamine $D_4$ receptor agonist can amplify γ wave in the cerebral cortex.

Also, it has been reported that oxytocin which is a hormone produced in the hypothalamus is involved in social cognition. That is, the reports suggest that oxytocin is associated with autism. Dopamine $D_4$ receptors are highly expressed in oxytocin-producing neurons which are expressed in hypothalamic paraventricular nuclei, and thus a dopamine $D_4$ receptor agonist is expected to enhance the release of oxytocin in the brain with the activation of oxytocin-producing neurons.

Accordingly, a dopamine $D_4$ receptor agonist can be used as a medicament for treating autistic spectrum disorder by the amplification of γ wave in the cerebral cortex, or the enhancement of the release of oxytocin in hypothalamus.

The present compound is preferably used for the treatment of ADHD and autistic spectrum disorder.

The present compound is preferably used for the treatment of ADHD, in particular, ADHD with inattention, hyperactivity, and impulsivity as predominant symptoms.

The present compound is preferably used for the treatment of autistic spectrum disorder, in particular, autistic spectrum disorder with persistent deficits in social communication and social interaction, and restricted repetitive behaviors, interests or activities as predominant symptoms.

It has been known that adrenergic $\alpha_{1A}$ receptors are distributed in the postsynaptic region of sympathetic nerve, and blood pressure is increased by the vasoconstrictive effect of an agonist thereof.

The present compound exhibits selective and potent effects on dopamine $D_4$ receptors while exhibiting weak effects on the other GPCRs such as adrenergic $\alpha_{1A}$ receptors. Hence, the present compound is expected to have a reduced risk for cardiovascular side effects, and exhibit high safety.

When a medicinal compound is taken into the body, the compound is metabolized to change its chemical structure, and is converted to a reactive intermediate, i.e. a reactive metabolite. The reactive metabolite may result in any toxicity (e.g. hepatotoxicity, allergy, tissue necrosis, mutagenicity, and carcinogenicity). As one of simple tests for evaluating toxic risks from the reactive metabolite, the glutathione (GSH) trapping test with dansyl glutathione (dGSH) may be used. In the test, when compounds with a high level of covalent binding to dGSH are exposed systemically, the above toxic risks are increased.

On the other hand, the present compound has an extremely low level of covalent binding to dGSH as shown in Test Example 5, and thus is at low risk for hepatotoxicity, etc. As a result, the present compound is expected to be administered safely over a long period.

The present compound may be administered orally or parenterally. The present compound may be orally-administered in the commonly-used dosage forms. The present compound may be parenterally-administered in the forms of a topical preparation, an injectable preparation, a transdermal preparation, and a transnasal preparation. Examples of the preparation for oral or rectal administration include a capsule, a tablet, a pill, a powder, a cachet, a suppository, and a solution. Examples of the injectable preparation include a sterile solution and a suspension. Examples of the topical preparation include a cream, an ointment, a lotion, and a transdermal preparation (e.g. a conventional patch and a matrix).

The above dosage forms can be formulated using a pharmaceutically acceptable excipient and additive in conventional manners. Examples of the pharmaceutically acceptable excipient and additive include a carrier, a binder, a perfume, a buffer, a thickener, a colorant a stabilizer, an emulsifier, a dispersant, a suspending agent, and a preservative agent.

Examples of the pharmaceutically acceptable carrier include magnesium carbonate, magnesium stearate, talc, sucrose, lactose, pectin, dextrin, starch, gelatin, tragacanth, methylcellulose, sodium carboxymethyl cellulose, low-melting-point wax, and cacao butter. The capsule may be formulated by filling a capsule with the present compound together with a pharmaceutically acceptable carrier. The present compound may be mixed with a pharmaceutically acceptable excipient or without any excipient to be put into a capsule. The cachet may be also formulated in similar manners.

Examples of the injectable solution include solution, a suspension, and an emulsion. For example, examples thereof include an aqueous solution and a water-propylene glycol solution. The solution may contain water, and may be also prepared in the form of a polyethylene glycol solution and/or a propylene glycol solution. The solution suitable for oral administration can be prepared by adding the present compound to water together with a colorant, a perfume, a stabilizing agent, a sweetening agent, a solubilizer, and a thickener, as appropriate. The solution suitable for oral administration can be also prepared by adding the present compound to water together with a dispersant to thicken the solution. Examples of the thickener include pharmaceutically acceptable natural or synthetic gum, resin, methylcellulose, sodium carboxymethyl cellulose, and known suspending agents.

The dosage of the present compound may vary according to various conditions such as patient's disease, age, body weight, sex, symptom, and administration route. Typically, the present compound is administered to an adult (body weight: 50 kg) at a dose of 0.1 to 1000 mg/day, preferably at a dose of 0.1 to 300 mg/day, which may be administered once a day or 2 or 3 times a day. In addition, the present compound may be administered once in several days to several weeks.

EXAMPLES

Hereinafter, the present invention is illustrated in more detail with Reference Examples, Examples, and Test Examples, but the present invention should not be limited thereto. The compound names as shown in the following Reference Examples and Examples do not necessarily follow the IUPAC nomenclature system. Also, some abbreviations may be used herein for the sake of simplicity, and the abbreviations are as defined above.

The compound identification was performed with any methods such as proton nuclear magnetic resonance absorption spectrum ($^1$H-NMR) and LC-MS. Amino column chromatography in Reference Examples and Examples was performed with the amino column manufactured by Yamazen Corporation. LC-MS measurement was performed under various conditions as shown in Table 1 below. Retention Time (R.T.) means the time when the mass spectral peak of a sample is detected in the LC-MS measurement.

TABLE 1

| | Condition A | Condition B |
|---|---|---|
| analyser | Shimadzu LCMS-2010EV | Shimadzu LCMS-2020 |
| column | Shiseido CAPCELL PAR C18 MG II (4.6 mm × 50 mm) | Phenomenex Kinetex 1.7 μm C18 (50 mm × 2.10 mm) |
| solvent | A solution: MeOH, B solution: 0.05% TFA/$H_2O$ | A solution: MeOH, B solution: 0.05% TFA/$H_2O$ |
| gradient condition | 0.0-1.0 min; A/B = 30:70<br>1.0-7.0 min; A/B = 99:1<br>7.1-12.0 min; A/B = 30:70 | 0.0 min; A/B = 30:70<br>0.0-1.90 min; A/B = 99:1<br>1.91-3.00 min; A/B = 30:70 |
| flow rate | 2.8 mL/min | 0.5 mL/min |
| UV | 220 nm | 220 nm |
| column temperature | 40° C. | 40° C. |

The differential scanning calorimetry (DSC) was performed with TA Instrument Q1000 (temperature rising rate: 10° C./min). The thermogravimetric analysis (TGA) was performed with TA Instrument Q500 (temperature rising rate: 10° C./min).

The acceptable range of the extrapolated onset temperature (Tim) in the differential scanning calorimetry (DSC) is ±5° C.

The following abbreviations may be used herein. Also, the following abbreviations are used in NMR data in Reference Examples as well as Examples.

Me group: methyl group

Et group: ethyl group

Boc group: tert-butoxycarbonyl group tert-: tertiarys: singlet brs: broad singlet d: doublet t: triplet m: multiplet br: broad J: coupling constant Hz: Hertz $CDCl_3$: deuterochloroform DMSO-$d_6$: deuterodimethylsulfoxide Example 1

5-(3',6'-Dihydro-2,4'-bipyridin-1'(2'H)-ylmethyl)-2-methylpyrimidin-4-amine

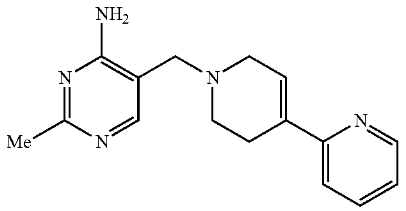 [SMILES: Cc1ncc(CN2CC=C(c3ccccn3)CC2)c(N)n1]

To a solution of the compound of Reference Example 1 (180 mg, 0.773 mmol) in dimethylformamide (3.0 mL) were added potassium carbonate (534 mg, 3.87 mmol) and 5-(chloromethyl)-2-methylpyrimidin-4-amine hydrochloride (150 mg, 0.773 mmol). The mixture was stirred at room temperature for 15 hours, then water (30 mL) was added thereto, and the mixture was extracted with ethyl acetate (20 mL) six times. The combined organic layer was dried over anhydrous sodium sulfate, filtrated, and concentrated. The resulting residue was purified by silica gel column chromatography (chloroform:methanol=100:0 to 5:5), and then by amino column chromatography (n-hexane:ethyl acetate=57:43 to 12:88). To the resulting purified product was added ethyl acetate (0.5 mL), the mixture was stirred at room temperature for 30 minutes, and n-hexane (1.5 mL) was added thereto. The mixture was stirred at room temperature for additional 30 minutes, and the precipitate was collected on a filter to give the title compound (107 mg, 49%).

$^1$H-NMR (300 MHz, $CDCl_3$) δ: 2.50 (3H, s), 2.76-2.62 (4H, m), 3.22-3.14 (2H, m), 3.57 (2H, s), 6.63 (1H, brs), 7.18-7.13 (1H, m), 7.37 (1H, brd, J=7.9 Hz), 7.65 (1H, ddd, J=7.9, 1.8, 1.8 Hz), 7.97 (1H, s), 8.56 (1H, brd, J=5.0 Hz).

Example 2

5-(3',6'-Dihydro-3,4'-bipyridin-1'(2'H)-ylmethyl)-2-methylpyrimidin-4-amine

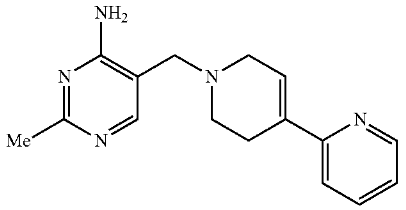 [SMILES: Cc1ncc(CN2CC=C(c3ccccn3)CC2)c(N)n1]

To a solution of the compound of Reference Example 2 (20 g, 85.8 mmol) in dichloromethane (420 mL) was added triethylamine (27.5 ml, 197 mmol) under ice cooling, the mixture was stirred at room temperature for 20 minutes, and the compound of Reference Example 21 (12.9 g, 94.4 mmol) and sodium triacetoxyborohydride (27.3 g, 129 mmol) were added thereto under ice cooling. The mixture was stirred at room temperature for 1.5 hours, then sodium triacetoxyborohydride (18.2 g, 85.8 mmol) was added thereto under ice cooling, and the mixture was stirred at room temperature for additional 20 hours. To the reaction mixture was then added 10% aqueous potassium carbonate solution (420 mL) under ice cooling, the organic layer was separated, and the water layer was further extracted with chloroform (100 mL) twice. The organic layers were combined, dried over anhydrous sodium sulfate, filtered, and concentrated. The resulting residue was purified by silica gel column chromatography (chloroform:methanol=100:0 to 97:3) to give the title compound (19.7 g, 82%).

$^1$H-NMR (300 MHz, $CDCl_3$) δ: 2.51 (3H, s), 2.61-2.52 (2H, m), 2.72 (2H, t, J=5.7 Hz), 3.16 (2H, dd, J=2.9, 2.9 Hz), 3.56 (2H, s), 6.16-6.10 (1H, m), 7.28-7.22 (1H, m), 7.65 (1H, ddd, J=8.1, 2.0, 2.0 Hz), 7.98 (1H, s), 8.49 (1H, dd, J=4.8, 1.7 Hz), 8.66 (1H, brd, J=2.0 Hz).

Example 3

5-(3-Fluoro-3',6'-dihydro-2,4'-bipyridin-1'(2'H)-ylmethyl)-2-methylpyrimidin-4-amine

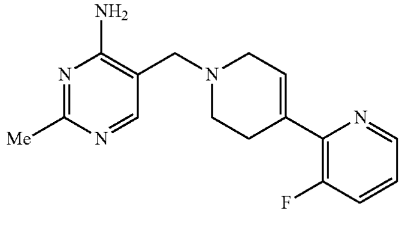 [SMILES: Cc1ncc(CN2CC=C(c3ncccc3F)CC2)c(N)n1]

To a solution of the compound of Reference Example 7 (50 mg, 0.199 mmol) in dichloromethane (1.5 mL) was added triethylamine (0.0554 mL, 0.398 mmol), the mixture was stirred at room temperature for 10 minutes, and the compound of Reference Example 21 (30 mg, 0.219 mmol) and sodium triacetoxyborohydride (63.3 mg, 0.299 mmol)

were added thereto. The mixture was stirred at room temperature for 1 hour, then sodium triacetoxyborohydride (42.2 mg, 0.199 mmol) was added thereto, and the mixture was stirred at room temperature for additional 3 hours. To the reaction mixture was then added saturated aqueous sodium hydrogen carbonate solution (20 mL), and the mixture extracted with chloroform (20 mL) twice. The combined organic layer was dried over anhydrous sodium sulfate, filtered, and concentrated. The resulting residue was purified by silica gel column chromatography (chloroform: methanol=100:0 to 97:3) to give the title compound (45.0 mg, 76%).

$^1$H-NMR (300 MHz, $CDCl_3$) δ: 2.50 (3H, s), 2.77-2.67 (4H, m), 3.23-3.16 (2H, m), 3.57 (2H, s), 6.57-6.52 (1H, m), 7.20-7.13 (1H, m), 7.38 (1H, ddd, J=11.6, 8.3, 1.5 Hz), 7.97 (1H, s), 8.38 (1H, ddd, J=3.1, 1.5, 1.5 Hz).

Example 4

5-(5-Fluoro-3',6'-dihydro-3,4'-bipyridin-1'(2'H)-ylmethyl)-2-methylpyrimidin-4-amine

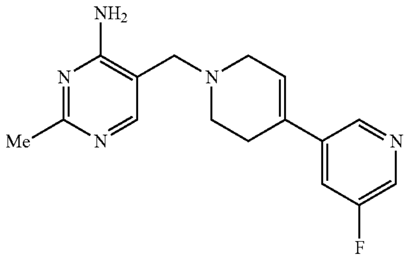 [SMILES: Cc1ncc(CN2CC=C(c3cncc(F)c3)CC2)c(N)n1]

The title compound was prepared from the compound of Reference Example 13 according to a similar process to that of Example 3 (yield: 59%).

$^1$H-NMR (300 MHz, $CDCl_3$) δ: 2.50 (3H, s), 2.52-2.58 (2H, m), 2.72 (2H, t, J=5.7 Hz), 3.13-3.19 (2H, m), 3.56 (2H, s), 6.15-6.21 (1H, m), 7.33-7.39 (1H, m), 7.98 (1H, s), 8.36 (1H, brd, J=2.6 Hz), 8.48 (1H, brs).

Example 5

2-Methyl-5-[4-(pyridin-2-yl)piperidin-1-ylmethyl]pyrimidin-4-amine

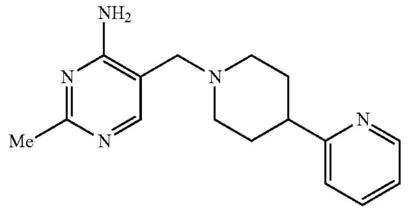 [SMILES: Cc1ncc(CN2CCC(c3ccccn3)CC2)c(N)n1]

The title compound was prepared from the compound of Reference Example 3 according to a similar process to that of Example 1 (yield: 80%).

$^1$H-NMR (300 MHz, $CDCl_3$) δ: 1.77-2.00 (4H, m), 2.11 (2H, td, J=11.6, 2.5 Hz), 2.49 (3H, s), 2.66-2.78 (1H, m), 2.93-3.04 (2H, m), 3.46 (2H, s), 7.10-7.19 (2H, m), 7.62 (1H, ddd, J=7.7, 7.7, 1.8 Hz), 7.93 (1H, s), 8.53-8.57 (1H, m). Extrapolated onset temperature: 134° C. to 135° C.

Example 6

2-Methyl-5-[4-(pyridin-3-yl)piperidin-1-ylmethyl]pyrimidin-4-amine

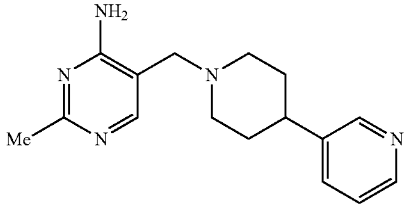 [SMILES: Cc1ncc(CN2CCC(c3cccnc3)CC2)c(N)n1]

The title compound was prepared from the compound of Reference Example 11 according to a similar process to that of Example 1 (yield: 80%).

$^1$H-NMR (300 MHz, $CDCl_3$) δ: 1.77-2.00 (4H, m), 2.11 (2H, td, J=11.6, 2.5 Hz), 2.49 (3H, s), 2.66-2.78 (1H, m), 2.93-3.04 (2H, m), 3.46 (2H, s), 7.10-7.19 (2H, m), 7.62 (1H, ddd, J=7.7, 7.7, 1.8 Hz), 7.93 (1H, s), 8.53-8.57 (1H, m).

Example 7

5-[4-(5-Fluoropyridin-3-yl)piperidin-1-ylmethyl]-2-methylpyrimidin-4-amine

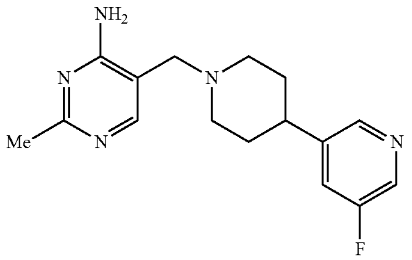 [SMILES: Cc1ncc(CN2CCC(c3cncc(F)c3)CC2)c(N)n1]

To a solution of the compound of Reference Example 13 (60 mg, 0.24 mmol) in methanol (2 mL) was added 10% palladium/carbon (25 mg), and the mixture was stirred under hydrogen atmosphere at room temperature for 1 hour. The mixture was then filtrated through Celite®, and concentrated. The resulting concentrated residue was dissolved in dichloromethane (3 mL), and triethylamine (0.067 mL, 0.48 mmol) was added thereto. The mixture was stirred at room temperature for 10 minutes, then the compound of Reference Example 21 (33 mg, 0.24 mmol) and sodium triacetoxyborohydride (76 mg, 0.36 mmol) were added thereto, and the mixture was stirred at room temperature for 3 hours. To reaction mixture was then added saturated aqueous sodium hydrogen carbonate solution (20 mL), and the mixture was extracted with chloroform (20 mL) twice. The combined organic layer was dried over anhydrous sodium sulfate, filtrated, and concentrated. The resulting residue was purified by amino column chromatography (ethyl acetate: hexane=50:50) to give the title compound (25 mg, 34%).

$^1$H-NMR (400 MHz, $CDCl_3$) δ: 1.65-1.76 (m, 2H), 1.89-1.93 (m, 2H), 2.08-2.15 (m, 2H), 2.50 (s, 3H), 2.60-2.68 (m, 1H), 3.00 (d, J=11.7 Hz, 2H), 3.46 (s, 2H), 7.24-7.28 (m, 1H), 7.95 (s, 1H), 8.32-8.33 (m, 2H).

Example 8

5-[4-(Isoquinolin-1-yl)piperidin-1-yl]methyl]-2-methylpyrimidin-4-amine

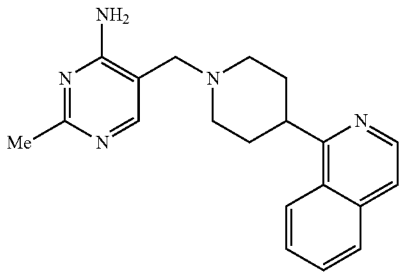 [SMILES: Cc1ncc(CN2CCC(c3nccc4ccccc34)CC2)c(N)n1]

To a solution of the compound of Reference Example 15 (285 mg, 1.0 mmol) in acetonitrile (5.0 mL) were added potassium carbonate (415 mg, 3.0 mmol), potassium iodide (199 mg, 1.2 mmol), and 5-(chloromethyl)-2-methylpyrimidin-4-amine hydrochloride (233 mg, 1.2 mmol). The reaction mixture was stirred at 60° C. for 18 hours, filtered, and concentrated. The resulting residue was purified by preparative high-performance liquid chromatography to give the title compound (30.0 mg, 9%).

$^1$H-NMR (400 MHz, $CD_3OD$) δ: 1.85-1.95 (2H, m), 2.05-2.17 (2H, m), 2.23-2.34 (2H, m), 2.42 (3H, s), 2.96-3.06 (2H, m), 3.53 (2H, s), 3.65-3.75 (1H, m), 7.64 (1H, d, J=6.0 Hz), 7.65-7.71 (1H, m), 7.72-7.78 (1H, m), 7.87-7.94 (2H, m), 8.30-8.38 (2H, m).

Example 9

5-[4-(Isoquinolin-3-yl)piperidin-1-ylmethyl]-2-methylpyrimidin-4-amine

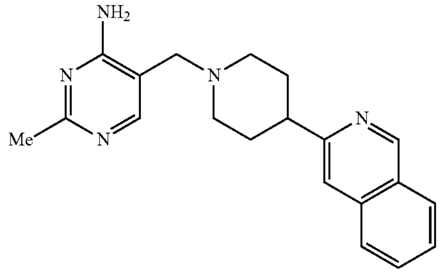 [SMILES: Cc1ncc(CN2CCC(c3cc4ccccc4cn3)CC2)c(N)n1]

The title compound was prepared from the compound of Reference Example 18 according to a similar process to that of Example 8 (yield: 7.5%).

$^1$H-NMR (400 MHz, $CD_3OD$) δ: 1.91-2.12 (2H, m), 2.32-2.43 (2H, m), 2.48 (3H, s), 2.86-3.00 (1H, m), 3.08-3.17 (2H, m), 3.65 (2H, s), 7.65 (1H, dd, J=7.2, 7.2 Hz), 7.68 (1H, s), 7.76 (1H, dd, J=7.4, 7.4 Hz), 7.90 (1H, d, J=8.4 Hz), 8.00 (1H, s), 8.06 (1H, d, J=8.0 Hz), 9.18 (1H, s).

Example 10

5-(3',6'-Dihydro-2,4'-bipyridin-1'(2'H)-ylmethyl)-2-ethylpyrimidin-4-amine

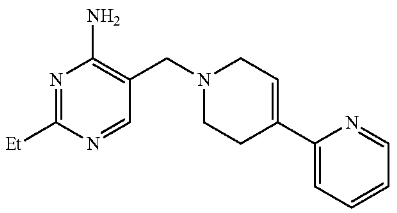 [SMILES: CCc1ncc(CN2CC=C(c3ccccn3)CC2)c(N)n1]

To a solution of the compound of Reference Example 1 (233 mg, 1.0 mmol) in methanol (3.0 mL) were added the compound of Reference Example 23 (151 mg, 1.0 mmol) and sodium cyanoborohydride (126 mg, 2.0 mmol). The reaction mixture was stirred at 45° C. for 16 hours, and purified by preparative high-performance liquid chromatography to give the title compound (53.2 mg, 18%).

$^1$H-NMR (400 MHz, $CDCl_3$) δ: 1.32 (3H, t, J=7.6 Hz), 2.64-2.81 (6H, m), 3.16-3.24 (2H, m), 3.57 (2H, s), 6.60-6.66 (1H, m), 7.15 (1H, dd, J=6.8, 5.2 Hz), 7.37 (1H, d, J=8.0 Hz), 7.65 (1H, dd, J=7.6, 6.0 Hz), 8.01 (1H, s), 8.56 (1H, d, J=3.6 Hz).

Examples 11-28

The compounds of Examples 11-28 were synthesized from the compounds of the corresponding Reference Examples according to the process of Example 10.

| Examples | Chemical Structure | Instrumental Analysis Data |
|---|---|---|
| 11 | 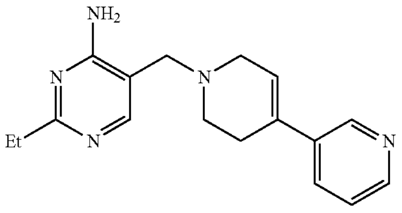 [SMILES: CCc1ncc(CN2CC=C(c3cccnc3)CC2)c(N)n1] | $^1$H-NMR (400 MHz, $CDCl_3$) δ: 1.30 (3H, t, J = 8.0 Hz), 2.50-2.59 (2H, m), 2.66-2.83 (4H, m), 3.10-3.18 (2H, m), 3.55 (2H, s), 6.08-6.15 (1H, m), 7.24 (1H, dd, J = 8.0, 4.8 Hz), 7.60-7.68 (1H, m), 8.00 (1H, s), 8.45-8.53 (1H, m), 8.64 (1H, d, J = 2.0 Hz) . |

-continued

| Examples | Chemical Structure | Instrumental Analysis Data |
| --- | --- | --- |
| 12 | 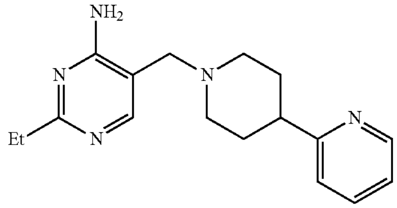 [SMILES: CCc1ncc(CN2CCC(c3ccccn3)CC2)c(N)n1] | $^1$H-NMR (400 MHz, $CDCl_3$) δ: 1.31 (3H, t, J = 8.0 Hz) , 1.78-2.00 (4H, m), 2.06-2.17 (2H, m), 2.67-2.79 (3H, m), 2.94-3.03 (2 H, m) , 3.46 (2H, s), 7.08-7.22 (2H, m), 7.62 (1H, dd, J = 9.6, 8.0 Hz), 7.96 (1H, s), 8.55 (1H, d, J = 4.4 Hz). |
| 13 | 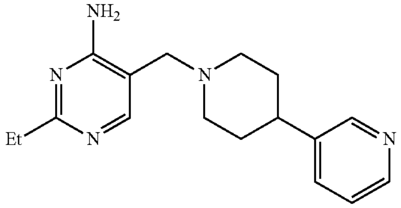 [SMILES: CCc1ncc(CN2CCC(c3cccnc3)CC2)c(N)n1] | $^1$H-NMR (400 MHz, $CDCl_3$) δ: 1.31 (3H, t, J = 7.6 Hz), 1.64-1.83 (2H, m), 1.86-1.94 (2H, m), 2.06-2.17 (2H, m), 2.56-2.64 (1 H, m), 2.74 (2H, q, J = 7.6 Hz), 2.94-3.04 (2H, m), 3.46 (2H, s), 7.23 (1H, dd, J = 8.0, 4.8 Hz), 7.52 (1H, d, J = 8.0 Hz), 7.97 (1H, s), 8.46 (1H, d, J = 3.6 Hz), 8.49 (1H, d, J = 2.0 Hz). |
| 14 | 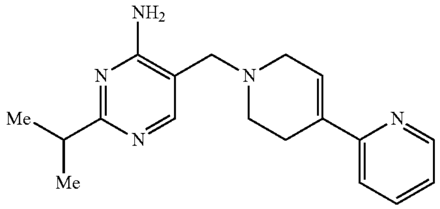 [SMILES: CC(C)c1ncc(CN2CC=C(c3ccccn3)CC2)c(N)n1] | $^1$H-NMR (400 MHz, $CDCl_3$) δ: 1.32 (6H, d, J = 7.2 Hz), 2.66-2.80 (4H, m), 2.93-3.03 (1H, m), 3.16-3.25 (2H, m), 3.59 (2H, s), 6.63-6.70 (1H, m), 7.17 (1H, dd, J = 7.6, 5.2 Hz), 7.39 (1H, d, J = 8.0 Hz), 7.67 (1H, dd, J = 7.6, 6.0 Hz), 8.04 (1H, s), 8.59 (1H, d, J = 4.0 Hz). |
| 15 | 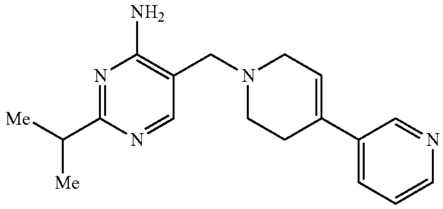 [SMILES: CC(C)c1ncc(CN2CC=C(c3cccnc3)CC2)c(N)n1] | $^1$H-NMR (400 MHz, $CDCl_3$) δ: 1.29 (6H, d, J = 7.2 Hz) , 2.50-2.61 (2H, m), 2.67-2.78 (2H, m), 2.91-3.03 (1H, m), 3.11-3.22 (2 H, m), 3.56 (2H, s), 6.10-6.17 (1H, m), 7.21-7.31 (1H, m), 7.65 (1H, d, J = 8.0 Hz), 8.02 (1H, s), 8.49 (1H, d, J = 4.8 Hz), 8.65 (1H, d, J = 2.0 Hz). |
| 16 | 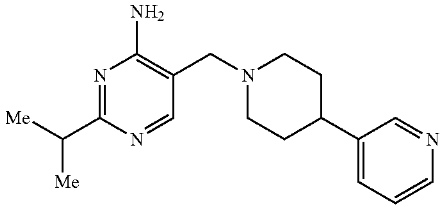 [SMILES: CC(C)c1ncc(CN2CCC(c3cccnc3)CC2)c(N)n1] | $^1$H-NMR (400 MHz, $CDCl_3$) δ: 1.29 (6H, d, J = 7.2 Hz), 1.66-1.79 (2H, m), 1.84-1.93 (2H, m), 2.05-2.16 (2H, m), 2.53-2.63 (1 H, m), 2.89-3.05 (3H, m), 3.46 (2H, s), 7.23 (1H, dd, J = 8.4, 4.8 Hz), 7.52 (1H, d, J = 8.0 Hz), 7.99 (1H, s), 8.46 (1H, dd, J = 4.8, 1.2 Hz), 8.50 (1H, d, J = 1.6 Hz). |
| 17 | 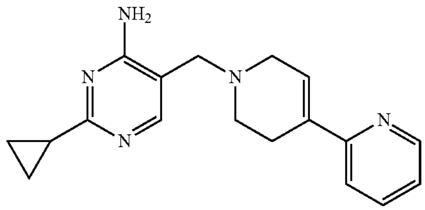 [SMILES: Nc1nc(C2CC2)ncc1CN1CC=C(c2ccccn2)CC1] | $^1$H-NMR (400 MHz, $CD_3OD$) δ: 0.95-1.05 (2H, m), 1.05-1.11 (2H, m), 1.93-2.04 (1H, m), 2.63-2.73 (2 H, m), 2.73-2.80 (2H, m), 3.18-3.25 (2H, m), 3.60 (2H, s), 6.56-6.63 (1H, m), 7.28 (1H, dd, J = 7.2, 4.8 Hz), 7.56 (1H, d, J = 8.4 Hz), 7.80 (1H, dd, J = 9.6, 8.0 Hz), 7.90 (1H, s), 8.49 (1H, d, J = 4.4 Hz) . |

-continued

| Examples | Chemical Structure | Instrumental Analysis Data |
|---|---|---|
| 18 | 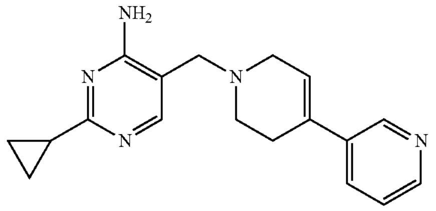 [SMILES: Nc1nc(C2CC2)ncc1CN1CC=C(c2cccnc2)CC1] | $^1$H-NMR (400 MHz, $CD_3OD$) δ: 1.08-1.21 (4H, m), 1.97-2.08 (1H, m), 2.60-2.68 (2H, m), 2.76-2.85 (2 H, m), 3.20-3.25 (2H, m), 3.64 (2H, s), 6.25-6.30 (1H, m), 7.43 (1H, dd, J = 8.0, 4.8 Hz), 7.91 (1H, d, J = 8.4 Hz), 7.96 (1H, s), 8.43 (1H, d, J = 4.4 Hz), 8.62 (1H, brs). |
| 19 | 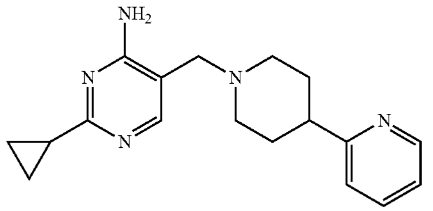 [SMILES: Nc1nc(C2CC2)ncc1CN1CCC(c2ccccn2)CC1] | $^1$H-NMR (400 MHz, $CD_3OD$) δ: 1.03-1.15 (4H, m), 1.83-2.05 (5H, m), 2.25-2.75 (2H, m), 2.74-2.85 (1 H, m), 3.03-3.13 (2H, m), 3.59 (2H, s), 7.28 (1H, dd J = 5.2, 5.2 Hz), 7.37 (1H, d, J = 8.0 Hz), 7.79 (1H, dd, J = 8.0, 8.0 Hz), 7.91 (1H, s), 8.47 (1H, d, J = 4.4 Hz). |
| 20 | 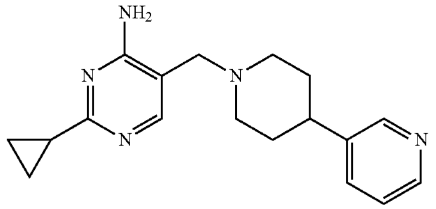 [SMILES: Nc1nc(C2CC2)ncc1CN1CCC(c2cccnc2)CC1] | $^1$H-NMR (400 MHz, $CDCl_3$) δ: 0.91-1.03 (2H, m), 1.04-1.12 (2H, m), 1.65-1.80 (2H, m), 1.84-1.98 (2 H, m), 1.98-2.07 (1H, m), 2.07-2.18 (2H, m), 2.55-2.65 (1H, m), 2.95-3.05 (2H, m), 3.45 (2H, s), 7.25 (1H, dd, J = 7.6, 4.8 Hz), 7.54 (1H, dd, J = 8.0, 2.0 Hz), 7.91 (1H, s), 8.49 (1H, dd, J = 1.6, 1.6 Hz), 8.51 (1H, d, J = 2.0 Hz). |
| 21 | 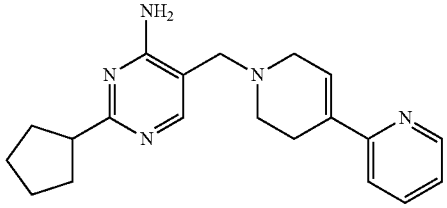 [SMILES: Nc1nc(C2CCCC2)ncc1CN1CC=C(c2ccccn2)CC1] | $^1$H-NMR (400 MHz, $CDCl_3$) δ: 1.63-1.75 (2H, m), 1.78-1.98 (4H, m), 2.00-2.13 (2H, m), 2.65-2.79 (4 H, m), 3.06-3.20 (1H, m), 3.20-3.25 (2H, m), 3.5-(2H, s), 6.61-6.69 (1H, m), 7.17 (1H, dd, J = 6.8, 6.8 Hz), 7.39 (1H, d, J = 8.0 Hz), 7.66 (1H, dd, J = 8.0, 1.6 Hz), 8.03 (1H, s), 8.58 (1H, d, J = 4.4 Hz). |
| 22 | 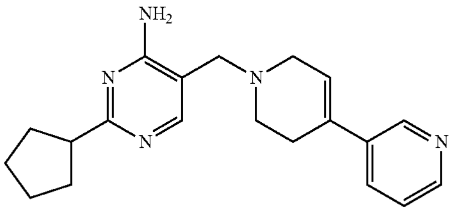 [SMILES: Nc1nc(C2CCCC2)ncc1CN1CC=C(c2cccnc2)CC1] | $^1$H-NMR (400 MHz, $CDCl_3$) δ: 1.58-1.75 (2H, m), 1.75-1.94 (4H, m), 1.95-2.10 (2H, m), 2.50-2.60 (2 H, m), 2.66-2.75 (2H, m), 3.03-3.20 (3H, m), 3.55 (2H, s), 6.10-6.18 (1H, m), 7.22-7.30 (1H, m), 7.65 (1H, d, J = 8.0 Hz), 8.01 (1H, s), 8.49 (1H, d, J = 4.0 Hz), 8.66 (1H, d, J = 1.6 Hz). |
| 23 | 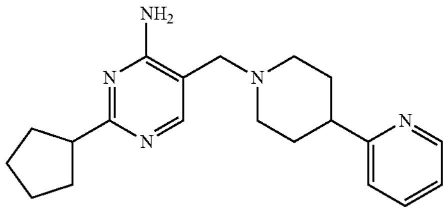 [SMILES: Nc1nc(C2CCCC2)ncc1CN1CCC(c2ccccn2)CC1] | $^1$H-NMR (400 MHz, $CDCl_3$) δ: 1.61-1.75 (2H, m), 1.78-2.00 (8H, m), 2.00-2.19 (4H, m), 2.69-2.81 (1 H, m), 3.00-3.06 (2H, m), 3.06-3.19 (1H, m), 3.47 (2H, s), 7.11-7.22 (2H, m), 7.64 (1H, dd, J = 9.6, 8.0 Hz), 7.99 (1H, s), 8.57 (1H, d, J = 4.4 Hz). |

-continued

| Examples | Chemical Structure | Instrumental Analysis Data |
|---|---|---|
| 24 | 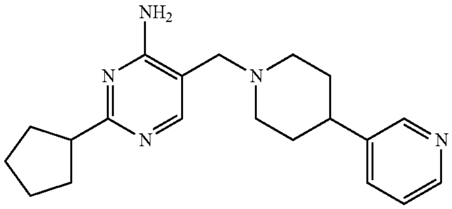 [SMILES: Nc1nc(C2CCCC2)ncc1CN1CCC(c2cccnc2)CC1] | $^1$H-NMR (400 MHz, $CDCl_3$) δ: 1.88-2.03 (9H, m), 2.05-2.20 (3H, m), 2.20-2.43 (2H, m), 2.58-2.70 (1 H, m), 2.96-3.13 (2H, m), 3.26-3.40 (1H, m), 3.62 (2H, s), 7.22-7.35 (1H, m), 7.54 (1H, d, J = 8.4 Hz), 8.10 (1H, s), 8.45-8.58 (2H, m). |
| 25 | 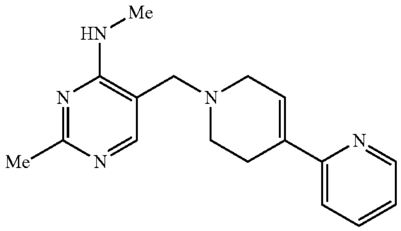 [SMILES: CNc1nc(C)ncc1CN1CC=C(c2ccccn2)CC1] | $^1$H-NMR (400 MHz, $CDCl_3$) δ: 2.53 (3H, s), 2.60-2.73 (4H, m), 2.93 (3H, d, J = 5.2 Hz), 3.13-3.20 (2H, m), 3.52 (2H, s), 6.62-6.69 (1H, m), 7.16 (1H, dd, J = 7.2, 4.8 Hz), 7.39 (1H, d, J = 8.0 Hz), 7.66 (1H, dd, J = 9.2, 7.6 Hz), 7.84 (1H, s), 8.58 (1H, d, J = 4.0 Hz). |
| 26 | 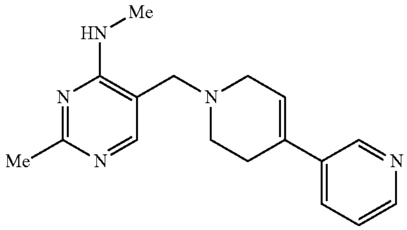 [SMILES: CNc1nc(C)ncc1CN1CC=C(c2cccnc2)CC1] | $^1$H-NMR (400 MHz, $CDCl_3$) δ: 2.47-2.57 (5H, m), 2.66 (2H, t, J = 5.6 Hz), 2.99 (3H, d, J = 4.8 Hz), 3.08-3.16 (2H, m), 3.49 (2H, s), 6.08-6.16 (1H, m), 7.16 (1H, brs), 7.25 (1H, dd, J = 8.4, 5.2 Hz), 7.66 (1H, d, J = 8.0 Hz), 7.82 (1H, s), 8.47 (1H, d, J = 4.4 Hz), 8.65 (1H, d, J = 1.6 Hz). |
| 27 | 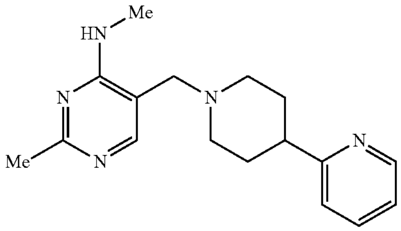 [SMILES: CNc1nc(C)ncc1CN1CCC(c2ccccn2)CC1] | $^1$H-NMR (400 MHz, $CDCl_3$) δ: 1.76-2.00 (4H, m), 2.03-2.14 (2H, m), 2.52 (3H, s), 2.65-2.77 (1H, m), 2.91-3.00 (2H, m), 3.02 (3H, d, J = 4.8 Hz), 3.40 (2H, s), 7.10-7.20 (2H, m), 7.27 (1H, brs), 7.62 (1H, dd, J = 9.6, 7.6 Hz), 7.80 (1H, s), 8.56 (1H, d, J = 4.0 Hz). |
| 28 | 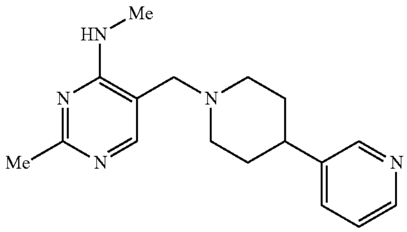 [SMILES: CNc1nc(C)ncc1CN1CCC(c2cccnc2)CC1] | $^1$H-NMR (400 MHz, $CDCl_3$) δ: 1.63-1.78 (2H, m), 1.85-1.95 (2H, m), 2.04-2.13 (2H, m), 2.52 (3H, s), 2.53-2.65 (1H, m), 2.93-3.03 (2H, m), 3.04 (3H, d, J = 4.8 Hz), 3.41 (2H, s), 7.21-7.25 (2H, m), 7.54 (1H, d, J = 8.0 Hz) , 7.81 (1H, s), 8.47 (1H, dd, J = 3.2, 3.2 Hz), 8.51 (1 H, d, J = 2.0 Hz). |

Example 29

1'-[(2-Methylpyrimidin-5-yl)methyl]-1',2',3',6'-tetrahydro-2,4'-bipyridine

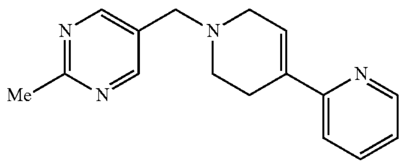 [SMILES: Cc1ncc(CN2CC=C(c3ccccn3)CC2)cn1]

To a solution of the compound of Reference Example 1 (30 mg, 0.129 mmol) in dimethylformamide (1.5 mL) were added potassium carbonate (89.1 mg, 0.645 mmol) and 5-(chloromethyl)-2-methylpyrimidine (18.3 mg, 0.129 mmol). The reaction mixture was stirred at room temperature for 15 hours, and purified by silica gel column chromatography (chloroform: methanol 100:0 to 95:5) to give the title compound (8.6 mg, 25%).

$^1$H-NMR (300 MHz, $CDCl_3$) δ: 2.64-2.72 (2H, m), 2.72-2.75 (2H, m), 2.75 (3H, s), 3.22-3.28 (2H, m), 3.63 (2H, s), 6.59-6.64 (1H, m), 7.14 (1H, ddd, J=7.5, 4.8, 1.1 Hz), 7.35-7.39 (1H, m), 7.64 (1H, ddd, 3=7.8, 7.8, 1.8 Hz), 8.54-8.58 (1H, m), 8.65 (2H, s).

Examples 30-32

The compounds of Examples 30-32 were synthesized from the compounds of the corresponding Reference Examples according to the process of Example 29.

| Examples | Chemical Structure | Instrumental Analysis Data |
|---|---|---|
| 30 | 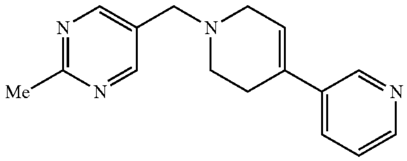 [SMILES: Cc1ncc(CN2CC=C(c3cccnc3)CC2)cn1] | $^1$H-NMR (300 MHz, $CDCl_3$) δ: 2.53-2.60 (2H, m), 2.74 (2H, t, J = 6.0 Hz), 2.75 (3H, s), 3.21 (2H, dd, J = 2.9, 2.9 Hz), 3.62 (2H, s), 6.10-6.14 (1H, m), 7.24 (1H, ddd, J = 7.9, 4.7, 0.9 Hz), 7.65 (1H, ddd, J = 8.0, 2.3, 1.7 Hz), 8.48 (1H, dd, J = 4.8, 1.5 Hz), 8.64 (2H, s), 8.65-8.66 (1H, m). |
| 31 | 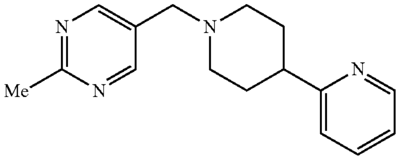 | $^1$H-NMR (300 MHz, $CDCl_3$) δ: 1.76-2.01 (4H, m), 2.16 (2H, td, J = 11.5, 2.6 Hz), 2.66-2.80 (1H, m), 2.74 (3H, s), 2.94-3.04 (2 H, m), 3.51 (2H, s), 7.12 (1H, ddd, J = 7.4, 4.9, 1.0 Hz), 7.15-7.20 (1H, m), 7.62 (1H, ddd, J = 7.7, 7.7, 1.8 Hz), 8.51-8.56 (1H, m), 8.61 (2H, s). |
| 32 | 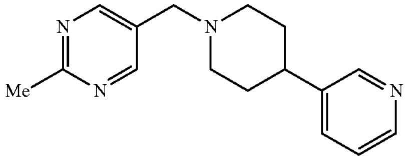 [SMILES: Cc1ncc(CN2CCC(c3cccnc3)CC2)cn1] | $^1$H-NMR (300 MHz, $CDCl_3$) δ: 1.71-1.89 (4H, m), 2.15 (2H, td, J = 11.4, 3.1 Hz), 2.48-2.62 (1H, m), 2.74 (3H, s), 2.94-3.03 (2 H, m), 3.52 (2H, s), 7.23 (1H, ddd, J = 7.9, 4.9, 0.6 Hz), 7.50-7.56 (1H, m), 8.45 (1H, dd, J = 4.9, 1.6 Hz), 8.49 (1H, d, J = 2.2 Hz), 8.61 (2H, s). |

Example 33

5-[4-(5-Fluoropyridin-3-yl)piperidin-1-ylmethyl]-2-methylpyrimidine

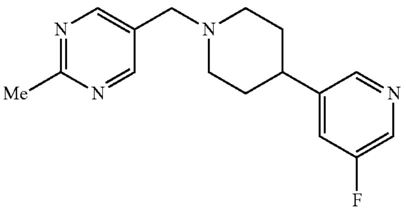 [SMILES: Cc1ncc(CN2CCC(c3cncc(F)c3)CC2)cn1]

The title compound was prepared from the compound of Reference Example 13 according to a similar process to that of Example 7 (yield: 34%).

$^1$H-NMR (400 MHz, $CDCl_3$) δ: 1.72-1.90 (m, 4H), 2.15 (t, J=11.7 Hz, 2H), 2.58-2.66 (m, 1H), 2.74 (s, 3H), 3.00 (d, J=11.2 Hz, 2H), 3.53 (s, 2H), 7.25-7.30 (m, 1H), 8.32 (s, 2H), 8.61 (s, 2H).

Example 34

5-(3',6'-Dihydro-2,4'-bipyridin-1'(2'H)-ylmethyl) pyrimidin-2-amine

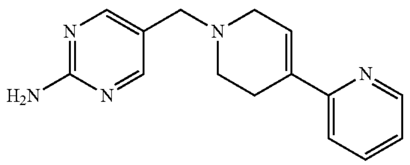 [SMILES: Nc1ncc(CN2CC=C(c3ccccn3)CC2)cn1]

To a solution of the compound of Reference Example 1 (30 mg, 0.129 mmol) in dichloromethane (1.5 mL) was added triethylamine (0.036 mL, 0.258 mmol), the mixture was stirred at room temperature for 10 minutes, and then 2-aminopyrimidine-5-carboxyaldehyde (15.9 mg, 0.129 mmol) and sodium triacetoxyborohydride (41.0 mg, 0.194 mmol) were added thereto. The mixture was stirred at room temperature for 1.5 hours, then sodium triacetoxyborohydride (41.0 mg, 0.194 mmol) was added thereto, and the mixture was stirred at room temperature for additional 24 hours. To the reaction mixture was then added saturated aqueous sodium hydrogen carbonate solution (20 mL), and the mixture was extracted with chloroform (20 mL) twice. The combined organic layer was dried over anhydrous sodium sulfate, filtrated, and concentrated. The resulting residue was purified by silica gel column chromatography (chloroform:methanol=100:0 to 90:10) to give the title compound (20.1 mg, 58%).

$^1$H-NMR (400 MHz, $CDCl_3$) δ: 2.65-2.70 (2H, m), 2.71-2.75 (2H, m), 3.20-3.24 (2H, m), 3.50 (2H, s), 4.99 (2H, brs), 6.60-6.64 (1H, m), 7.13 (1H, ddd, J=7.4, 4.8, 1.0 Hz), 7.37 (1H, d, J=8.0 Hz), 7.63 (1H, ddd, J=7.7, 7.7, 1.8 Hz), 8.30 (2H, s), 8.54-8.57 (1H, m).

Examples 35-37

The compounds of Examples 35-37 were synthesized from the compounds of the corresponding Reference Examples according to the process of Example 34.

| Examples | Chemical Structure | Instrumental Analysis Data |
|---|---|---|
| 35 | 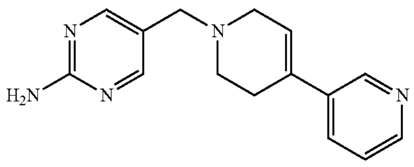 [SMILES: Nc1ncc(CN2CC=C(c3cccnc3)CC2)cn1] | $^1$H-NMR (400 MHz, $CDCl_3$) δ: 2.53-2.59 (2H, m), 2.72 (2H, t, J = 5.6 Hz), 3.19 (2H, dd, J = 3.0, 3.0 Hz), 3.49 (2H, s), 5.00 (2H, brs), 6.10-6.15 (1H, m), 7.24 (1H, ddd, J = 8.0, 4.8, 0.9 Hz), 7.65 (1H, ddd, J = 8.0, 2.4, 1.6 Hz), 8.30 (2H, s), 8.48 (1H, dd, J = 4.8, 1.6 Hz), 8.65 (1 H, dd, J = 2.4, 0.7 Hz). |
| 36 | 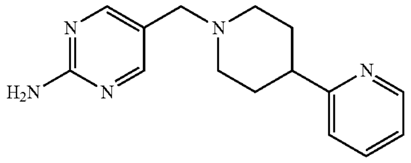 | $^1$H-NMR (400 MHz, $CDCl_3$) δ: 1.83 (2H, ddd, J = 24.6, 12.1, 3.7 Hz), 1.91-1.98 (2H, m), 2.11 (2H, td, J = 11.8, 2.5 Hz), 2.67-2.76 (1H, m), 2.97-3.03 (2 H, m), 3.39 (2H, s), 4.96 (2H, brs), 7.11 (1H, ddd, J = 7.4, 4.9, 1.1 Hz), 7.16-7.19 (1H, m), 7.61 (1H, ddd, J = 7.7, 7.7, 1.9 H z), 8.27 (2H, s), 8.51-8.54 (1H, m). |
| 37 | 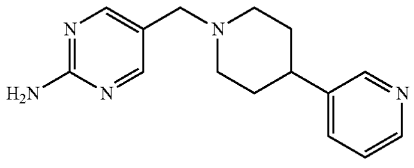 [SMILES: Nc1ncc(CN2CCC(c3cccnc3)CC2)cn1] | $^1$H-NMR (400 MHz, $CDCl_3$) δ: 1.70-1.89 (4H, m), 2.09 (2H, td, J = 11.5, 2.9 Hz), 2.49-2.59 (1H, m), 2.97-3.04 (2H, m), 3.40 (2 H, s), 4.98 (2H, brs), 7.22 (1H, dd, J = 7.2, 4.8 Hz), 7.51-7.55 (1H, m), 8.26 (2H, s), 8.45 (1H, dd, J = 4.8, 1.6 Hz), 8.49 (1H, d, J = 2.2 Hz). |

Example 38

2-Methyl-5-[2-methyl-4-(pyridin-2-yl)piperidin-1-ylmethyl]pyrimidin-4-amine

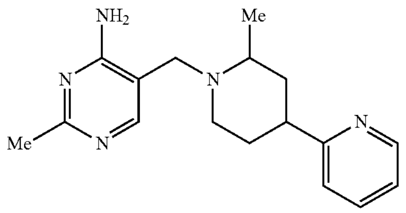 [SMILES: Cc1ncc(CN2CCC(c3ccccn3)CC2C)c(N)n1]

To a solution of the compound of Reference Example 35 (150 mg, 0.60 mmol) in dichloromethane (3 mL) was added triethylamine (0.192 mL, 1.38 mmol), the mixture was stirred at room temperature for 5 minutes, and then the compound of Reference Example 21 (91.0 mg, 0.66 mmol) and sodium triacetoxyborohydride (190 mg, 0.90 mmol) were added thereto. The mixture was stirred at room temperature for 7 hours, then saturated aqueous sodium hydrogen carbonate solution was added thereto, and the mixture was extracted with ethyl acetate. The organic layer was washed with saturated aqueous sodium chloride solution, dried over anhydrous sodium sulfate, filtrated, and concentrated. The resulting residue was purified by amino column chromatography (hexane:ethyl acetate=1:1). To a solution of the purified product in methanol (3 mL) was then added 10% palladium/carbon (30 mg), and the mixture was stirred under hydrogen atmosphere at room temperature. After 4 hours, the mixture was filtrated through Celite®, and concentrated. The resulting residue was purified by silica gel column chromatography (chloroform:methanol=10:1) to give the title compound (57%).

$^1$H-NMR (400 MHz, $CDCl_3$) δ: 1.12, 1.28 (d, J=6.0 Hz, 3H, diastereo ratio=1:4), 1.64-2.38 (m, 5H), 2.49 (s, 3H), 2.63-2.93 (m, 3H), 3.57 (s, 2H), 7.11-7.17 (m, 2H), 7.59-7.64 (m, 1H), 7.93, 7.94 (s, 1H, diastereo ratio=4:1), 8.54-8.55 (m, 1H).

LC-MS: condition A R.T.=0.6 min ObsMS=298.1 [M+1]

Example 39

2-Methyl-5-[2-methyl-4-(pyridin-3-yl)piperidin-1-ylmethyl]pyrimidin-4-amine

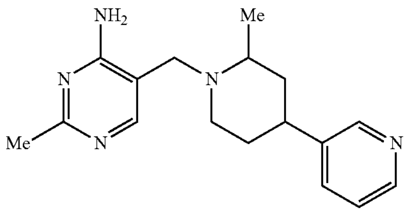 [SMILES: Cc1ncc(CN2CCC(c3cccnc3)CC2C)c(N)n1]

To a solution of the compound of Reference Example 39 (52.0 mg, 0.21 mmol) in dichloromethane (2 mL) was added triethylamine (0.064 mL, 0.46 mmol), the mixture was stirred at room temperature for 5 minutes, and then the compound of Reference Example 21 (32.0 mg, 0.23 mmol) and sodium triacetoxyborohydride (67.0 mg, 0.32 mmol) were added thereto. The mixture was stirred at room temperature for 6 hours, then saturated aqueous sodium hydrogen carbonate solution was added thereto, and the mixture was extracted with ethyl acetate. The organic layer was washed with saturated aqueous sodium chloride solution, dried over anhydrous sodium sulfate, filtrated, and concentrated. The resulting residue was purified by silica gel column chromatography (chloroform:methanol=10:1) to give the title compound (10%).

$^1$H-NMR (400 MHz, $CDCl_3$) δ: 1.12, 1.29 (d, J=6.3 Hz, 3H, diastereo ratio=3:1), 1.60-2.00 (m, 5H), 3.42 (s, 3H), 2.63-2.66 (m, 1H), 2.85-3.17 (m, 2H), 3.57 (s, 2H), 7.24 (dd, J=7.6, 5.1 Hz, 1H), 7.52-7.54 (m, 1H), 7.94, 7.95 (s, 1H, diastereo ratio=1:3), 8.45-8.50 (m, 2H).

LC-MS: condition A R.T.=1.1 min ObsMS=298.1 [M+1]

Example 40

2-Methyl-5-[3-methyl-4-(pyridin-2-yl)piperidin-1-ylmethyl]pyrimidin-4-amine

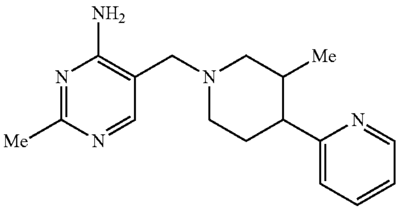 [SMILES: Cc1ncc(CN2CCC(c3ccccn3)C(C)C2)c(N)n1]

To a solution of the compound of Reference Example 42 (172 mg, 0.69 mmol) in dichloromethane (3 mL) was added triethylamine (0.221 mL, 1.6 mmol), the mixture was stirred at room temperature for 5 minutes, and then the compound of Reference Example 21 (105 mg, 0.76 mmol) and sodium triacetoxyborohydride (219 mg, 1.04 mmol) were added thereto. The mixture was stirred at room temperature for 6 hours, then saturated aqueous sodium hydrogen carbonate solution was added thereto, and the mixture was extracted with ethyl acetate. The organic layer was washed with saturated aqueous sodium chloride solution, dried over anhydrous sodium sulfate, filtrated, and concentrated. The resulting residue was purified by amino column chromatography (hexane:ethyl acetate=1:1). To a solution of the purified product (143 mg, 0.48 mmol) in methanol (5 mL) was then added 10% palladium/carbon (80 mg), and the mixture was stirred under hydrogen atmosphere at room temperature. After 4 hours, the mixture was filtrated through Celite®, and concentrated. The resulting residue was purified by silica gel column chromatography (chloroform: methanol=10:1) to give the title compound (70%). LC-MS: condition A R.T.=1.2 min ObsMS=298.2 [M+1]

Example 41

2-Methyl-5-[3-methyl-4-(pyridin-3-yl)piperidin-1-ylmethyl]pyrimidin-4-amine

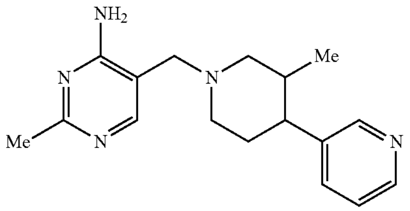 [SMILES: Cc1ncc(CN2CCC(c3cccnc3)C(C)C2)c(N)n1]

To a solution of the compound of Reference Example 46 (110 mg, 0.44 mmol) in dichloromethane (3 mL) was added triethylamine (0.123 mL, 1.88 mmol), the mixture was stirred at room temperature for 5 minutes, and then the compound of Reference Example 21 (60.0 mg, 0.44 mmol) and sodium triacetoxyborohydride (140 mg, 0.66 mmol) were added thereto. The mixture was stirred at room temperature for 6 hours, then saturated aqueous sodium hydrogen carbonate solution was added thereto, and the mixture was extracted with ethyl acetate. The organic layer was washed with saturated aqueous sodium chloride solution, dried over anhydrous sodium sulfate, filtrated, and concentrated. The resulting residue was purified by amino column chromatography (hexane:ethyl acetate=1:1) to give the title compound (20%).

$^1$H-NMR ($CDCl_3$) δ: 0.79 (d, J=7.1 Hz, 3H), 2.05-2.35 (m, 5H), 2.49 (s, 3H), 2.78-3.04 (m, 3H), 3.36-3.46 (m, 2H), 7.24 (dd, J=7.3, 4.9 Hz, 1H), 7.45-7.50 (m, 1H), 7.94 (s, 1H), 8.45-8.50 (m, 2H).

LC-MS: condition A R.T.=1.2 min ObsMS=298.1 [M+1]

Example 42

2-Methyl-5-[4-(pyridin-2-yl)azepan-1-ylmethyl]pyrimidin-4-amine

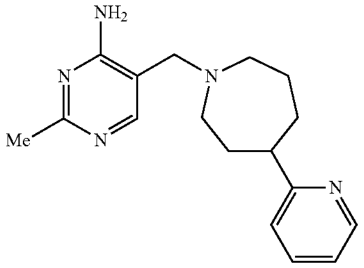 [SMILES: Cc1ncc(CN2CCCC(c3ccccn3)CC2)c(N)n1]

To a solution of the compound of Reference Example 49 (8.0 mg, 0.03 mmol) in dichloromethane (2 mL) was added triethylamine (0.010 mL, 0.07 mmol), the mixture was stirred at room temperature for 5 minutes, and then the compound of Reference Example 21 (4.0 mg, 0.03 mmol) and sodium triacetoxyborohydride (10 mg, 0.05 mmol) were added thereto. The mixture was stirred at room temperature for 4 hours, then saturated aqueous sodium hydrogen carbonate solution was added thereto, and the mixture was extracted with ethyl acetate. The organic layer was washed with saturated aqueous sodium chloride solution, dried over anhydrous sodium sulfate, filtrated, and concentrated. The resulting residue was purified by amino column chromatography (chloroform:methanol=1:1). To a solution of the purified product (3.0 mg, 0.03 mmol) in methanol (2 mL) was then added 10% palladium/carbon (3.0 mg), and the mixture was stirred under hydrogen atmosphere at room temperature. After 3 hours, the mixture was filtrated through Celite®, and concentrated. The resulting residue was purified by silica gel column chromatography (chloroform: methanol=10:1) to give the title compound (66%).

$^1$H-NMR (400 MHz, $CDCl_3$) δ: 1.78-2.02 (m, 6H), 2.49 (s, 3H), 2.64-2.82 (m, 4H), 2.93-3.01 (m, 1H), 3.70-3.76 (m, 2H), 7.09-7.13 (m, 2H), 7.56-7.62 (m, 2H), 8.14 (s, 1H), 8.52 (d, J=4.9 Hz, 1H).

LC-MS: condition A R.T.=1.1 min ObsMS=298.1 [M+1]

Example 43

2-Methyl-5-[4-(pyridin-3-yl)azepan-1-ylmethyl]pyrimidin-4-amine

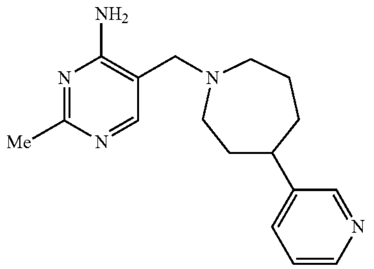 [SMILES: Cc1ncc(CN2CCCC(c3cccnc3)CC2)c(N)n1]

To a solution of the compound of Reference Example 53 (47 mg, 0.19 mmol) in dichloromethane (2 mL) was added triethylamine (0.061 mL, 0.44 mmol), the mixture was stirred at room temperature for 5 minutes, and then the compound of Reference Example 21 (29 mg, 0.21 mmol) and sodium triacetoxyborohydride (60 mg, 0.29 mmol) were added thereto. The mixture was stirred at room temperature for 6 hours, then saturated aqueous sodium hydrogen carbonate solution was added thereto, and the mixture was extracted with ethyl acetate. The organic layer was washed with saturated aqueous sodium chloride solution, dried over anhydrous sodium sulfate, filtrated, and concentrated. The resulting residue was purified by silica gel column chromatography (chloroform:methanol=1:1). To a solution of the purified product (8.0 mg, 0.03 mmol) in methanol (2 mL) was then added 10% palladium/carbon (20 mg), and the mixture was stirred under hydrogen atmosphere at room temperature. After 4 hours, the mixture was filtrated through Celite®, and concentrated, and then the resulting residue was purified by silica gel column chromatography (chloroform:methanol=10:1) to give the title compound (14%).

LC-MS: condition B R.T.=1.8 min ObsMS=298 [M+1]

Example 44

2,4-Dimethyl-5-[4-(pyridin-2-yl)piperidin-1-ylmethyl]pyrimidine

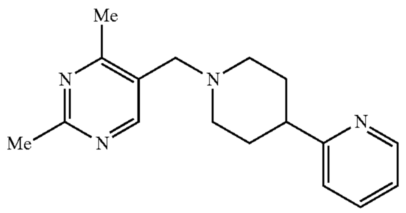 [SMILES: Cc1ncc(CN2CCC(c3ccccn3)CC2)c(C)n1]

To a solution of (2,4-dimethylpyrimidin-5-yl)methanol (1.71 g, 12.4 mmol) in tetrahydrofuran (40 mL) were added triethylamine (1.74 mL, 12.5=mmol) and methanesulfonyl chloride (0.969 mL, 12.5 mmol) at 0° C. The mixture was stirred at 0° C. for 1 hour, and then the insoluble product was filtered off. The resulting filtrate was added to a mixture of the compound of Reference Example 3 (2.94 g, 12.5 mmol), dimethylformamide (60 mL) and potassium carbonate (7.71 g, 55.8 mmol). The reaction mixture was stirred at room temperature overnight, then water (400 mL) was added thereto, and the mixture was extracted with ethyl acetate (300 mL) and chloroform (300 mL×2). The combined organic layer was dried over anhydrous sodium sulfate, filtrated, and concentrated. The resulting residue was purified by silica gel column chromatography (chloroform: methanol), and then by amino column chromatography (hexane:ethyl acetate) to give the title compound (2.25 g, 64%).

$^1$H-NMR (300 MHz, $CDCl_3$) δ: 1.74-1.97 (4H, m), 2.16 (2H, td, J=11.3, 2.8 Hz), 2.56 (3H, s), 2.65-2.78 (1H, m), 2.69 (3H, s), 2.90-2.99 (2H, m), 3.46 (2H, s), 7.11 (1H, ddd, J=7.5, 5.0, 1.1 Hz), 7.14-7.18 (1H, m), 7.61 (1H, td, J=7.7, 1.8 Hz), 8.40 (1H, s), 8.52-8.55 (1H, m).

Example 45

2,4-Dimethyl-5-[4-(pyridin-3-yl)piperidin-1-ylmethyl]pyrimidine

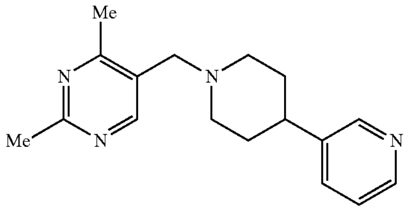 [SMILES: Cc1ncc(CN2CCC(c3cccnc3)CC2)c(C)n1]

The title compound was prepared from the compound of Reference Example 11 according to a similar process to that of Example 44 (yield: 86%).

$^1$H-NMR (300 MHz, $CDCl_3$) δ: 1.64-1.88 (4H, m), 2.16 (2H, td, J=11.4, 2.8 Hz), 2.49-2.62 (1H, m), 2.57 (3H, s), 2.69 (3H, s), 2.90-3.00 (2H, m), 3.47 (2H, s), 7.23 (1H, ddd, J=7.8, 4.8, 0.7 Hz), 7.53 (1H, ddd, J=7.9, 2.0, 2.0 Hz), 8.41 (1H, s), 8.45 (1H, dd, J=4.8, 1.7 Hz), 8.49 (1H, brd, J=2.2 Hz).

Example 46

5-[4-(5-Fluoropyridin-3-yl)piperidin-1-ylmethyl]pyrimidin-2-amine

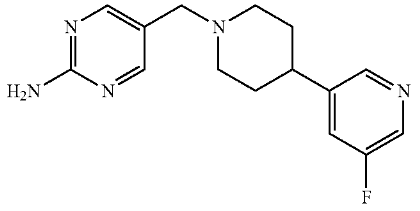 [SMILES: Nc1ncc(CN2CCC(c3cncc(F)c3)CC2)cn1]

The title compound was prepared from the compound of Reference Example 13 according to a similar process to that of Example 7 (yield: 34%).

$^1$H-NMR (300 MHz, $CDCl_3$) δ: 1.73-1.93 (4H, m), 2.11 (2H, td, J=11.6, 2.7 Hz), 2.55-2.67 (1H, m), 2.98-3.07 (2H, m), 3.42 (2H, s), 5.06 (2H, s), 7.24-7.31 (1H, m), 8.28 (2H, s), 8.34 (2H, brd, J=2.4 Hz).

Example 47

2-Methyl-5-[4-(1,3-thiazol-2-yl)piperidin-1-ylmethyl]pyrimidin-4-amine

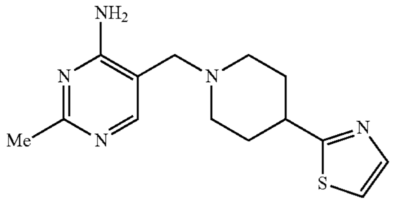 [SMILES: Cc1ncc(CN2CCC(c3nccs3)CC2)c(N)n1]

The title compound was prepared from the compound of Reference Example 55 according to a similar process to that of Example 1 (yield: 13%).

$^1$H-NMR (400 MHz, $CD_3OD$) δ: 1.78-1.93 (2H, m), 2.06-2.23 (4H, m), 2.42 (3H, s), 2.90-3.00 (2H, m), 3.03-3.14 (1H, m), 3.47 (2H, s), 7.47 d, J=3.2 Hz), 7.71 (1H, d, J=3.2 Hz), 7.89 (1H, s).

Example 48

5-[4-(5-Fluoropyridin-3-yl)piperidin-1-ylmethyl]-2,4-dimethylpyrimidine

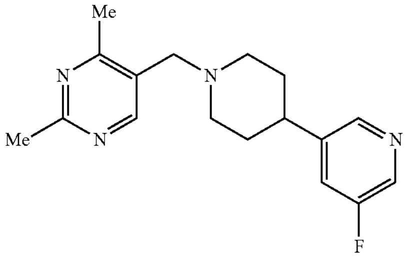 [SMILES: Cc1ncc(CN2CCC(c3cncc(F)c3)CC2)c(C)n1]

A mixture of the compound of Reference Example 56 (253 mg, 1.00 mmol), 2,4-dimethylpyrimidine-5-carboxylic acid (152 mg, 1.00 mmol), 1-hydroxybenzotriazole (135 mg, 1.00 mmol), 1-(3-dimethylaminopropyl)-3-ethylcarbodiimide hydrochloride (230 mg, 1.20 mmol), triethylamine (418 μL, 3.00 mmol), and N,N-dimethylformamide (2 mL) was stirred at room temperature for 16 hours. The reaction mixture was then purified directly by preparative high-performance liquid chromatography. To a solution of the resulting purified product (157 mg, 0.50 mmol) in tetrahydrofuran (5.0 mL) was then added lithium aluminum hydride (56.9 mg, 1.50 mmol) at 10° C. The mixture was stirred at 10° C. for 16 hours, then water and 10% sodium hydroxide were added thereto, the precipitate was removed through Celite®, and the filtrate was concentrated. The resulting concentrated residue was purified by preparative high-performance liquid chromatography to give the title compound (4%).

$^1$H-NMR (400 MHz, $CDCl_3$) δ: 1.63-1.82 (2H, m), 1.82-1.93 (2H, m), 2.17 (2H, brt, J=10.8 Hz), 2.53-2.70 (1H, m), 2.58 (3H, s), 2.71 (3H, s), 2.97 (2H, brd, J=11.2 Hz), 3.48 (2H, s), 7.23-7.34 (1H, m), 8.33 (2H, s), 8.42 (1H, s).

Examples 49-50

The compounds of Examples 49-50 were synthesized from the compounds of the corresponding Reference Examples according to the process of Example 48.

| Examples | Chemical Structure | Instrumental Analysis Data |
|---|---|---|
| 49 | 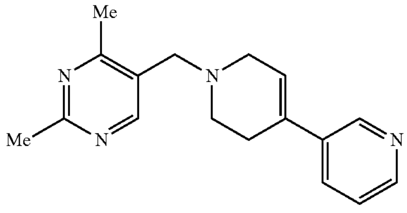 [SMILES: Cc1ncc(CN2CC=C(c3cccnc3)CC2)c(C)n1] | $^1$H-NMR (400 MHz, $CDCl_3$) δ: 2.48-2.58 (2H, m), 2.58 (3H, s), 2.65-2.78 (5H, m), 3.19 (2H, d, J = 3.2 Hz), 3.58 (2H, s), 6.12 (1H, s), 7.21-7.27 (1H, m), 7.62-7.69 (1H, m), 8.45 (1H, s), 8.46-8.53 1H, m), 8.66 (1H, d, J = 2.0 Hz) . |
| 50 | 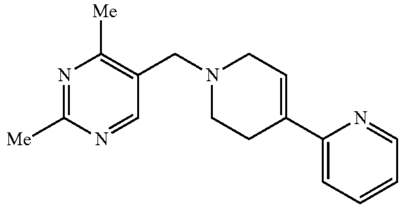 [SMILES: Cc1ncc(CN2CC=C(c3ccccn3)CC2)c(C)n1] | $^1$H-NMR (400 MHz, $CDCl_3$) δ: 2.50 (3H, s), 2.54-2.70 (7H, m), 3.13-3.19 (2H, m), 3.51 (2H, s), 6.55 (1H, brs), 7.03-7.10 (1H, m), 7.30 (1H, d, J = 8.2 Hz), 7.53-7.60 (1H, m), 8.38 (1H, s), 3.48 (1H, d, J = 6.1 Hz). |

Examples 51-56

The compounds of Examples 51-56 were synthesized from the compounds of the corresponding Reference Examples according to the process of Example 10.

| Examples | Chemical Structure | Instrumental Analysis Data |
|---|---|---|
| 51 | 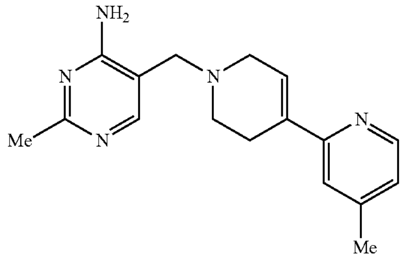 [SMILES: Cc1ccnc(C2=CCN(Cc3cnc(C)nc3N)CC2)c1] | $^1$H-NMR (400 MHz, $CDCl_3$) δ: 2.28 (3H, s), 2.44 (3H, s), 2.55-2.70 (4H, m), 3.11 (2H, d, J = 2.8 Hz), 3.50 (2H, s), 6.53 (1H, s), 6.91 (1H, d, J = 4.4 Hz), 7.12 (1H, s), 7.91 (1H, s), 8.34 (1H, d, J = 5.2 Hz). |
| 52 | 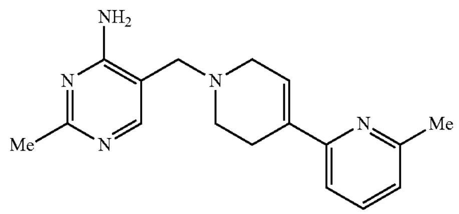 [SMILES: Cc1cccc(C2=CCN(Cc3cnc(C)nc3N)CC2)n1] | $^1$H-NMR (400 MHz, $CDCl_3$) δ: 2.50 (3H, s), 2.54 (3H, s), 2. 60-2.75 (4H, m), 3.18 (2H, d, J = 2.8 Hz), 3.56 (2H, s), 6.64 (1H, s), 7.01 (1H, d, J = 8.0 Hz), 7.13 (1H, d, J = 7.6 Hz), 7.53 (1H, dd, J = 8.0, 8.0 Hz), 7.98 (1H, s). |

-continued

| Examples | Chemical Structure | Instrumental Analysis Data |
|---|---|---|
| 53 | 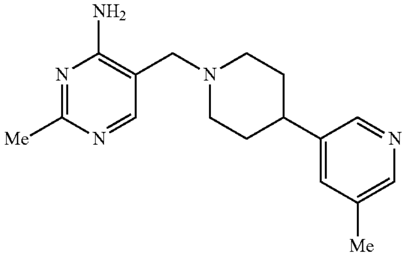 [SMILES: Cc1cncc(C2CCN(Cc3cnc(C)nc3N)CC2)c1] | $^{1}$H-NMR (400 MHz, DMSO-$d_6$) δ: 1.55-1.79 (4H, m), 2.01 (2H, brt, J = 11.2 Hz), 2.27 (3H, s), 2.30 (3H, s), 2.88 (2H, brd, J = 11.2 Hz) , 3.39-3.49 (1H, m), 4.46 (2H, s), 6.79 (2H, brs), 7.48 (1H, s), 7.86 (1H, s), 8.23 (1H, s), 8.26 (1H, s). |
| 54 | 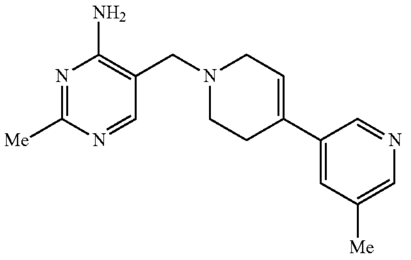 | $^{1}$H-NMR (400 MHz, DMSO-$d_6$) δ: 2.29 (3H, s), 2.31 (3H, s), 2.62 (2H, t, J = 5.6 Hz), 3.05 (2H, d, J = 2.8 Hz), 3.43 (2H, brs), 6.05 (2H, brs), 6.25 (1H, s), 6.75 (2H, brs), 7.63 (1H, s), 7.89 (1H, s), 8.28 (1H, s), 8.45 (1H, d, J = 1.6 Hz). |
| 55 | 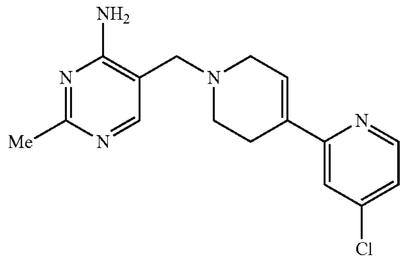 [SMILES: Cc1ncc(CN2CC=C(c3cc(Cl)ccn3)CC2)c(N)n1] | $^{1}$H-NMR (400 MHz, $CDCl_3$) δ: 2.51 (3H, s), 2.64 (2H, brs), 2.72 (2H, t, J = 5.2 Hz), 3.20 (2H, d, J = 2.8 Hz), 3.57 (2H, s), 6.68 (1H, 3), 7.17 (1H, dd, J = 5.4, 1.6 Hz), 7.37 (1H, d, J = 1.6 Hz), 7.98 (1H, s), 8.46 (1H, d, J = 5.4 Hz). |
| 56 | 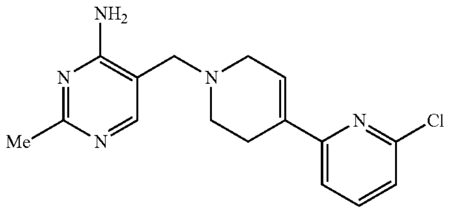 [SMILES: Cc1ncc(CN2CC=C(c3cccc(Cl)n3)CC2)c(N)n1] | $^{1}$H-NMR (400 MHz, $CDCl_3$) δ: 2.51 (3H, s), 2.63 (2H, brs), 2.71 (2H, t, J = 6.0 Hz), 3.19 (2H, d, J = 2.8 Hz), 3.57 (2H, s), 6.72 (1H, s), 7.18 (1H, d, J = 8.0 Hz), 7.26 (1H, d, J = 8.0 Hz), 7.61 (1H, dd, J = 8.0, 8.0 Hz), 7.98 (1H, s). |

Example 57

2-Methyl-5-[4-(4-methylpyridin-2-yl)piperidin-1-ylmethyl]pyrimidin-4-amine

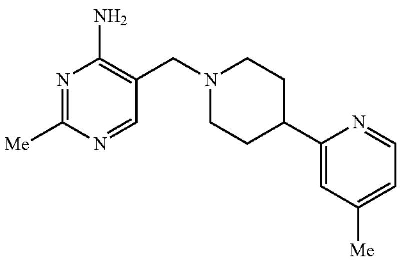 [SMILES: Cc1ccnc(C2CCN(Cc3cnc(C)nc3N)CC2)c1]

To a solution of the compound of Reference Example 57 (276 mg, 1.00 mmol) in 1,4-dioxane (1.5 mL) was added 4 mol/L hydrochloric acid/1,4-dioxane solution (3.0 mL), and the mixture was stirred at room temperature for 16 hours. The reaction mixture was then concentrated, and the resulting residue was washed with ethyl acetate. The title compound was then prepared from the resulting product according to a similar process to that of Example 10 (yield: 13%).

$^{1}$H-NMR (400 MHz, $CDCl_3$) δ: 1.62-1.92 (4H, m), 2.02 (2H, brt, J=8.8 Hz), 2.26 (3H, s), 2.42 (3H, s), 2.54-2.65 (1H, m), 2.90 (2H, brd, J=11.6 Hz), 3.38 (2H, s), 6.88 (1H, d, J=5.2 Hz), 6.90 (1H, s), 7.86 (1H, s), 8.32 (1H, d, J=4.8 Hz).

Reference Example 1

1',2',3',6'-Tetrahydro-2,4'-bipyridine dihydrochloride

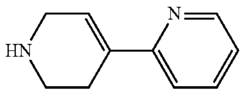

2HCl

To a solution of the compound of Reference Example 4 (327 mg, 1.26 mmol) in 1,4-dioxane (3.2 mL) was added 4 mol/L hydrochloric acid/1,4-dioxane solution (6.5 mL). The mixture was stirred at room temperature for 1 hour, and the solvent was evaporated to give the title compound (293 mg, 99%).

$^1$H-NMR (300 MHz, DMSO-$D_5$) δ: 2.76-2.86 (2H, m), 3.24-3.35 (2H, m), 3.76-3.87 (2H, m), 6.82 (1H, m), 7.52 (1H, t, J=6.2 Hz), 7.79 (1H, d, J=8.1 Hz), 8.06 (1H, t, J=7.2 Hz), 8.64 (1H, d, J=5.0 Hz), 9.47 (2H, brs).

Reference Example 2

1',2',3',6'-Tetrahydro-3,4'-bipyridine dihydrochloride

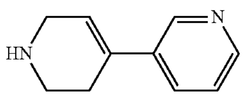

2HCl

To a solution of the compound of Reference Example 5 (1.17 g, 4.49 mmol) in 1,4-dioxane (7.0 mL) was added 4 mol/L hydrochloric acid/1,4-dioxane solution (14 mL). The mixture was stirred at room temperature for 2 hours, and concentrated. To the resulting concentrated residue was added diethyl ether (7.0 mL), the mixture was stirred at room temperature for 30 minutes, and the precipitate was collected by filtration. The filter cake was washed with diethyl ether (2.3 mL), and dried under reduced pressure to the title compound (942 mg, 90%).

$^1$H-NMR (300 MHz, DMSO-$D_6$) δ: 2.69-2.81 (2H, m), 3.25-3.37 (2H, m), 3.75-3.83 (2H, m), 6.51-6.56 (1H, m), 7.86 (1H, dd, J=8.3, 5.3 Hz), 8.40-8.46 (1H, m), 8.74 (1H, dd, J=5.3, 1.3 Hz), 8.92 (1H, d, J=2.2 Hz), 9.46 (2H, brs).

Reference Example 3

2-(Piperidin-4-yl)pyridine dihydrochloride

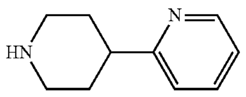

2HCl

The title compound was prepared from the compound of Reference Example 6 according to a similar process to that of Reference Example 1 (yield: 99%).

$^1$H-NMR (400 MHz, DMSO-$D_6$) δ: 1.93-2.08 (2H, m), 2.08-2.17 (2H, m), 2.93-3.07 (2H, m), 3.28-3.43 (3H, m), 7.67-7.78 (2H, m), 8.26-8.36 (1H, m), 8.70-8.75 (1H, m), 9.03-9.32 (2H, m).

Reference Example 4 tert-Butyl 3',6'-dihydro-2,4'-bipyridine-1'(2'H)-carboxylate

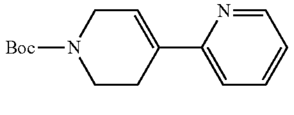 [SMILES: CC(C)(C)OC(=O)N1CC=C(c2ccccn2)CC1]

To a solution of 2-bromopyridine (5.11 g, 32.3 mmol) in dimethoxyethane (100 mL) were added water (50 mL), 1-N-Boc-4-(4,4,5,5-tetramethyl-[1,3,2]-dioxaborolan-2-yl)-3,6-dihydro-2H-pyridine (10 g, 32.3 mmol), sodium carbonate (17.1 g, 162 mmol), and tetrakis(triphenylphosphine) palladium (0) (0.373 g, 0.323 mmol). The mixture was heated under reflux for 6 hours, then water (150 mL) was added thereto, and the mixture was extracted with ethyl acetate (200 mL) twice. The combined organic layer was dried over anhydrous magnesium sulfate, filtrated, and concentrated. The resulting concentrated residue was purified by silica gel column chromatography (hexane:ethyl acetate=81:9 to 60:40) to give the title compound (4.99 g, 59%).

$^1$H-NMR (300 MHz, $CDCl_3$) δ: 1.49 (9H, s), 2.60-2.70 (2H, m), 3.59-3.72 (2H, m), 4.09-4.19 (2H, m), 6.56-6.64 (1H, m), 7.15 (1H, ddd, J=7.5, 4.8, 1.0 Hz), 7.37 (1H, d, J=8.1 Hz), 7.66 (1H, ddd, J=7.8, 7.8, 1.8 Hz), 8.54-8.59 (1H, m).

Reference Example 5 tert-Butyl 3',6'-dihydro-3,4'-bipyridine-1'(2'H)-carboxylate

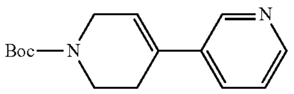 [SMILES: CC(C)(C)OC(=O)N1CC=C(c2cccnc2)CC1]

To a solution of 3-bromopyridine (102 mg, 0.647 mmol) in dimethoxyethane (4.0 mL) were added water (2.0 mL), 1-N-Boc-4-(4,4,5,5-tetramethyl-[1,3,2]-dioxaborolan-2-yl)-3,6-dihydro-2H-pyridine (200 mg, 0.647 mmol), sodium carbonate (343 mg, 3.24 mmol), and tetrakis(triphenylphosphine)palladium (0) (7.5 mg, 0.00647 mmol). The reaction solution was heated under reflux for 4 hours, then water (20 mL) was added thereto, and the mixture was extracted with ethyl acetate (20 mL) twice. The combined organic layer was dried over anhydrous sodium sulfate, filtrated, and concentrated. The resulting concentrated residue was purified by silica gel column chromatography (hexane:ethyl acetate=57:43 to 36:64) to give the title compound (156 mg, 93%).

$^1$H-NMR (300 MHz, $CDCl_3$) δ: 1.50 (9H, s), 2.49-2.57 (2H, m), 3.66 (2H, t, J=5.7 Hz), 4.07-4.12 (2H, m), 6.05-6.14 (1H, m), 7.26 (1H, ddd, J=7.8, 4.9, 0.9 Hz), 7.64 (1H, ddd, J=8.0, 2.3, 1.6 Hz), 8.50 (1H, dd, J=4.9, 1.6 Hz), 8.65 (1H, d, J=1.8 Hz).

Reference Example 6 tert-Butyl 4-(pyridin-2-yl)piperidine-1-carboxylate

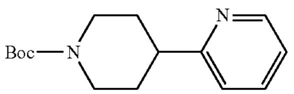

To a solution of the compound of Reference Example 4 (4.99 g, 19.2 mmol) in methanol (100 mL) was added 10 palladium/carbon (2.0 g), and the mixture was stirred under hydrogen atmosphere at room temperature for 6 hours. After stirring, the mixture was filtrated through Celite®, and concentrated. The resulting concentrated residue was purified by silica gel column chromatography (hexane:ethyl acetate=76:24 to 55:45) to give the title compound (4.16 g, 83%).

$^1$H-NMR (400 MHz, $CDCl_3$) δ: 1.48 (9H, s), 1.66-1.79 (2H, m), 1.86-1.96 (2H, m), 2.75-2.93 (3H, m), 4.15-4.40 (2H, m), 7.10-7.17 (2H, m), 7.63 (1H, ddd, J=7.7, 7.7, 1.9 Hz), 8.52-8.56 (1H, m).

Reference Examples 7-20

According to the above processes of Reference Examples 1-6, the compounds of Reference Examples 7-20 were synthesized from 1-N-Boc-4-(4,4,5,5-tetramethyl-[1,3,2]-dioxaborolan-2-yl)-3,6-dihydro-2H-pyridine.

| Reference Examples | Chemical Structure | Instrumental Analysis Data |
|---|---|---|
| 7 | 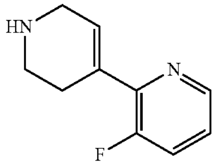 2HCl | $^1$H-NMR (DMSO-$D_6$) δ: 2.74-2.85 (2H, m), 3.23-3.35 (2H, m), 3.73-3.84 (2H, m), 6.52- 6.59 (1H, m), 7.39-7.45 (1H, m), 7.76 (1H, ddd, J = 12.2, 8.3, 1.3 Hz), 8.42-8.46 (1H, m), 9.37 (2H, brs). |
| 8 | 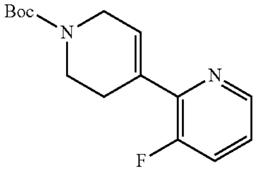 [SMILES: CC(C)(C)OC(=O)N1CC=C(c2ncccc2F)CC1] | $^1$H-NMR (300 MHz, $CDCl_3$) δ: 1.50 (9H, s), 2.64-2.75 (2H, m), 3.64 (2H, t, J = 5.7 Hz), 4.10-4.20 (2H, m), 6.47-6.59 (1H, m), 7.14-7.21 (1H, m), 7.38 (1H, ddd, J = 11.4, 8.3, 1.4 Hz), 8.39 (1H, ddd, J = 3.0, 3.0, 1.6 Hz). |
| 11 | 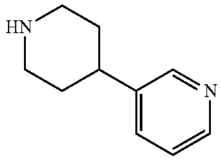 2HCl | $^1$H-NMR (300 MHz, DMSO-$D_6$) δ: 1.82-2.08 (4H, m), 2.88-3.16 (3H, m), 3.31-3.43 (2H, m), 7.91 (1H, dd, J = 8.0, 5.6 Hz), 8.30 (1H, d, J = 8.1 Hz), 8.72-8.77 (2H, m), 9.10 (2H, brs). |
| 12 | 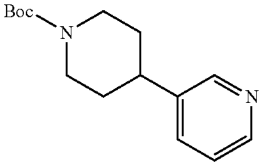 [SMILES: CC(C)(C)OC(=O)N1CCC(c2cccnc2)CC1] | $^1$H-NMR (300 MHz, $CDCl_3$) δ: 1.49 (9H, s), 1.61-1.74 (2H, m), 1.75-1.91 (2H, m), 2.59-2.75 (1H, m), 2.75-2.90 (2H, m), 4.15-4.37 (2H, m), 7.18-7.25 (1H, m), 7.46-7.54 (1 H, m), 8.42-8.51 (2H, m). |
| 13 | 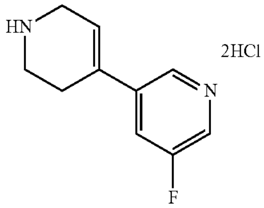 [SMILES: Fc1cncc(C2=CCNCC2)c1] 2HCl | $^1$H-NMR (400 MHz, DMSO-$D_6$) δ: 2.79 (2H, s), 3.25-3.30 (2H, m), 3.78 (2H, s), 6.56 (1H, s), 7.40-7.44 (1H, m), 7.73-7.79 (1H, m), 8.44-8.45 (1H, m), 9.40 (2H, brs). |
| 14 | 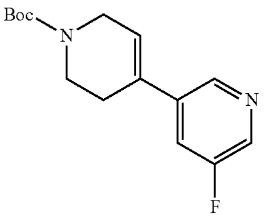 [SMILES: CC(C)(C)OC(=O)N1CC=C(c2cncc(F)c2)CC1] | $^1$H-NMR (400 MHz, $CDCl_3$) δ: 1.50 (9H, s), 2.42-2.52 (2H, m), 3.65-3.73 (2H, m), 4.11-4.15 (2H, m), 6.16 (1H, brs), 7.34-7.37 (1H, m), 8.36-8.42 (1H, m), 8.47-8.50 (1H, m). |

-continued

| Reference Examples | Chemical Structure | Instrumental Analysis Data |
|---|---|---|
| 15 | 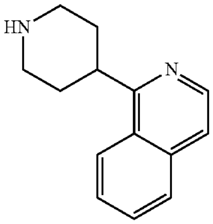 2HCl | $^1$H-NMR (400 MHz, $CD_3OD$) δ: 2.30-2.40 (2H, m), 2.41-2.55 (2H, m), 3.39-3.53 (2H, m), 3.61-3.71 (2H, m), 4.50-4.61 (1H, m), 8.07-8.15 (1H, m), 8.24 (1H, dd, J = 7.6, 7.6 Hz), 8.33 (1H, d, J = 8.0 Hz), 8.42 (1H, d, J = 6.4 Hz), 8.48 (1H, d, J = 3.2 Hz), 8.89 (1H, d, J = 6.4 Hz). |
| 16 | 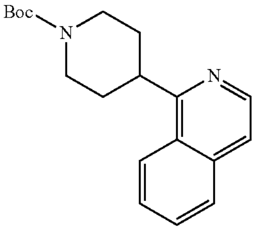 [SMILES: CC(C)(C)OC(=O)N1CCC(c2nccc3ccccc23)CC1] | $^1$H-NMR (400 MHz, DMSO-$D_6$) δ: 1.43 (9H, s), 1.70-1.85 (4H, m), 2.90-3.13 (2H, m), 3.77-3.90 (1H, m), 4.03-4.18 (2H, m), 7.63-7.70 (2H, m), 7.72-7.80 (1H, m), 7.96 (1H, d, J = 8.0 Hz), 8.38 (1H, d, J = 8.4 Hz), 8.43 (1H, d, J = 5.6 Hz). |
| 17 | 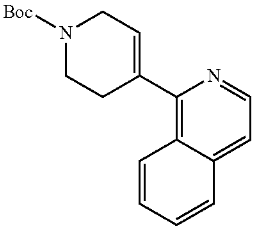 [SMILES: CC(C)(C)OC(=O)N1CC=C(c2nccc3ccccc23)CC1] | $^1$H-NMR (400 MHz, DMSO-D6) δ: 1.46 (9H, s), 2.56-2.67 (2H, m), 3. 56-3.70 (2H, m), 4.05-4.15 (2H, m), 5.93-6.05 (1H, m), 7.60-7.69 (1H, m), 7.70-7.81 (2H, m), 7.98 (1H, d, J = 8.0 Hz), 8.26 (1H, d, J = 8.4 Hz), 8.46 (1H, d, J = 5.6 Hz). |
| 18 | 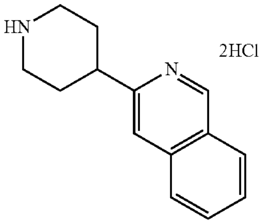 [SMILES: c1ccc2cc(C3CCNCC3)ncc2c1] 2HCl | $^1$H-NMR (400 MHz, DMSO-$D_6$) δ: 2.00-2.14 (2H, m), 2.18-2.30 (2H, m), 2.95-3.11 (2H, m), 3.31-3.45 (3H, m), 7.87 (1H, dd, J = 7.2, 7.2 Hz), 8.06 (1H, dd, J = 7.6, 7.6 Hz), 8.11-8.23 (2H, m), 8.41 (1H, d, J = 8.0 Hz), 9.30 (2H, brs), 9, 72 (1H, s). |
| 19 | 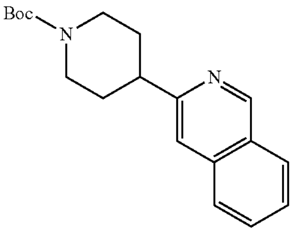 [SMILES: CC(C)(C)OC(=O)N1CCC(c2cc3ccccc3cn2)CC1] | $^1$H-NMR (400 MHz, DMSO-$D_6$) δ: 1.43 (9H, s), 1.60-1.74 (2H, m), 1.87-1.97 (2H, m), 2.79-3.04 (3H, m), 4.04-4.17 (2H, m), 7.58-7.65 (1H, m), 7.66 (1H, s), 7.71-7.78 (1H, m), 7.90 (1H, d, J = 8.4 Hz), 8.07 (1H, d, J = 8.0 Hz), 9.26 (1H, s). |
| 20 | 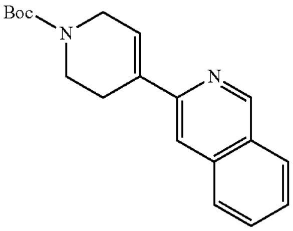 [SMILES: CC(C)(C)OC(=O)N1CC=C(c2cc3ccccc3cn2)CC1] | $^1$H-NMR (400 MHz, DMSO-$D_6$) δ: 1.43 (9H, s), 2.60-2.69 (2H, m), 3.56-3.64 (2H, m), 4.06-4.14 (2H, m), 6.92-7.00 (1H, m), 7.60-7.66 (1H, m), 7.72-7.80 (1H, m), 7.84 (1H, s), 7.95 (1H, d, J = 8.0 Hz), 8.09 (1H, d, J = 8.0 Hz), 9.28 (1H, s). |

Reference Example 21

4-Amino-2-methylpyrimidine-5-carbaldehyde

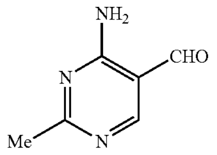

To a solution of the compound of Reference Example 22 (50.0 g, 373 mmol) in formic acid (150 mL) were added water (65 mL) and Raney nickel (50 g). The mixture was heated under reflux for 15 minutes, cooled to room temperature, and filtrated through Celite®, and then 28% ammonia water (220 mL) was added thereto under ice cooling. The mixture was stirred under ice cooling for 1 hour, and the precipitate was collected by filtration. The filter cake was washed with water (30 mL) and chloroform (30 mL×2), and dried in vacuo. Furthermore, the filtrate was extracted with chloroform (200 mL) nine times, and the combined organic layer was concentrated. The resulting concentrated residue and the above-obtained filter cake were mixed, chloroform (70 mL) was added thereto, the mixture was stirred at room temperature for 30 minutes, hexane (210 mL) was added dropwise thereto over 10 minutes, and the mixture was stirred at room temperature for additional 1 hour. The precipitate was collected by filtration, washed with hexane/chloroform (3/1, 28 mL), and dried in vacuo to give the title compound (42.6 g, 83%). $^1$H-NMR (400 MHz, $CDCl_3$) δ: 2.57 (3H, s), 5.98 (1H, brs), 8.15 (1H, brs), 8.57 (1H, s), 9.86 (1H, s).

Reference Example 22

4-Amino-2-methylpyrimidine-5-carbonitrile

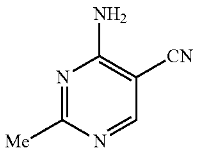

A mixture of dimethylformamide (74.5 mL, 962 mmol) and dimethyl sulfate (90.8 mL, 962 mmol) was stirred at 70° C. for 3.5 hours, a solution of sodium methoxide (52.0 g, 962 mmol) in methanol (440 mL) was added dropwise at a temperature of-20° C. to −10° C. over 40 minutes, and then a solution of malononitrile (63.6 g, 962 mmol) in methanol mL) was added at a temperature of −20° C. to −10° C. over 40 minutes. The mixture was stirred at −15° C. for 1 hour. Separately, to a solution of sodium methoxide (57.2 g, 1060 mmol) in methanol (320 mL) was added acetamidine hydrochloride (100 g, 1060 mmol) under ice cooling, then the mixture was stirred for 15 minutes, and filtrated to prepare a solution of acetamidine in methanol. The solution of acetamidine in methanol was added dropwise to the above-obtained reaction mixture at a temperature of −20° C. to −10° C. over 15 minutes, and the mixture was stirred at −15° C. for 30 minutes, and then at room temperature for 15 hours. The precipitate was then collected by filtration, washed with water (200 mL×2), and dried in vacuo to give the title compound (88.5 g, 69%).

$^1$H-NMR (300 MHz, DMSO-$D_6$) δ: 2.37 (3H, s), 7.76 (2H, brs), 8.49 (1H, s).

Reference Example 23

4-Amino-2-ethylpyrimidine-5-carbaldehyde

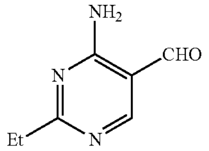 [SMILES: CCc1ncc(C=O)c(N)n1]

To a 70% solution of the compound of Reference Example 24 (148 mg, 1.00 mmol) in acetic acid (5.0 mL) was added Raney nickel (1.0 g), and the mixture was stirred under hydrogen atmosphere at room temperature for 32 hours. The reaction mixture was then filtrated through Celite®, and concentrated. To the concentrated residue was added saturated aqueous sodium hydrogen carbonate solution until the pH of the solution becomes 9, and the mixture was extracted with ethyl acetate (20 mL). The organic layer was dried over anhydrous sodium sulfate, filtrated, and concentrated to give the title compound (107 mg, 71%).

$^1$H-NMR (400 MHz, DMSO-$D_6$) δ: 1.20 (3H, t, J=7.6 Hz), 2.66 (2H, q, J=7.6 Hz), 7.89 (1H, brs), 8.15 (1H, brs), 8.66 (1H, s), 9.81 (1H, s).

Reference Example 24

4-Amino-2-ethylpyrimidine-5-carbonitrile

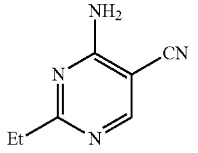 [SMILES: CCc1ncc(C#N)c(N)n1]

To 2.27 mol/L sodium ethoxide/ethanol solution (2.50 mL, 1.10 mmol) was added propionamidine hydrochloride (109 mg, 1.00 mmol), and the mixture was stirred at room temperature for 10 minutes. The reaction mixture was then filtrated through Celite®, and to the filtrate was added (ethoxymethylene)malononitrile (110 mg, 0.900 mmol). The mixture was stirred at room temperature for 30 minutes, and the reaction mixture was concentrated. To the resulting concentrated residue was added tert-butyl methyl ether (1.0 mL), the mixture was stirred for 1 hour, and the precipitate was collected on a filter to give the title compound (105 mg, 73%).

$^1$H-NMR (400 MHz, $CDCl_3$) δ: 1.26 (3H, t, J=7.6 Hz), 2.76 (2H, q, J=7.6 Hz), 5.99 (2H, brs), 8.43 (1H, s).

Reference Examples 25-30

According to the above processes of Reference Examples 23-24, the compounds of Reference Examples 25-30 were synthesized from (ethoxymethylene)malononitrile.

| Examples Reference | Chemical Structure | Instrumental Analysis Data |
|---|---|---|
| 25 | 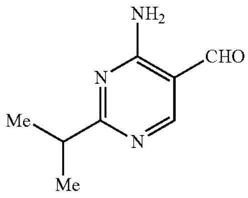 [SMILES: CC(C)c1ncc(C=O)c(N)n1] | $^1$H-NMR (400 MHz, $CDCl_3$) δ: 1.29 (6H, d, J = 7.2 Hz), 2.92-3.10 (1H, m), 5.73 (1H, brs), 6.03 (1H, brs), 8.64 (1H, s), 9.86 (1H, s). |
| 26 | 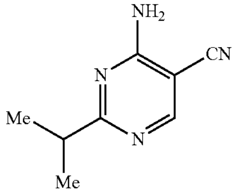 [SMILES: CC(C)c1ncc(C#N)c(N)n1] | $^1$H-NMR (400 MHz, $CDCl_3$) δ: 1.30 (6H, d, J = 6.8 Hz), 2.97-3.10 (1H, m), 5.57 (2H, brs), 8.53 (1H, s). |
| 27 | 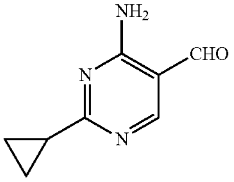 [SMILES: Nc1nc(C2CC2)ncc1C=O] | $^1$H-NMR (400 MHz, DMSO-$D_6$) δ: 0.64-1.45 (4H, m), 1.85-2.21 (1H, m), 7.67-8.36 (2H, m), 8.63 (1H, brs), 9.82 (1H, brs). |
| 28 | 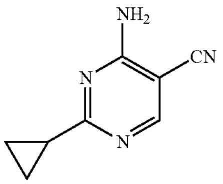 [SMILES: N#Cc1cnc(C2CC2)nc1N] | $^1$H-NMR (400 MHz, DMSO-$D_6$) δ: 0.87-1.03 (4H, m), 1.87-1.97 (1H, m), 7.65 (2H, brs), 8.41 (1H, s). |
| 29 | 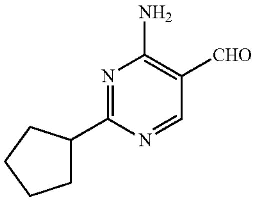 [SMILES: Nc1nc(C2CCCC2)ncc1C=O] | $^1$H-NMR (400 MHz, $CDCl_3$) δ:1.54-2.12 (8H, m), 3.06-3.24 (1H, m), 5.58 (1H, brs), 5.84 (1H, brs), 8.59 (1H, s), 9.84 (1H, s). |
| 30 | 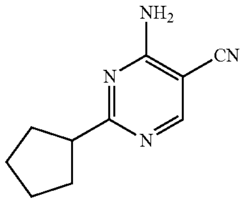 [SMILES: N#Cc1cnc(C2CCCC2)nc1N] | $^1$H-NMR (400 MHz, $CDCl_3$) δ:1.48-1.88 (8H, m), 3.03-3.18 (1H, m), 4.00-4.12 (2H, m), 8.39 (1H, brs). |

Reference Example 31

2-Methyl-4-(methylamino)pyrimidine-5-carbaldehyde

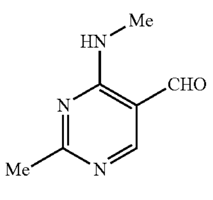 [SMILES: CNc1nc(C)ncc1C=O]

To a solution of the compound of Reference Example 32 (153 mg, 1.00 mmol) in dichloromethane (5.0 mL) was added manganese dioxide (869 mg, 10.0 mmol). The reaction mixture was stirred at room temperature for 16 hours, filtrated, and concentrated to give the title compound (101 mg, 67%).

$^1$H-NMR (400 MHz, $CDCl_3$) δ: 2.61 (3H, s), 3.13 (3H, d, J=4.8 Hz), 8.45 (1H, s), 9.79 (1H, s).

Reference Example 32

[2-Methyl-4-(methylamino)pyrimidin-5-yl]methanol

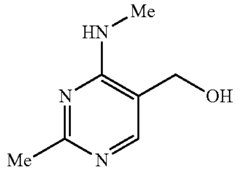 [SMILES: CNc1nc(C)ncc1CO]

To a suspension of lithium aluminum hydride (1.0 g, 26.4 mmol) in tetrahydrofuran (100 mL) was added dropwise a solution of the compound of Reference Example 33 (5.15 g, 26.4 mmol) in tetrahydrofuran (30 mL) at −5° C. The mixture was then stirred at −5° C. for 2 hours, and water (1.0 mL) and then 10% aqueous sodium hydroxide solution (1.0 mL) were gradually added thereto. The reaction mixture was filtrated, dried over anhydrous sodium sulfate, filtrated, and concentrated to give the title compound (3.88 g, 96%).

$^1$H-NMR (400 MHz, DMSO-$D_6$) δ: 2.35 (3H, s), 2.86 (3H, d, J=4.8 Hz), 4.32 (2H, brs), 6.59 (1H, brs), 7.86 (1H, s).

Reference Example 33

Ethyl 2-methyl-4-(methylamino)pyrimidine-5-carboxylate

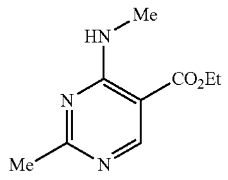 [SMILES: CCOC(=O)c1cnc(C)nc1NC]

To a mixture of the compound of Reference Example 34 (7.28 g, 40.0 mmol) and phosphorous oxychloride (80 mL) was added triethylamine (5.0 mL, 36.0 mmol) at 30° C. The mixture was stirred at 40° C. for 50 minutes, and concentrated. To the resulting concentrated residue was added chloroform (400 mL), the mixture was poured into ice water (400 mL), and the organic layer was separated. The organic layer was washed with 5% aqueous sodium hydrogen carbonate solution (200 mL) and brine (200 mL), dried over anhydrous sodium sulfate, filtrated, and concentrated. The resulting concentrated residue was dissolved in tetrahydrofuran (60 mL), then methylamine (6.21 g, 200 mmol) was added thereto, and the mixture was stirred at room temperature for 10 minutes. To the reaction mixture was then added chloroform (400 mL), and the mixture was washed with brine (200 mL). The organic layer was dried over anhydrous sodium sulfate, filtrated, and concentrated. The resulting concentrated residue was purified by silica gel column chromatography (hexane:ethyl acetate) to give the title compound (3.98 g, 51%).

$^1$H-NMR (400 MHz, $CDCl_3$) δ: 1.39 (3H, t, J=7.2 Hz), 2.56 (3H, s), 3.08 (3H, d, J=5.2 Hz), 4.34 (2H, q, J=7.2 Hz), 8.10 (1H, brs), 8.73 (1H, s).

Reference Example 34

Ethyl 2-methyl-6-oxo-1,6-dihydropyrimidine-5-carboxylate

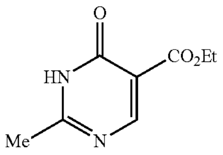 [SMILES: CCOC(=O)c1cnc(C)[nH]c1=O]

To a solution of sodium (2.90 g, 126 mmol) in ethanol (150 mL) was added acetoamidine hydrochloride (11.9 g, 126 mmol) at 0° C. The mixture was stirred at 0° C. for 20 minutes, diethyl (ethoxymethylene)malonate (28.6 g, 132 mmol) was added dropwise thereto, the mixture was stirred at 0° C. for 30 minutes, and triethylamine (20 mL, 145 mmol) was added thereto. The mixture was heated under reflux for 2 hours, the reaction mixture was concentrated, water (400 mL) was added thereto, citric acid was added to adjust pH to 4 to 5, and the mixture was extracted with dichloromethane (200 mL) three times. The organic layers were combined, dried over anhydrous sodium sulfate, filtrated, and concentrated. To the resulting concentrated residue was added tert-butyl methyl ether (200 mL), and the precipitate was collected on a filter to give the title compound (14.0 g, 61%)

$^1$H-NMR (400 MHz, $CDCl_3$) δ: 1.40 (3H, t, J=7.2 Hz), 2.61 (3H, s), 4.39 (2H, q, J=7.2 Hz), 8.73 (1H, s).

Reference Example 35

6'-Methyl-1',2',3',6'-tetrahydro-2,4'-bipyridine dihydrochloride

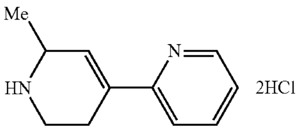 [SMILES: CC1C=C(c2ccccn2)CCN1]

To a solution of the compound of Reference Example 36 (521 mg, 1.9 mmol) in 1,4-dioxane (2 mL) was added 4 mol/L hydrochloric acid/1,4-dioxane solution (2 mL). The mixture was stirred at room temperature for 6 hours, and concentrated. The resulting solid was washed with hexane, and dried to give the title compound (382 mg, 73%).

LC-MS: condition A R.T.=1.0 min ObsMS=177.1 [M+1]

Reference Example 36 tert-Butyl 6'-methyl-3',6'-dihydro-2,4'-bipyridine-1'(2'H)-carboxylate

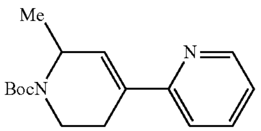 [SMILES: CC1C=C(c2ccccn2)CCN1C(=O)OC(C)(C)C]

To a solution of the compound of Reference Example 37 (1.4 g, 4.3 mmol) in 1,4-dioxane (10 mL) were added 2-bromopyridine (686 mg, 4.3 mmol), tetrakis(triphenylphosphino)palladium (0) (993 mg, 0.86 mmol), and tripotassium phosphate (2.7 g, 12.9 mmol). The mixture was stirred at 80° C. for 6 hours, cooled to room temperature, and the precipitate was removed through Celite®. The filtrate was concentrated, and the residue was dissolved in ethyl acetate. The organic layer was washed with water and saturated aqueous sodium hydrochloride solution, dried over anhydrous sodium sulfate, filtrated, and concentrated. The resulting residue was purified by silica gel column chromatography (hexane:ethyl acetate=1:5) to give the title compound (521 mg, 44%).

$^1$H-NMR (400 MHz, $CDCl_3$) δ: 1.16, 1.29 (d, J=6.8 Hz, 3H, diastereo ratio=4:3), 1.49 (s, 9H), 2.54-2.67 (m, 2H), 2.73-2.80 (m, 0.5H), 2.90-3.05 (m, 0.5H), 3.75-3.80 (m, 0.5H), 4.41-4.46 (m, 0.5H), 4.69 (brs, 1H), 6.55-6.61 (m, 1H), 7.31-7.39 (m, 2H), 7.14-7.17 (m, 1H), 7.31-7.39 (m, 2H), 7.63-7.67 (m, 1H), 8.56-8.58 (m, 1H).

LC-MS: condition A R.T.=6.6 min ObsMS=275.1 [M+1]

Reference Example 37 tert-Butyl 6-methyl-4-(4,4,5,5-tetramethyl-1,3,2-dioxaborolan-2-yl)-3,6-dihydropyridine-1(2H)-carboxylate

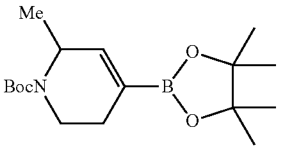 [SMILES: CC1C=C(B2OC(C)(C)C(C)(C)O2)CCN1C(=O)OC(C)(C)C]

To a solution of the compound of Reference Example 38 (1.8 g, 5.2 mmol) in 1,4-dioxane (30 mL) were added bis(pinacolato)diboron (1.4 g, 5.7 mmol), 1,1'-bis(diphenylphosphino)ferrocene-palladium (II) dichloride (761 mg, 1.04 mmol), and potassium acetate (1.50 g, 15.6 mmol). The mixture was stirred at 80° C. for 6 hours, cooled to room temperature, and the precipitate was removed through Celite®. The filtrate was concentrated, the residue was dissolved in ethyl acetate, and then the organic layer was washed with water and saturated aqueous sodium chloride solution, dried over anhydrous sodium sulfate, filtrated, and concentrated. The resulting residue was purified by silica gel column chromatography (hexane:ethyl acetate=5:1) to give the title compound (1.40 g, 84%).

LC-MS: condition A R.T.=9.2 min ObsMS=346.1 [M+23]

Reference Example 38 tert-Butyl 6-methyl-4-{[(trifluoromethyl)sulfonyl]oxa}-3,6-dihydropyridine-1(2H)-carboxylate

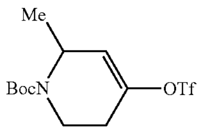

To a solution of 1-(tert-butoxycarbonyl)-2-methylpiperidin-4-one (1.00 g, 4.7 mmol) in tetrahydrofuran (10 mL) was added dropwise 1.5 mol/L solution of lithium diisopropylamide in tetrahydrofuran (3.7 mL, 5.6 mmol) at −78° C. The mixture was stirred for 10 minutes, then a solution of N-phenylbis(trifluoromethanesulfonimide) (1.9 g, 5.6 mmol) in tetrahydrofuran (5 mL) was added dropwise thereto, and the reaction mixture was gradually raised to room temperature. The mixture was stirred for 6 hours, then saturated aqueous ammonium chloride solution was added thereto, and the reaction mixture was extracted with ethyl acetate. The organic layer was washed with saturated aqueous sodium hydrochloride solution, dried over anhydrous sodium sulfate, filtrated, and concentrated. The resulting residue was purified by silica gel column chromatography (hexane:chloroform=5:1) to give the title compound (1.6 g, quantitative).

$^1$H-NMR (400 MHz, $CDCl_3$) δ: 1.18, 1.24 (d, J=6.8 Hz, 3H, diastereo ratio=3:2), 1.47 (s, 9H), 2.05-2.23 (m, 1H), 2.59-2.99 (m, 1H), 3.62-3.76 (m, 1H), 4.20-4.67 (m, 2H), 5.71, 5.75 (s, 1H, diastereo ratio=3:2).

LC-MS: condition A R.T.=8.4 min ObsMS=368.0 [M+23]

Reference Example 39

3-(2-Methylpiperidin-4-yl)pyridine dihydrochloride

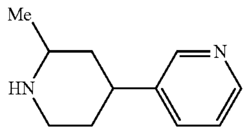
2HCl

The title compound was prepared from the compound of Reference Example 40 according to a similar process to that of Reference Example 35 (yield: quantitative).

LC-MS: condition A R.T.=2.0 min ObsMS=177.0 [M+1]

Reference Example 40 tert-Butyl 2-methyl-4-(pyridin-3-yl)piperidine-1-carboxylate

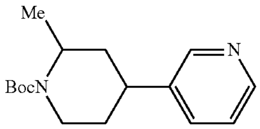 [SMILES: CC1CC(c2cccnc2)CCN1C(=O)OC(C)(C)C]

To a solution of the compound of Reference Example 41 (58 mg, 0.21 mmol) in methanol (3 mL) was added 10% palladium/carbon (50 mg). The mixture was stirred under hydrogen atmosphere at room temperature for 4 hours, filtrated through Celite®, and concentrated to give the title compound (58 mg, quantitative).

$^1$H-NMR (400 MHz, $CDCl_3$) δ: 1.17, 1.28 (d, J=6.8 Hz, 3H, diastereo ratio=1:1), 1.50 (s, 9H), 2.21-2.40 (m, 1H), 2.50-2.62 (m, 0.5H), 2.80-2.84 (m, 0.5H), 2.95-3.04 (m, 0.5H), 3.71-3.76 (m, 0.5H), 4.20-4.42 (m, 2H), 4.69 (brs, 1H), 6.03-6.08 (m, 1H), 7.24-7.29 (m, 1H), 7.63-7.66 (m, 1H), 8.49-8.50 (m, 1H), 8.64-8.65 (m, 1H).

LC-MS: condition A R.T.=6.1 min ObsMS=277.1 [M+1]

Reference Example 41 tert-Butyl 6'-methyl-3',6'-dihydro-3,4'-bipyridine-1'(2'H)-carboxylate

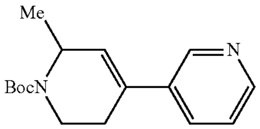

To a solution of the compound of Reference Example 38 (150 mg, 0.43 mmol) in 1,4-dioxane (1.5 mL) were added water (0.5 mL), 3-pyridylboronic acid (64 mg, 0.52 mmol), and 1,1'-bis(diphenylphosphino)ferrocene-palladium (II) dichloride (63 mg, 0.10 mmol), and sodium carbonate (228 mg, 2.2 mmol), and then the mixture was stirred under microwave irradiation at 100° C. for 10 minutes. The mixture was then filtrated through Celite®, and concentrated. The resulting residue was dissolved in ethyl acetate, and then the organic layer was washed with water and saturated aqueous sodium chloride solution, dried over anhydrous sodium sulfate, filtrated, and concentrated. The resulting residue was purified by silica gel column chromatography (hexane:ethyl acetate=5:1) to give the title compound (58 mg, 49%).

LC-MS: condition A R.T.=6.6 min ObsMS=275.1 [M+1]

Reference Example 42-45

According to the above processes of Reference Examples 35-38, the compounds of Reference Examples 42-45 were synthesized from 1-(tert-butoxycarbonyl)-3-methylpiperidin-4-one.

| Reference Examples | Chemical Structure | Instrumental Analysis Data |
| --- | --- | --- |
| 42 | 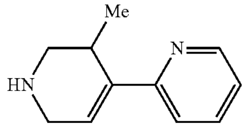 2HCl | LC-MS: condition A<br>R.T. = 1.0 min<br>ObsMS = 177.1 [M + 1] |
| 43 | 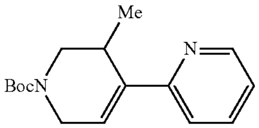 [SMILES: CC1CN(C(=O)OC(C)(C)C)CC=C1c1ccccn1] | $^1$H-NMR (400 MHz, $CDCl_3$) δ: 1.02 (d, J = 6.8 Hz, 3H), 1.48 (s, 9H), 2.84 (brs, 1H), 3.33 (dd, J = 13.2, 3.4 Hz, 1H), 3.82-3.91 (m, 2.2H), 4.20-4.42 (m, 1H), 5.93 (brs, 1H), 7.27 (t, J = 6.3 Hz, 1H), 7.62 (d, J = 7.8 Hz, 1H), 8.51-8.61 (m, 2H). LC-MS: condition A R.T. = 6.6 min ObsMS = 275.1 [M + 1] |
| 44 | 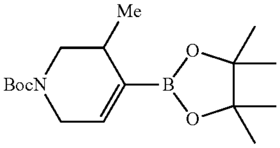 [SMILES: CC1CN(C(=O)OC(C)(C)C)CC=C1B1OC(C)(C)C(C)(C)O1] | LC-MS: condition A<br>R.T. = 9.2 min<br>ObsMS = 346.1 [M + 23] |
| 45 | 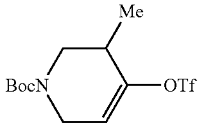 [SMILES: CC1CN(C(=O)OC(C)(C)C)CC=C1OS(=O)(=O)C(F)(F)F] | LC-MS: condition A<br>R.T. = 8.7 min<br>ObsMS = 367.9 [M + 23] |

Reference Example 46

3-(3-Methylpiperidin-4-yl)pyridine dihydrochloride

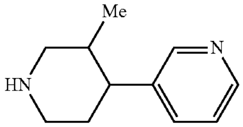

2HCl

The title compound was prepared from the compound of Reference Example 47 according to a similar process to that of Reference Example 35 (yield: 73%).

LC-MS: condition A R.T.=1.0 min ObsMS=177.1 [M+1]

Reference Example 47 tert-Butyl 3-methyl-4-(pyridin-3-yl)piperidine-1-carboxylate

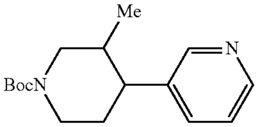 [SMILES: CC1CN(C(=O)OC(C)(C)C)CCC1c1cccnc1]

The title compound was prepared from the compound of Reference Example 48 according to a similar process to that of Reference Example 40 (yield: quantitative)

LC-MS: condition A R.T.=2.0 min ObsMS=277.0 [M+1].

Reference Example 48 tert-Butyl 3'-methyl-3',6'-dihydro-3,4'-bipyridine-1'(2'H)-carboxylate

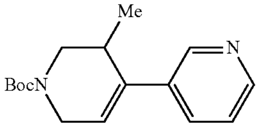 [SMILES: CC1CN(C(=O)OC(C)(C)C)CC=C1c1cccnc1]

The title compound was prepared from the compound of Reference Example 45 according to a similar process to that of Reference Example 41 (yield: 38%).

$^1$H-NMR (400 MHz, $CDCl_3$) δ: 1.02 (d, J=6.8 Hz, 3H), 1.50 (s, 9H), 2.84 (brs, 1H), 3.33 (d, J=13.2, 3.4 Hz, 1H), 3.81-3.95 (m, 2H), 4.18-4.45 (m, 1H), 5.93 (brs, 1H), 7.20-7.30 (m, 1H), 7.62 (d, J=7.8 Hz, 1H), 8.51-8.61 (m, 1H).

LC-MS: condition A R.T.=7.1 min ObsMS=275.1 [M+1]

Reference Examples 49-52

According to the above processes of Reference Examples 35-38, the compounds of Reference Examples 49-52 were synthesized from 1-(tert-butoxycarbonyl)-homopiperazin-4-one.

| Reference Examples | Chemical Structure | Instrumental Analysis Data |
|---|---|---|
| 49 | 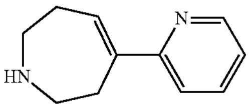 2HCl | LC-MS: condition B R.T. = 0.3 min ObsMS = 177 [M + 1] |
| 50 | 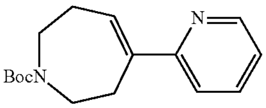 [SMILES: CC(C)(C)OC(=O)N1CCC=C(c2ccccn2)CC1] | LC-MS: condition A R.T. = 7.1 min ObsMS = 275.0 [M + 1] |
| 51 | 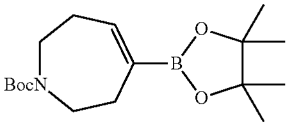 [SMILES: CC(C)(C)OC(=O)N1CCC=C(B2OC(C)(C)C(C)(C)O2)CC1] | LC-MS: condition B R.T. = 2.1 min ObsMS = 346.1 [M + 23] |
| 52 | 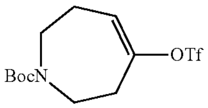 [SMILES: CC(C)(C)OC(=O)N1CCC=C(OS(=O)(=O)C(F)(F)F)CC1] | LC-MS: condition A R.T. = 8.3 min ObsMS = 368.0 [M + 23] |

Reference Example 53

4-(Pyridin-3-yl)-2,3,6,7-tetrahydro-1H-azepine dihydrochloride

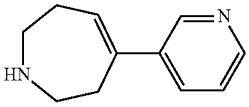

2HCl

The title compound was prepared from the compound of Reference Example 54 according to a similar process to that of Reference Example 35 (yield: 37%).

LC-MS: condition B R.T.=0.3 min ObsMS=175 [M+1]

Reference Example 54 tert-Butyl 4-(pyridin-3-yl)-2,3,6,7-tetrahydro-1H-azepine-1-carboxylate

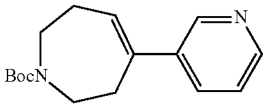 [SMILES: CC(C)(C)OC(=O)N1CCC=C(c2cccnc2)CC1]

The title compound was prepared from the compound of Reference Example 52 according to a similar process to that of Reference Example 41 (yield: 51%).

LC-MS: condition A R.T.=7.1 min ObsMS=275.0 [M+1]

Reference Examples 55-63

According to the above processes of Reference Examples 1-6, the compounds of Reference Examples 55-63 were synthesized from 1-N-Boc-4-(4,4,5,5-tetramethyl-[1,3,2]-dioxaborolan-2-yl)-3,6-dihydro-2H-pyridine.

| Reference Examples | Chemical Structure | Instrumental Analysis Data |
|---|---|---|
| 55 | 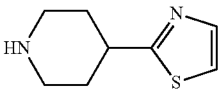 HCl | $^1$H-NMR (400 MHz, $CD_3OD$) δ: 2.08-2.22 (2H, m), 2.40-2.50 (2H, m), 3.20-3.32 (2H, m), 3.53-3.63 (2H, m), 3.74-3.84 (1H, m), 8.02 [1H, d, J = 3.6 Hz) , 8.18 (1H, d, J = 3.6 Hz). |
| 56 | 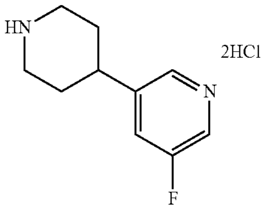 [SMILES: Fc1cncc(C2CCNCC2)c1] 2HCl | $^1$H-NMR (400 MHz, DMSO-$d_6$) δ: 1.89-2.05 (4H, m), 2.89-3.03 (2H, m), 3.03-3.15 (1H, m), 3.29-3.42 (2H, m), 7.96 (1H, d, J = 10.0 Hz), 8.53 (1H, s), 8.72 (1H, d, J = 2.0 Hz), 9.24-9.49 (2H, m). |
| 57 | 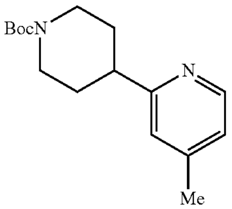 [SMILES: Cc1ccnc(C2CCN(C(=O)OC(C)(C)C)CC2)c1] | $^1$H-NMR (400 MHz, $CDCl_3$) δ: 1.48 (9H, s), 1.61-1.76 (2H, m), 1.81-1.93 (2H, m), 2.31 (3H, s), 2.70-2.93 (3H, m), 6.88-6.98 (2H, m), 8.36 (1H, d, J = 5.2 Hz). |

-continued

| Reference Examples | Chemical Structure | Instrumental Analysis Data |
|---|---|---|
| 58 | 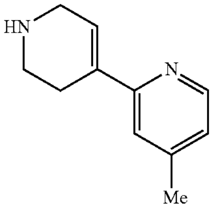 2HCl | $^1$H-NMR (400 MHz, $CD_3OD$) δ: 2.46 (3H, s), 2.71 (2H, brs), 3.06 (2H, brs), 3.80 (2H, brs), 6.59 (1H, brs), 7.62 (1H, d, J = 6.0 Hz), 7.84 (1H, s), 8.37 (1H, d, J = 6.0 Hz). |
| 59 | 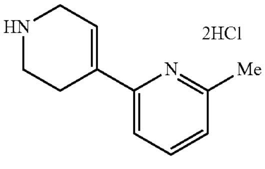 [SMILES: Cc1cccc(C2=CCNCC2)n1] 2HCl | $^1$H-NMR (400 MHz, $CD_3OD$) δ: 2.88 (3H, s), 2.97 (2H, brs), 3.56 (2H, t, J = 6.0 Hz), 4.05 (2H, d, J = 2.8 Hz), 6.75 (1H, brs), 7.87 (1H, d, J = 8.0 Hz), 7.96 (1H, d, J = 8.0 Hz), 8.49 (1H, dd, J = 8.0, 8.0 Hz). |
| 60 | 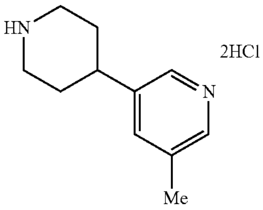 [SMILES: Cc1cncc(C2CCNCC2)c1] 2HCl | $^1$H-NMR (400 MHz, $CD_3OD$) δ: 1.97-2.15 (2H, m), 2.15-2.26 (2H, m), 2.60 (3H, s), 3.15-3.29 (3H, m), 3.51-3.63 (2H, m), 8.52 (1H, s), 8.66 (1H, s), 8.71 (1H, s). |
| 61 | 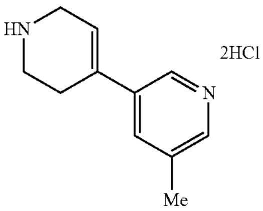 [SMILES: Cc1cncc(C2=CCNCC2)c1] 2HCl | $^1$H-NMR (400 MHz, $CD_3OD$) δ: 2.61 (3H, s), 2.89 (2H, brs), 3.53 (2H, t, J = 6.0 Hz), 3.96 (2H, d, J = 3.2 Hz), 6.57 (1H, brs), 8.63 (1H, s), 8.68 (1H, s), 8.84 (1H, 5). |
| 62 | 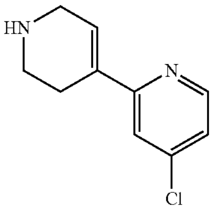 2HCl | $^1$H-NMR (400 MHz, DMSO-$d_6$) δ: 2.77 (2H, brs), 3.28 (2H, brs), 3.78 (2H, brs), 6.84 (1H, s), 7.50 (1H, d, J = 5.4 Hz), 7.79 (1H, s), 8.55 (1H, d, J = 5.4 Hz), 9.55 (2H, brs). |
| 63 | 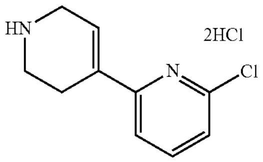 [SMILES: Clc1cccc(C2=CCNCC2)n1] 2HCl | $^1$H-NMR (400 MHz, DMSO-$d_6$) δ: 2.72 (2H, brs), 3.29 (2H, brs), 3.79 (2H, brs), 6.75 (1H, s), 7.44 (1H, d, J = 8.0 Hz), 7.62 (1H, d, J = 8.0 Hz), 7.88 (1H, dd, J = 8.0, 8.0 Hz), 9.29 (2H, brs). |

Test Examples

Hereinafter, pharmacological test results on representative compounds of the present invention are shown and pharmacological effects of the compounds are explained, but the present invention should not be limited thereto.

Effect of the Present Compound on G Protein Dependent Pathway in Dopamine $D_4$ Receptor The G protein dependent pathway is a pathway for transmitting signals in cells via a second messenger by stimulating a G protein through the binding of guanosine triphosphate (GTP) to the G protein. When GPCRs are activated by the binding of a ligand, a G protein binds to the GPCRs, and thereby GTP binds to a Gα subunit that is one of G protein subunits and a Gγβ subunit is dissociated. The activated Gα subunit regulates intracellular cAMP levels by the activation inhibition of adenylate and regulates intracellular calcium levels by the activation of a phospholipase C to transmit signals in cells. Hence, the activation of the G protein dependent pathway can be evaluated by measuring intracellular cAMP levels and intracellular calcium levels.

In this study, the effects of the present compound on dopamine $D_4$ receptor as well as dopamine $D_2$ receptor and adrenergic $\alpha_1$ and $\alpha_2$ receptors were measured to evaluate the receptor selectivity of the present compound in the G protein dependent pathway.

Preparation of Expressing Cell Lines

Human dopamine $D_2$ and $D_4$ receptors, human adrenergic $\alpha_{1A}$ and $\alpha_{2A}$ receptors, calcium-binding photo protein aequorin, and Gα16 cDNA were derived by a PCR method. Plasmids encoding each receptor, aequorin and Gα16 were prepared, and the plasmids were transfected into CHO cells (Chinese Hamster Ovary cells) or HEK293 cells (Human Embryonic Kidney 293 cells) to prepare expressing cell lines.

Measurement of Activity in G Protein Dependent Pathway

Test Example 1

Evaluation of Agonistic Activity and Selectivity for Receptor

The agonistic or antagonistic activity of the present compound in the G protein dependent pathway was evaluated on the basis of intracellular calcium levels as follows. CHO-K1 or HEK293 cell lines transfected with $D_2$, $D_4$, $\alpha_{1A}$, or $\alpha_{2A}$ receptor genes were seeded in a 384-well plate, and incubated in a $CO_2$ incubator at 37° C. for 24 hours, and then a solution of the present compound in DMSO was added into cells preloaded with coelenterazine to measure the change in luminescent signals with a FDSS (Hamamatsu Photonics K.K.). The luminescent signals in the wells without the present compound were defined as 0%, and the luminescent signals in the wells with 10 μM of an endogenous ligand (dopamine or adrenaline) were defined as 100%. The agonistic activity of the present compound was calculated according to the measured luminescent signals, as the maximal activity (Emax) of the present compound. On the other hand, the antagonistic activity of the present compound was calculated according to the luminescent signals in wells with 10 μM of an endogenous ligand alone defined as 100%, as the inhibitory activity of the present compound to an endogenous ligand. $EC_{50}$ value was calculated as the concentration of the present compound required to achieve a 50% response, and $IC_{50}$ was calculated as the concentration of the present compound required to achieve a 50% inhibition of the Emax of an endogenous ligand.

The results of Test Example 1 are shown in Tables 1, 2, and 3. Comparison Example is a result of the compound of Example 14 in Patent Reference 1 in a similar test to that of the present compound.

TABLE 1

| | Maximal activity on each receptor (%) upper: 1 μM lower: 0.1 μM | | | | Inhibitory activity on each receptor (%) upper: 1 μM lower: 0.1 μM | | | |
|---|---|---|---|---|---|---|---|---|
| | $D_2$ | $D_4$ | $\alpha_{1A}$ | $\alpha_{2A}$ | $D_2$ | $D_4$ | $\alpha_{1A}$ | $\alpha_{2A}$ |
| Example 2 | 0.35 | 54 | 1.4 | 0.12 | 26 | 98 | −12 | −2.9 |
| | 0.66 | 45 | 2 | 0.47 | 13 | 94 | −0.7 | −3.3 |
| Example 5 | 1.1 | 74 | −0.1 | −0.04 | 9.9 | 90 | −1.7 | −1.7 |
| | 0.19 | 59 | 2.1 | −0.17 | −1.7 | 78 | 2.1 | −7 |
| Example 33 | 1.7 | 51 | 0.85 | −0.12 | 1.2 | 98 | −5.4 | 7.8 |
| | 0.29 | 28 | 0.4 | −0.1 | −5.3 | 76 | −34 | 0.91 |
| Example 37 | 18 | 40 | 0.44 | −0.27 | 47 | 77 | −14 | 0.24 |
| | 5.4 | 18 | 0.31 | −0.17 | 14 | 64 | −22 | 7.9 |
| Comparison | 13 | 30 | 0.16 | 0.34 | 59 | 105 | 57 | 99 |
| Example | 2.2 | 24 | 0.3 | 0.49 | 38 | 104 | 28 | 93 |

TABLE 2

| | Maximal activity on each receptor (%) upper: 1 μM lower: 0.1 μM | | Inhibitory activity on each receptor (%) upper: 1 μM lower: 0.1 μM | |
|---|---|---|---|---|
| | $D_4$ | $\alpha_{1A}$ | $D_4$ | $\alpha_{1A}$ |
| Example 44 | 64 | 0.01 | 78 | 2.6 |
| | 27 | 0.04 | 58 | 2.7 |
| Example 45 | 35 | 0.08 | 87 | −0.73 |
| | 20 | 0.03 | 72 | −5.6 |
| Example 46 | 40 | 0.23 | 85 | −17 |
| | 14 | 0.08 | 61 | −6.4 |

TABLE 3

| | Maximal activity on $D_4$ receptor (%): 1 μM |
|---|---|
| Example 1 | 62 |
| Example 3 | 69 |
| Example 4 | 65 |
| Example 6 | 63 |
| Example 7 | 64 |
| Example 8 | 62 |
| Example 9 | 70 |
| Example 10 | 110 |
| Example 11 | 93 |
| Example 12 | 101 |
| Example 13 | 81 |
| Example 14 | 87 |
| Example 15 | 131 |
| Example 16 | 78 |
| Example 17 | 72 |
| Example 18 | 58 |
| Example 19 | 64 |
| Example 20 | 54 |
| Example 21 | 93 |
| Example 22 | 72 |
| Example 23 | 105 |
| Example 24 | 103 |
| Example 25 | 71 |
| Example 26 | 75 |
| Example 27 | 66 |
| Example 28 | 62 |
| Example 29 | 107 |
| Example 30 | 86 |
| Example 31 | 82 |
| Example 32 | 68 |
| Example 34 | 93 |
| Example 35 | 86 |
| Example 36 | 82 |
| Example 38 | 51 |
| Example 39 | 49 |
| Example 40 | 72 |
| Example 41 | 59 |
| Example 42 | 71 |
| Example 43 | 92 |
| Example 47 | 51 |
| Example 48 | 62 |
| Example 49 | 66 |
| Example 50 | 70 |
| Example 51 | 88 |
| Example 52 | 67 |
| Example 53 | 66 |
| Example 54 | 60 |
| Example 55 | 88 |
| Example 56 | 40 |
| Example 57 | 62 |

Effect of the Present Compound on G Protein Independent Pathway in Dopamine $D_4$ Receptor The G protein independent pathway is an intracellular signaling pathway in which a G protein is not involved. When GPCRs are activated by the binding of a ligand, GRKs (G protein coupled receptor kinases) phosphorylate the GPCRs, and then β-arrestin binds to the phosphorylated GPCRs. When β-arrestin binds to GPCRs, various pathways such as MAPK (mitogen-actiated protein kinase), Protein Kinase B (PKB), PI3 kinase (Phosphoinositide 3-kinase), and NFκB (nuclear factor-kappa B) pathways are activated to transmit G protein independent signals in cells. Also, it is known that the binding of β-arrestin to a GPCR leads to the internalization of the GPCR, and thus β-arrestin is involved in the desensitization of the GPCR. Hence, the activation of the G protein independent pathway can be evaluated by measuring the recruit ability of β-arrestin to GPCRs.

In this study, the effect of the present compound on the G protein independent pathway in dopamine $D_4$ receptor were evaluated by measuring intracellular calcium levels and the recruit ability of β-arrestin.

Preparation of Expressing Cell Lines

Plasmids encoding a fusion protein of human dopamine $D_4$ receptor and a small fragment of β-galactosidase purchased from DiscoveRx (ProLink™) as well as a fusion protein of β-arrestin and a large fragment of β-galactosidase (Enzyme Acceptor) were prepared, and then the plasmids were transfected into CHO cells or HEK293 cells to prepare transient or stable expressing cell lines.

Measurement of Activity in G-Protein Independent Pathway

Test Example 2

Evaluation of Effect of the Present Compound on G Protein Independent Pathway in Dopamine $D_4$ Receptor The activation of the G protein independent pathway was evaluated on the basis of the recruit ability of β-arrestin as follows. Cell lines transfected with $D_4$ receptor genes were seeded in a 384-well plate, and incubated in a $CO_2$ incubator at 37° C. for 24 hours, a solution of the present compound in DMSO was added into the cells, and then the cells were left at 37° C. for 90 minutes. Buffer containing β-galactosidase reaction substance (PathHunter Cell Assay Buffer, DiscoverRx) was added thereto, and luminescent signals in the wells were measured with a FDSS (Hamamatsu Photonics K.K.). The luminescent signals in the wells with no addition of the present compound were defined as 0%, and the luminescent signals in the wells with 10 μM of an endogenous ligand (dopamine) were defined as 100%. The maximal activity (Emax) of the present compound was calculated according to the measured luminescent signals. $EC_{50}$ value was calculated as the concentration of the present compound required to achieve a 50 response.

The result of Test Example 2 is shown in Table 4. Also, in light of the results of Tables 1-3, it has been found that the compounds of the present invention are biased ligands which exhibit an agonistic effect on $D_4$ receptor in the G protein dependent pathway while exhibiting a weaker effect on $D_4$ receptor than dopamine that is an endogenous ligand in the G protein independent pathway.

TABLE 4

| Examples | Maximal activity on $D_4$ receptor (%) |
|---|---|
| Dopamine | 100 |
| 2 | 16 |
| 5 | 11 |
| 33 | 21 |

TABLE 4-continued

| Examples | Maximal activity on $D_4$ receptor (%) |
|---|---|
| 37 | 9 |
| 44 | 6 |
| 45 | 9 |
| 46 | 11 |

Test Example 3

Evaluation of Bioavailability

PK Study in Rat

In this study, the pharmacokinetics of the present compound can be evaluated. Specifically, a 7-week-old SD-type or WKY-type rat received the intravenous administration of a solution of the present compound in saline or the oral administration of a suspension of the present compound in carboxymethylcellulose or methylcellulose. Blood was collected from the rat at each time below.

Intravenous administration: 5 minutes, 15 minutes, 30 minutes, 1 hour, 2 hours, 4 hours, 6 hours, and 24 hours after administration Oral administration: 15 minutes, 30 minutes, 1 hour, 2 hours, 4 hours, 6 hours, and 24 hours after administration Plasma was collected from the blood, the levels of the present compound in the plasma were measured by a LC-MS method, and then the pharmacokinetic parameters were calculated on the basis of the level changes.

Test Example 4

Evaluation of Brain Penetration

Brain Penetration Study in Rat

In this study, the brain penetration of the present compound can be evaluated. Specifically, a 7-week-old SD-type or WKY-type rat received the subcutaneous administration of a solution of the present compound in saline or the oral administration of a suspension of the present compound in methylcellulose. Plasma and brain were collected from the treated rat 0.5 hour, 1 hour or 2 hours after the administration, and then the levels of the present compound in the plasma and the brain were measured by a LC-MS method.

The protein binding ratios of the present compound to the plasma and the brain were measured by an equilibrium dialysis method.

The levels of the present compound in the plasma and the brain as well as the plasma and brain protein binding ratios are applied to the following formula, and thus Kp,uu,brain (Unbound brain-to-plasma drug concentration ratio) can be calculated.

Kp,uu,brain=(level of the present compound in the brain×(100−brain protein binding ratio (%))/100)/(level of the present compound in the plasma×(100−plasma protein binding ratio (%))/100)

The results of Test Examples 3 and 4 are shown in Table 5. Comparison Example is a result that the compound of Example 14 in Patent Reference 1 was tested in a similar method to that of the present compound.

TABLE 5

| | Bioavailability (%) | Kp, uu, brain |
|---|---|---|
| Example 2 | 43.1 | 0.29 |
| Example 5 | 16.8 | 1.97 |
| Example 33 | 60.1 | 0.44 |
| Example 36 | 67.2 | 2.28 |
| Example 37 | 81.7 | 5.51 |
| Example 44 | 27.6 | 0.80 |
| Example 45 | 21.6 | 0.80 |
| Example 46 | 92.2 | 1.80 |
| Comparison Example | 7.6 | 1.37 |

Test Example 5

Evaluation of Risk for Hepatotoxicity

Dansyl Glutathione (dGSH) Trapping Assay

The present compound was metabolized to a metabolite thereof by hepatic microsome, and the resulting metabolite was tested to detect a reactive metabolite therein which can react with dansyl glutathione (dGSH) and quantify the reactive metabolite. The metabolism was induced with a screening robot (Tecan), and the level of a metabolite-dGSH conjugate was measured with a fluorescence detection UPLC system (Waters).

(Preparation of Solution)

The present compound was dissolved in DMSO to prepare 10 mmol/L of a test substance solution. 7.6 mL of potassium phosphate buffer (500 mmol/L, pH 7.4), 1.9 mL of human hepatic microsome (Xenotech, 20 mg protein/mL), and 1.27 mL of pure water were mixed to prepare a microsome solution. To 3.78 mL of the microsome solution was added 0.67 mL of pure water to prepare a microsome (dGSH (−)) solution. To 6.48 mL of the microsome solution was added 1.14 mL of a dGSH solution (20 mmol/L) to prepare a microsome (dGSH (+)) solution. 80.9 mg of NADPH was dissolved in 30 mL of pure water to prepare a cofactor solution. 33 mg of tris(2-carboxyethyl)phosphine (TECP) was dissolved in 115 mL of methanol to prepare a reaction-stopping solution.

(Reaction)

12 μL of the test substance solution was mixed with 388 μL of pure water, and then the mixture was put into 6 wells in an amount of 50 μL per well in a 96-well plate. The 6 wells were classified into 3 groups by 2 wells, and each group was defined as “reacted group”, “unreacted group”, and “group without dGSH”. The microsome (dGSH (+)) solution was added into the wells of the “reacted group” and the “unreacted group” in an amount of 50 μL per well, and the microsome (dGSH (−)) solution was added in the wells of the “group without dGSH” in an amount of 50 μL per well. The cofactor solution was added into the wells of the “reacted group” and the “group without dGSH” in an amount of 50 μL per well, and pure water was added into the wells of the “unreacted group” in an amount of 50 μL per well. The groups were incubated at 37° C. for 60 minutes, and the reaction-stopping solution was added into the wells of the groups in an amount of 450 μL per well to stop the reaction. Pure water was added into the wells of the “reacted group” and the “group without dGSH” in an amount of 50 μL per well, the cofactor solution was added into the wells of the “unreacted group” in an amount of 50 μL per well, and the plate was cooled at −20° C. for 1 hour, and then centrifuged (4000 rpm, 10 minutes). The supernatant was collected into another plate, and the plate was analyzed.

(Analysis)

The level of the metabolite-dGSH conjugate was measured with a fluorescence detection UPLC system (Waters) under the following conditions.

Column: Waters ACQUITY UPLC BFHC 18 1.7 μm 2.1×10 mm

Elution Solvent: A, 0.2% formic acid/40% methanol; B, 0.2% formic acid/methanol

Gradient: B, 0% (0 min)=>83.3% (9.33 min)=>83.3% (10.63 min)=>0% (10.64 min)=>0% (13 min)

Fluorescence intensity varied according to organic solvent compositions, and thus was corrected with that of the organic solvent composition at the time of elution.

The result of Test Example 5 is shown in Table 6. Comparison Example is a result that the compound of Example 14 in Patent Reference 1 was tested in a similar method to Test Example 5. The covalent binding level of the compound of Comparison Example and dGSH was 0.777 μM. On the other hand, the covalent binding levels of each compound of Examples 2, 5, 33, 36, 37, 44, 45, and 46 and dGSH were less than detection threshold.

TABLE 6

| | Level of metabolite-dGSH conjugate (μM) |
|---|---|
| Example 2 | 0 |
| Example 5 | 0 |
| Example 33 | 0 |
| Example 36 | 0 |
| Example 37 | 0 |
| Example 44 | 0 |
| Example 45 | 0 |
| Example 46 | 0 |
| Comparison Example | 0.777 |

Test Example 6

Evaluation of Pharmacological Effect of the Present Compound on Hyperactivity in SHR Rat A juvenile SHR rat has been widely used as an ADHD model with high validity. The inhibitory effect of the present compounds on hyperactivity in the rat was evaluated in an open-field test. Specifically, a 7-week-old SHR rat received the oral administration of the present compound, and the locomotor activity level in the rat was measured for 90 minutes from 30 minutes after the administration. The measurement was performed with SuperMex (Muromachi Kikai Co., Ltd.). The total locomotor activity level for 90 minutes after the administration of the present compound was statistically expressed as an inhibition ratio in the range of 0% to 100% on the basis of the locomotor activity level in the vehicle administration group. As shown in Table 7, the compounds of Examples 2 and 5 inhibited hyperactivity in the SHR rat.

TABLE 7

| | Inhibition ratio (%) 10 mg/kg |
|---|---|
| Example 2 | 30.7 |
| Example 5 | 28.5 |

Test Example 7

Figure 2:
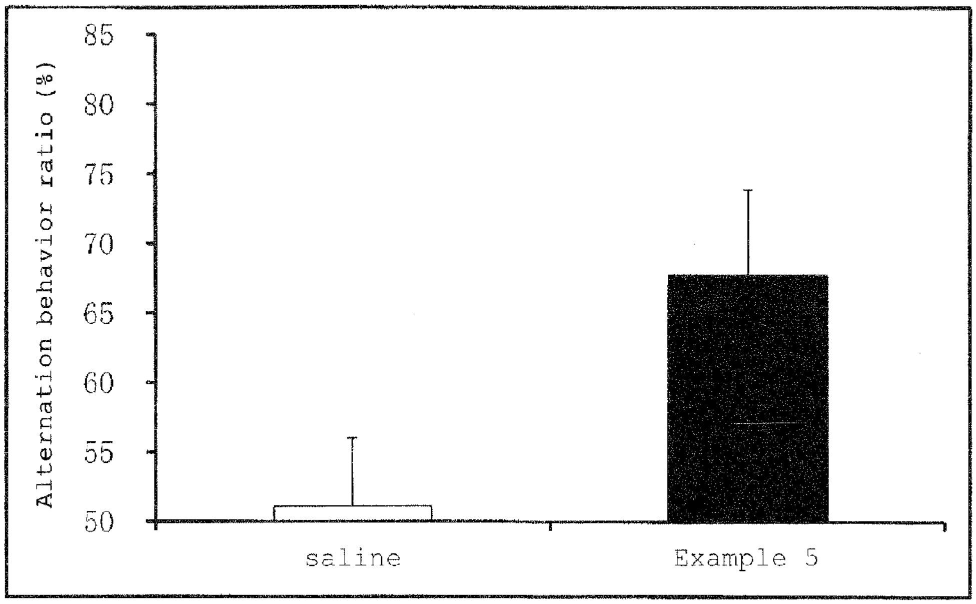
FIG. 2 is a bar graph showing the improvement of alternation behavior ratio (%) with the administration of the compound of Example 5 in Test Example 7.

Evaluation of Pharmacological Effect of the Present Compound on Inattention in SHR Rat It is known that a SHR rat has a lower spontaneous alternation behavior ratio than a WKY rat which is a background animal through the Y-shaped maze test. Thus, the SHR rat was pretreated with the present compound to evaluate the pharmacological effect of the present compound on attention function. Specifically, a 4-week-old SHR rat received the oral administration of the present compound, and a spontaneous alternation behavior ratio in the rat was measured for 8 minutes from 30 minutes after the administration. The improved spontaneous alternation behavior ratio (%) was calculated as a numerical value on the basis of the spontaneous alternation behavior ratio in the vehicle administration group. In this study, a Y-shaped maze device (black acrylic: 450 mm×100 mm×350 mm, Horikawa Manufacturing Co., Ltd.) was used. The compounds of Example 2 (10 mg/kg administration) and Example 5 (1 mg/kg administration) significantly improved the spontaneous alternation behavior ratio in the rat (see, FIGS. 1 and 2).

Test Example 8

Evaluation of Pharmacological Effect of the Present Compound on Social Impairments in Rat after Prenatal Exposure to Valproic Acid A rat exposed to valproic acid on the 12.5 days of fetal life has been widely used as an autistic rat model with high validity. It is known that the rat has a social cognitive disorder through the three-chamber test which is a test for evaluating sociability. Thus, the rat was pretreated with the present compound to evaluate the improved effect of the present compound on social cognition. In this study, a sociability cage (600 mm×400 mm×220 mm, Muromachi Kikai Co., Ltd.) was used. Specifically, a 3-week-old rat after prenatal exposure to valproic acid received the oral administration of the present compound, and the time that the rat stayed in close to another rat side or a novel object was measured for 10 minutes from 30 minutes after the administration. The ratio of the time for another rat side to the time for a novel object that is defined as 100% was calculated to evaluate the improvement ratio (%) of the present compound on the basis of the result of the vehicle-treated group. The improvement ratio after the oral administration of the compound of Example 5 (1 mg/kg) was 27.6%. As a result, the compound of Example 5 significantly increased the time that the rat stayed in close to another rat side.

INDUSTRIAL APPLICABILITY

The present compound exhibits high selectivity for dopamine $D_4$ receptors, and thus is useful for treating a disease such as attention deficit hyperactivity disorder.

The invention claimed is:

1. A compound of formula (1):

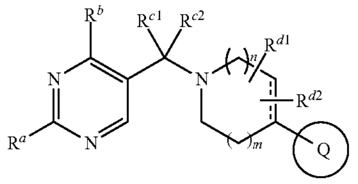
(1)

or a pharmaceutically acceptable salt thereof, wherein n and m are independently 1 or 2;

$R^a$ is $C_{1-6}$ alkyl group or $C_{3-6}$ cycloalkyl group;

$R^b$ is $C_{1-6}$ alkyl group, or amino group which may be optionally substituted with the same or different one or two $C_{1-6}$ alkyl groups;

$R^{c1}$ and $R^{c2}$ are independently hydrogen atom or $C_{1-6}$ alkyl group;

$R^{d1}$ and $R^{d2}$ are independently hydrogen atom, fluorine atom, or $C_{1-6}$ alkyl group, or $R^{d1}$ and $R^{d2}$ may be combined with the carbon atom(s) to which they are attached to form a 3- to 8-membered cycloalkane ring or a 3- to 8-membered cycloalkene ring, wherein the cycloalkane ring or cycloalkene ring may be optionally substituted with one or two substituents selected independently from the group consisting of halogen atom, $C_{1-6}$ alkyl, and $C_{1-6}$ alkoxy;

ring Q is an optionally-substituted 5- to 10-membered nitrogen-containing heteroaryl group; and the bond having a dashed line is a single or double bond.

2. A compound formula (1):

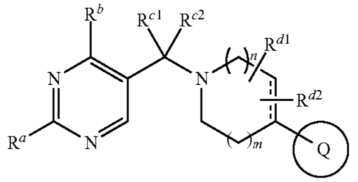
(1)

or a pharmaceutically acceptable salt thereof, wherein n and m are independently 1 or 2;

$R^a$ is $C_{1-6}$ alkyl group, $C_{3-6}$ cycloalkyl group, or amino group;

$R^b$ is hydrogen atom, $C_{1-6}$ alkyl group, or amino group which may be optionally substituted with one or two $C_{1-6}$ alkyl groups, provided that when $R^a$ is amino group, then $R^b$ is hydrogen atom;

$R^{c1}$ and $R^{c2}$ are independently hydrogen atom or $C_{1-6}$ alkyl group;

$R^{d1}$ and $R^{d2}$ are independently hydrogen atom, fluorine atom, or $C_{1-6}$ alkyl group, or $R^{d1}$ and $R^{d2}$ may be combined with the carbon atom(s) to which they are attached to form a 3- to 8-membered cycloalkane ring or a 3- to 8-membered cycloalkene ring, wherein the cycloalkane ring or cycloalkene ring may be optionally substituted with one or two substituents selected from the group consisting of halogen atom, $C_{1-6}$ alkyl and $C_{1-6}$ alkoxy;

ring Q is a group of following formula (2a), (2b), (2d) or (2e):

(2a)

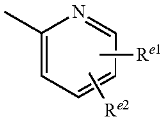

(2b)

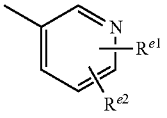

(2d)

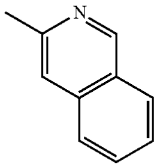

(2e)

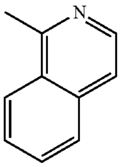

wherein $R^{e1}$ and $R^{e2}$ are independently hydrogen atom or $C_{1-6}$ alkyl group which may be optionally substituted with the same or different one to three halogen atoms; and the bond having a dashed line is a single or double bond.

3. The compound according to claim 1 or a pharmaceutically acceptable salt thereof, wherein the ring Q is a group of the following formula (2a), (2b), (2c), (2d) or (2e):

(2a)

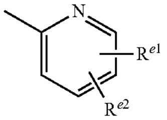

(2b)

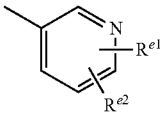

(2c)

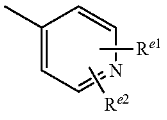

(2d)

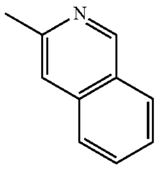

(2e)

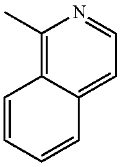

wherein $R^{e1}$ and $R^{e2}$ are independently hydrogen atom, halogen atom, or $C_{1-6}$ alkyl group which may be optionally substituted with the same or different one to three halogen atoms.

4. The compound according to claim 1 or a pharmaceutically acceptable salt thereof, wherein $R^a$ is $C_{1-4}$ alkyl group.

5. The compound according to claim 1 or a pharmaceutically acceptable salt thereof, wherein $R^b$ is $C_{1-6}$ alkyl group or amino group.

6. The compound according to claim 1 or a pharmaceutically acceptable salt thereof, wherein $R^b$ is amino group.

7. The compound according to claim 1 or a pharmaceutically acceptable salt thereof, wherein both $R^{c1}$ and $R^{c2}$ are hydrogen atom.

8. The compound according to claim 1 or a pharmaceutically acceptable salt thereof, wherein $R^{d1}$ and $R^{d2}$ are independently hydrogen atom or $C_{1-6}$ alkyl group.

9. The compound according to claim 1 or a pharmaceutically acceptable salt thereof, wherein both $R^{d1}$ and $R^{d2}$ are hydrogen atom.

10. The compound according to claim 3 or a pharmaceutically acceptable salt thereof, wherein the ring Q is a group of formula (2a) or (2b).

11. The compound according to claim 10 or a pharmaceutically acceptable salt thereof, wherein the ring Q is a group of formula (2a).

12. The compound according to claim 3 or a pharmaceutically acceptable salt thereof, wherein $R^{e1}$ and $^{e2}$ are independently hydrogen atom or fluorine atom.

13. The compound according to claim 1 or a pharmaceutically acceptable salt thereof, wherein the bond having a dashed line is a single bond.

14. The compound according to claim 2 which is selected from the group consisting of the following formulae:

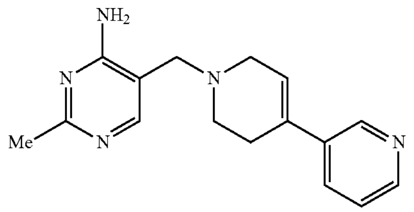

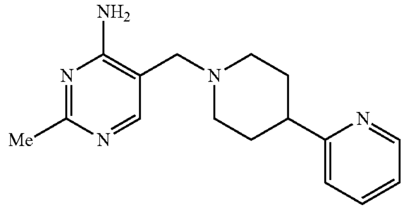

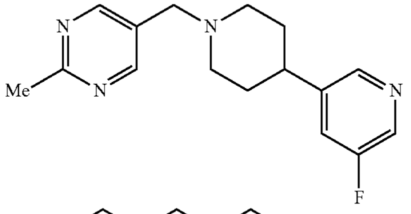

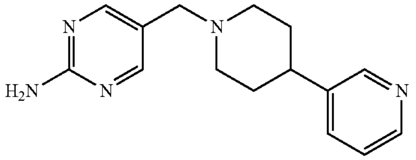

-continued

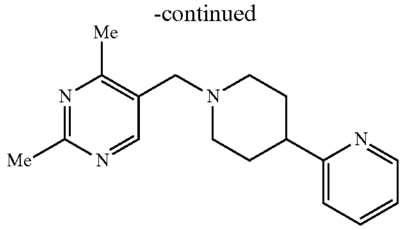

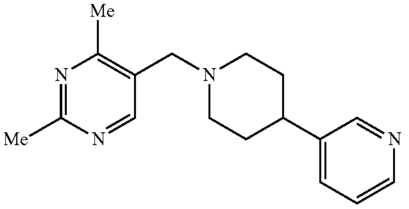

and

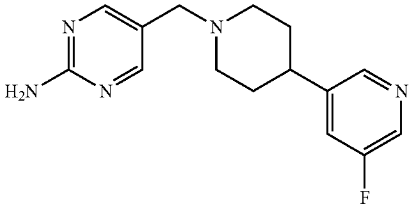

or a pharmaceutically acceptable salt thereof.

15. A medicine comprising the compound according to claim 1 or a pharmaceutically acceptable salt thereof as an active ingredient.

16. A method for treating a central nervous system disease selected from the group consisting of attention deficit hyperactivity disorder, autism, Asperger's syndrome, atypical pervasive developmental disorder, childhood disintegrative disorder, and schizophrenia, which comprises administering a therapeutically effective amount of the compound according to claim 1 or a pharmaceutically acceptable salt thereof to a patient in need thereof.

17. The method according to claim 16, wherein the disease is attention deficit hyperactivity disorder.

18. The method according to claim 16, wherein the disease is autism.

19. The compound according to claim 1 or a pharmaceutically acceptable salt thereof, wherein n and m are independently 1 or 2;

$R^a$ is $C_{1-6}$ alkyl group or $C_{3-6}$ cycloalkyl group;

$R^b$ is $C_{1-6}$ alkyl group, or amino group which may be optionally substituted with one or two $C_{1-6}$ alkyl groups;

$R^{c1}$ and $R^{c2}$ are independently hydrogen atom or $C_{1-6}$ alkyl group;

$R^{d1}$ and $R^{d2}$ are independently hydrogen atom, fluorine atom, or $C_{1-6}$ alkyl group, or $R^{d1}$ and $R^{d2}$ may be combined with the carbon atom(s) to which they are attached to form a 3- to 8-membered cycloalkane ring or a 3- to 8-membered cycloalkene ring, wherein the cycloalkane ring or cycloalkene ring may be optionally substituted with one or two substituents selected from the group consisting of halogen atom, $C_{1-6}$ alkyl, and $C_{1-6}$ alkoxy;

ring Q is an optionally-substituted pyridyl group or an optionally-substituted isoquinolyl group; and the bond having a dashed line is a single or double bond.

20. A pharmaceutical preparation comprising the compound of claim 1 or a pharmaceutically acceptable salt thereof, and a pharmaceutically acceptable excipient and additive.

* * * * *

UNITED STATES PATENT AND TRADEMARK OFFICE

CERTIFICATE OF CORRECTION

PATENT NO. : 9,732,065 B2
APPLICATION NO. : 14/894402
DATED : August 15, 2017
INVENTOR(S) : Hidefumi Yoshinaga It is certified that error appears in the above-identified patent and that said Letters Patent is hereby corrected as shown below:

In the Claims

Claim 2, in Column 75, Line 28, after "hydrogen atom" and before "or", insert --, halogen atom--.

Signed and Sealed this
Seventh Day of November, 2017

Joseph Matal

*Performing the Functions and Duties of the*
*Under Secretary of Commerce for Intellectual Property and*
*Director of the United States Patent and Trademark Office*